US011162106B2

(12) United States Patent
Verruto et al.

(10) Patent No.: US 11,162,106 B2
(45) Date of Patent: Nov. 2, 2021

(54) INDUCIBLE EXPRESSION OF GENES IN ALGAE

(71) Applicant: Synthetic Genomics, Inc., La Jolla, CA (US)

(72) Inventors: John Verruto, San Diego, CA (US); Jessica Weir, La Jolla, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 16/719,013

(22) Filed: Dec. 18, 2019

(65) Prior Publication Data

US 2020/0199607 A1 Jun. 25, 2020

Related U.S. Application Data

(60) Provisional application No. 62/782,152, filed on Dec. 19, 2018.

(51) Int. Cl.
*C12N 15/113* (2010.01)
*C12N 15/82* (2006.01)
*C07K 14/415* (2006.01)

(52) U.S. Cl.
CPC ........ *C12N 15/8218* (2013.01); *C07K 14/415* (2013.01); *C12N 15/113* (2013.01); *C12N 2310/11* (2013.01); *C12N 2310/141* (2013.01)

(58) Field of Classification Search
None
See application file for complete search history.

(56) References Cited

U.S. PATENT DOCUMENTS

2007/0178451 A1 8/2007 Deng et al.
2007/0261129 A1 11/2007 Andersen et al.
2017/0073695 A1* 3/2017 Verruto .............. C12N 15/8213

OTHER PUBLICATIONS

International Search Report dated Apr. 28, 2020, regarding PCT/US2019/067127.

Niu et al.: "*A new inducible expression system in a transformed green alga, Chlorella vulgaris*"; Genet Mol Res. 2011, 10(4):3427-34.

Potrykus et al.: "*Chloramphenicol-Sensitive Escherichia coli Strain Expressing the Chloramphenicol Acetyltransferase* (*cat*)"; Gene. Antimicrob Agents Chemother. 2001, 45(12): 3610-3612.

* cited by examiner

*Primary Examiner* — Matthew R Keogh
(74) *Attorney, Agent, or Firm* — DLA Piper LLP (US)

(57) ABSTRACT

The present application provides novel algal regulatory elements including inducible nitrate/nitrite promoter sequences and terminator sequences. The application further discloses DNA constructs comprising these novel regulatory elements, and recombinant microorganisms comprising these regulatory elements. Methods of modifying, producing, and using the regulatory elements are also disclosed. Methods disclosed in the present application are suited for inducible expressions of genes, such as a transgene or a native gene in algal species.

24 Claims, 5 Drawing Sheets

Specification includes a Sequence Listing.

Anti-Cre Western Blot

Cre expression
Line #8

WT RM IM

←38kDa

INDUCIBLE EXPRESSION OF GENES IN ALGAE

CROSS-REFERENCE TO RELATED APPLICATIONS

This application claims benefit of priority under 35 U.S.C. § 119(e) of U.S. Ser. No. 62/782,152, filed Dec. 19, 2018, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI2220_1_Sequence_Listing.txt, was created on Dec. 18, 2019, and is 107 kb. The file can be accessed using Microsoft Word on a computer that uses Windows OS.

FIELD OF THE INVENTION

The present invention relates generally to the field of genetic engineering of algal cells for selective expression of genes of interest.

BACKGROUND

Algal cells are a promising source of biofuels (Wijffels & Barbosa (2010) *Science* 329:796-799). Their ability to harness solar energy to convert carbon dioxide into carbon-rich lipids already exceeds the abilities of oil-producing agricultural crops, with the added advantage that algae grown for biofuel do not compete with oil-producing crops for agricultural land (Wijffels & Barbosa, 2010). In order to maximize algal fuel production, new algal strains will need to be engineered for growth and carbon fixation at an industrial scale (Wijffels & Barbosa, 2010).

Further, modern recombinant strain development requires robust and efficient tools for expressing transgenes as well as endogenous genes to alter cellular metabolism and physiology in desired ways. An essential component of any genetic engineering "toolkit" is a suite of functional promoters and terminators to drive transgene or endogenous gene expression. There is a need for endogenous promoters, cloned and verified, from the strains for which recombinant DNA technology is being developed as well as additional strategies for increasing transformation of microorganisms such as algae and improved expression of heterologous genes.

SUMMARY

Provided herein are inducible novel algal promoter and terminator sequences for the inducible expression of native as well as heterologous DNA sequences in algal cells. Also provided are DNA constructs and expression cassettes comprising the inducible novel algal promoter and/or terminator sequences. Also provided are algal mutants comprising a DNA construct comprising the inducible novel algal promoter and/or terminator sequences. and methods of selectively expressing a DNA of interest in algal cells.

In one aspect, the disclosure provides inducible algal nitrate reductase and nitrite reductase promoter sequences comprising a nucleic acid sequence having at least 80%, at least 85%, at least 90%, at least 95%, at least 96%, at least 97%, at least 98%, or at least 99% or 100% sequence identity (but optionally in any embodiment less than 100% sequence identity) to at least 100, at least 200, at least 300, at least 400, or at least 500 contiguous nucleotides of a sequence, or to the full sequence, selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, and 51. For example, the promoter can comprise a sequence having at least 80%, at least 85%, at least 90%, at least 95%, at least 96%, at least 97%, at least 98%, or at least 99% (but optionally in any embodiment less than 100%) identity to at least 100, at least 200, at least 300, at least 400, or at least 500 contiguous nucleotides extending in the 5' direction from the 3' end (or, alternatively in the 3' direction from the 5' end) of a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, and 51. In another example the promoter can comprise at least 90% but less than 100% sequence identity to any of the named sequences, or to at least 500 contiguous nucleotides extending in the 5' direction from the 3' end. In some embodiments, the nitrate reductase and nitrite reductase promoters are located in the intergenic region between the nitrate reductase and nitrite reductase genes. In some embodiments, the nitrate and nitrite reductase promoters are located in the 5'-UTR regions of the nitrate and nitrite reductase genes, respectively.

In one aspect the disclosure provides algal nitrate reductase and nitrite reductase terminator sequences comprising a nucleic acid sequence having at least 80%, at least 85%, at least 90%, at least 95%, at least 96%, at least 97%, at least 98%, or at least 99% (but optionally, in any embodiment, less than 100%) identity to at least 25, at least 50, at least 75, at least 100, or at least 150 contiguous nucleotides of a sequence, or to the full length sequence, selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, and 52. In some embodiments, the nitrate and nitrite reductase terminators are located in the 3'-UTR regions of the nitrate and nitrite reductase genes, respectively.

In one aspect, the disclosure provides an isolated DNA molecule comprising an algal nitrate reductase or nitrite reductase inducible promoter operably linked to a DNA of interest encoding a polypeptide or functional RNA, wherein the DNA of interest encoding a polypeptide or functional RNA is not regulated by or operably linked to the promoter in nature. The algal nitrate reductase or nitrite reductase inducible promoter have at least 80%, at least 85%, at least 90%, at least 95%, at least 96%, at least 97%, at least 98%, or at least 99% sequence identity (and optionally in any embodiment less than 100% sequence identity) to at least 100, at least 200, at least 300, at least 400, or at least 500 contiguous nucleotides of a sequence (or to the full length sequence) selected from the group consisting SEQ ID NOs: 1, 3, 5, 7, 9, 11, 13, 15, 17, 19, 21, 23, 25, 27, 29, 31, 33, 35, 37, 39, 41, 43, 45, 47, 49, and 51. For example, the isolated DNA molecule can comprise a sequence having at least 80% at least 85%, at least 90%, at least 95%, at least 96%, at least 97%, at least 98%, or at least 99% (and optionally in any embodiment less than 100%) sequence identity to at least 100, at least 200, at least 300, at least 400, or at least 500 contiguous nucleotides (or to the full length sequence) extending in the 5' direction from the 3' end (or, alternatively in the 3' direction from the 5' end) of a sequence selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, and 51. The algal nitrate reductase or nitrite reductase promoters of the present application can be operably linked with any DNA of interest that is heterologous or homologous to the algal species. In case of a DNA of interest that is homologous to the algae, these promoters are not juxtaposed to these DNA of interest in nature and do not regulate the expression of these DNA interest in nature.

In some embodiments, the isolated DNA molecule comprises an algal nitrate reductase or nitrite reductase terminator sequences comprising a nucleic acid sequence having at least 80%, at least 85%, at least 90%, at least 95%, at least 96%, at least 97%, at least 98%, or at least 99% (and optionally in any embodiment less than 100%) sequence identity to at least 25, at least 50, at least 75, at least 100, or at least 150 contiguous nucleotides of a sequence (or to the full length sequence) selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, and 52 operably linked to the DNA of interest encoding the polypeptide or a functional RNA.

In one aspect provided herein are genetically engineered algae comprising a DNA molecule or sequence comprising an algal nitrate reductase or nitrite reductase inducible promoter operably linked to a DNA of interest, wherein the DNA of interest is not regulated by the promoter in Nature. In some embodiments the DNA molecule is integrated into the algal genome. The DNA of interest can be heterologous or homologous to the algal species. In case of a DNA of interest that is homologous to the algae, the promoter is not juxtaposed to the DNA of interest in nature and does not regulate the expression of the DNA of interest in Nature.

In one aspect provided herein are expression cassette comprising DNA molecule comprising an algal nitrate reductase or nitrite reductase inducible promoter operably linked to a DNA of interest encoding a polypeptide or a functional RNA, wherein the DNA of interest encoding the polypeptide or a functional RNA is not regulated by the promoter in nature, wherein the DNA of interest encodes (a) a protein associated with lipid biosynthesis, (b) a lipase, (c) a protein that participates in photosynthesis, (d) a protein associated with carbon fixation, (e) a transporter protein, (f) a dehydrogenase, (g) a transcription factor, (h) a transcriptional activator, (i) a cell signaling protein, (j) a metabolic enzyme, (k) a reporter protein, (l) a selectable marker, (m) a recombinase, n) an antisense sequence, (o) a shRNA, (p) an siRNA, (q) a gRNA, or (r) a ribozyme. In some embodiments, the expression cassette further comprises an algal nitrate reductase or nitrite reductase terminator sequence operably linked to the DNA of interest encoding the polypeptide or a functional RNA. The DNA of interest can be heterologous or homologous to the algal species. In case of a DNA of interest that is homologous to the algae, these promoters are not juxtaposed to these DNA of interest in nature and do not regulate the expression of these DNA interest in nature.

In one aspect provided herein are method of selectively expressing a DNA of interest in an algal cell comprising: a) transforming an algal cell with an isolated DNA molecule comprising an algal nitrate reductase or nitrite reductase inducible promoter operably linked to a DNA of interest encoding the DNA of interest in which the DNA of interest encoding the DNA of interest is not regulated by the promoter in nature to generate transformed algal cells, or any DNA molecule or sequence described herein; and b) growing the transformed algal cells in a media that selectively permits the expression of the DNA of interest in the algal cell. In some embodiments, the isolated DNA molecule is introduced by particle bombardment. In some embodiments, the isolated DNA molecule is introduced by electroporation. In some embodiments, the promoter sequence is a nitrite reductase, and wherein the algal cells are grown in a media comprising Nitrate, wherein the expression of the DNA of interest is induced. In some embodiments, the promoter sequence is a nitrite reductase, and wherein the algal cells are grown in a media comprising ammonium salt, wherein the expression of the DNA of interest is repressed.

In some embodiments of the above aspects, the algal nitrate reductase or nitrite reductase terminator is derived from the same species as the promoter. In some embodiments of the above aspects, the DNA of interest encoding a polypeptide or functional RNA is heterologous to the promoter sequence. In some embodiments of the above aspects, the DNA of interest encoding a polypeptide or functional RNA and the promoter are from the same algal species, wherein the DNA of interest encoding and the promoter are not juxtaposed to each other in nature.

In some embodiments of the above aspects, the DNA of interest encoding a polypeptide or functional RNA is genetically engineered to include at least one, at least two, at least three, at least four, at least five introns in which the introns are heterologous to the DNA of interest encoding a polypeptide or functional RNA. In some embodiments of the above aspects, the introns are derived from the same algal species as the promoter. In some embodiments of the above aspects, two or more heterologous introns, e.g., at least two, at least three, at least four, at least five introns can be derived from the same gene. In some embodiments of the above aspects, one or more introns and the promoter can be derived from the same gene.

In some embodiments of the above aspects, the DNA of interest encodes a functional RNA selected from the group consisting of an antisense sequence, a micro RNA, a shRNA, a siRNA, a gRNA, and a ribozyme.

In some embodiments of the above aspects, the promoter and the terminator are from the same gene. In some embodiments of the above aspects, the promoter and the terminator are from different genes.

In some embodiments of the above aspects, the DNA of interest encodes a (a) a protein associated with lipid biosynthesis, (b) a lipase, (c) a protein that participates in photosynthesis, (d) a protein associated with carbon fixation, (e) a transporter protein, (f) a dehydrogenase, (g) a transcription factor, (h) a transcriptional activator, (i) a cell signaling protein, (j) an enzyme, (k) a reporter protein, (l) a selectable marker, or (m) a recombinase. In some embodiments of the above aspects, the DNA of interest encodes Cre recombinase.

In some embodiments, the mutant algae belongs to a genus selected from any one or more of the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella,*

*Vischeria*, and *Volvox*. These genera are hereby disclosed in every possible combination and sub-combination as if set forth fully herein.

In some embodiments, of the above aspects, the inducible algal nitrate reductase or nitrite reductase promoter sequences is operably linked with the DNA of interest. In some embodiments, the expression of the DNA of interest operably linked with the nitrate reductase or nitrite reductase promoter sequences is increased in the presence of nitrate ion. In some embodiments, the expression of the DNA of interest operably linked with the nitrate reductase or nitrite reductase promoter sequences is repressed in the presence of ammonium ion.

In some embodiments, of the above aspects, algal nitrate reductase or nitrite reductase terminator sequences comprising a nucleic acid sequence having at least 80%, at least 85%, at least 90%, at least 95%, at least 96%, at least 97%, at least 98%, or at least 99% identity to at least 25, at least 50, at least 75, at least 100, or at least 150 contiguous nucleotides of a sequence selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, and 52. In some embodiments, of the above aspects, the algal nitrate reductase or nitrite reductase terminator sequence is operably linked with the DNA of interest.

In one aspect, the disclosure provides a vector comprising an expression cassette as disclosed herein and one or both of an autonomous replication sequence and a selectable marker gene. In some embodiments, the vector includes at least one origin of replication. In some embodiments, the vector further comprises an additional promoter, such as but not limited to a promoter as disclosed herein, operably linked to the selectable marker or reporter gene.

In some embodiments, the vector is for transformation of a eukaryotic cell, such as but not limited to a eukaryotic microalgal cell or phytoplankter cell, in which the vector includes a selectable marker gene operably linked to a promoter as provided herein, for example, a promoter that includes a nucleotide sequence having at least 80%, at least 85%, at least 90%, at least 95%, at least 96%, at least 97%, at least 98%, at least 99% sequence identity (and, optionally in any of the embodiments, less than 100% sequence identity) to at least 100, at least 200, at least 300, at least 400, at least 500, at least 600, at least 700, or at least 800 contiguous nucleotides (or to the full length sequence) of any of SEQ ID NOs:1, 3, 5, 7, 9, 11, 13, 15, 17, 19, 21, 23, 25, 27, 29, 31, 33, 35, 37, 39, 41, 43, 45, 47, 49, or 51. The transformation vector can further include one or more additional genes or constructs for transfer into the host cell, such as a gene encoding a polypeptide such as but not limited to any disclosed hereinabove or a construct encoding a functional RNA, where the gene encoding a polypeptide or functional RNA can optionally be operably linked to a promoter as described herein, or can optionally be operably linked to another promoter.

Additionally, or alternatively, the vectors as provided herein may comprise a terminator as provided herein. For example, a vector of the present invention may comprise a nucleotide sequence having at least 80%, at least 85%, at least 90%, at least 95%, at least 96%, at least 97%, at least 98%, at least 99% sequence identity (and optionally in any embodiment less than 100% sequence identity) to at least 100, at least 200, at least 300, at least 400, at least 500, at least 600, at least 700, or at least 800 contiguous nucleotides (or to the full length sequence) of any of SEQ ID NOs: 2, 4, 6, 8, 10, 12, 14, 16, 18, 20, 22, 24, 26, 28, 30, 32, 34, 36, 38, 40, 42, 44, 46, 48, 50, or 52. A DNA of interest or a selectable marker gene on a vector of the present invention may be operably linked to a terminator sequence as provided herein.

In some embodiments, a selectable marker gene is selected from the group consisting of a gene conferring resistance to an antibiotic (e.g., tetracycline, doxycyclin, or analogs thereof, puromycin, hygromycin, blasticidin, bleomycin or phleomycin (Zeocin™) nourseothricin), a gene conferring resistance to an herbicide, a gene encoding acetyl CoA carboxylase (ACCase), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS (aroA), a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acteyl transferase, a gene encoding phytoene desaturase, a gene encoding prenyl transferase, a gene encoding protoporphyrin oxidase, a gene encoding superoxide dismutase, arg7, his3, hisD, hisG, manA, nit1, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene, or an R-locus gene. A detectable marker gene can be, for example, a tyrosinase gene, lacZ, an alkaline phosphatase gene, an α-amylase gene, a horseradish peroxidase gene, an α-galactosidase gene, a luciferin/luciferase gene, a beta-glucuronidase gene (GUS), or a gene encoding a fluorescent protein.

BRIEF DESCRIPTION OF THE DRAWINGS

The drawings described herein are for illustrative purposes only of selected embodiments and not all possible implementations and are not intended to limit the scope of the present disclosure.

FIG. 4 also shows the nitrite reductase terminator at the 3'-UTR region of the nitrite reductase gene.

DETAILED DESCRIPTION

Figure 4:
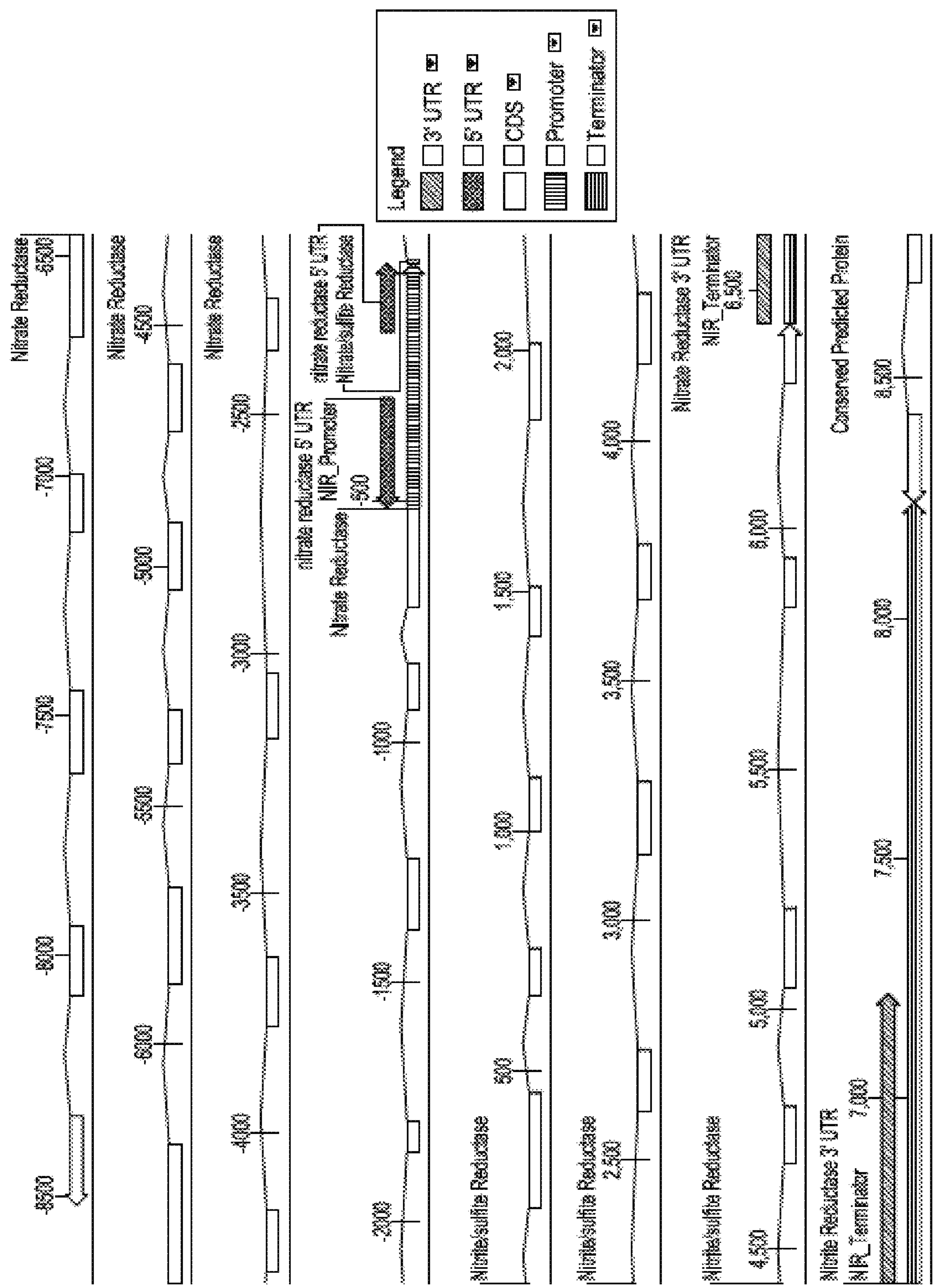
FIG. 4 shows a schematics of coding sequences of the *Parachlorella* nitrate and nitrite reductase genes and the intergenic untranslated regions between the two genes comprising the nitrate and nitrite reductase promoter sequences, respectively in opposite orientations.

The present application identifies novel algal nitrate and nitrite/sulfite reductase promoter and terminator sequences in the 5'- and 3'-untranslated regions (UTR) of the algal nitrate reductase and nitrite reductase genes based on the RNA sequencing data, Hidden Markov Model analysis, BLAST analysis, and Pfam analysis of Pfam PF01077 and PF03460. In some embodiments, the nitrite reductase and nitrite reductase genes are on the opposite orientations of the same chromosome of algae. In some embodiments, the nitrite reductase and nitrite reductase promoters are located in the intergenic regions of the two genes (FIG. 4). In some embodiments, the nitrite reductase and nitrite reductase terminators are located in the 3'-UTR regions of the nitrite reductase and nitrite reductase genes, respectively (FIG. 4).

The present application discloses several novel inducible algal nitrate reductase or nitrite/sulfite reductase promoter sequences from various algal groups e.g., *Parachlorella, Oocystis, Picochlorum*, and *Tetraselmis*. Non-limiting examples of such algal nitrate reductase or nitrite/sulfite reductase promoter sequences are listed as SEQ ID NOs: 1, 3, 5, 7, 9, 11, 13, 15, 17, 19, 21, 23, 25, 27, 29, 31, 33, 35, 37, 39, 41, 43, 45, 47, 49, and 51 and shown below.

The present application discloses several novel algal nitrate reductase or nitrite reductase terminator sequences from various algal groups e.g., *Parachlorella, Oocystis, Picochlorum*, and *Tetraselmis*. Non-limiting examples of such algal nitrate reductase or nitrite/sulfite reductase terminator sequences are listed as SEQ ID NOs: 2, 4, 6, 8, 10, 12, 14, 16, 18, 20, 22, 24, 26, 28, 30, 32, 34, 36, 38, 40, 42, 44, 46, 48, 50, and 52 and shown below.

The present application also discloses DNA constructs comprising a novel inducible algal nitrate reductase or nitrite reductase promoter sequence described herein operably linked to a DNA of interest encoding a polypeptide or functional RNA in which the DNA of interest encodes a polypeptide or functional RNA that is not regulated by or operably linked to the promoter in Nature (e.g. in wild-type organisms). In some embodiments the promoter can be a heterologous promoter. In some embodiments, the DNA construct also comprises algal nitrate reductase or nitrite reductase terminator sequences that are operably linked to the DNA of interest. The present application also discloses expression vectors comprising the DNA construct. Whether a control sequence regulates a nucleic acid sequence in Nature can be determined by whether the control sequence regulates the nucleic acid sequence in a wild-type organism.

The present application also discloses methods for selectively expressing a DNA of interest in algae using the novel inducible algal nitrate reductase or nitrite reductase promoter sequences that are operably linked to the DNA of interest. The genetically engineered algae comprising the novel inducible algal nitrate reductase or nitrite reductase promoter operably linked to the DNA of interest are grown in selective media (e.g., media comprising nitrate) to induce or the expression of the DNA of interest or the genetically engineered algae can be grown in a media comprising ammonium ion to repress the expression of the DNA of interest.

Listed below are the exemplary novel algal nitrate reductase or nitrite reductase promoter and terminator sequences from various algal species.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a molecule" includes one or more molecules, including mixtures thereof. "A and/or B" is used herein to include all of the following alternatives: "A", "B", and "A and B".

As used herein, the terms "about" or "approximately" when referring to any numerical value are intended to mean a value of plus or minus 10% of the stated value. For example, "about 50 degrees C." (or "approximately 50 degrees C.") encompasses a range of temperatures from 45 degrees C. to 55 degrees C., inclusive. Similarly, "about 100 mM" (or "approximately 100 mM") encompasses a range of concentrations from 90 mM to 110 mM, inclusive. Alternatively, "about" or "approximately" can mean within 5% of the stated value, or in some cases within 2.5% of the stated value, or, "about" can mean rounded to the nearest significant digit. All ranges provided within the application are inclusive of the values of the upper and lower ends of the range.

The terms, "cells", "cell cultures", "cell line", "recombinant host cells", "recipient cells" and "host cells" as used herein, include the primary subject cells and any progeny thereof, without regard to the number of transfers. It should be understood that not all progeny are exactly identical to the parental cell (due to deliberate or inadvertent mutations or differences in the environment); however, such altered progeny are included in these terms, so long as the progeny retain the same functionality as that of the originally transformed cell.

As used herein, the term "construct" is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a nucleic acid molecule where one or more nucleic acid sequences have been linked in a functionally operative manner, i.e. operably linked.

A "control organism", "control microorganism", or "control cell" as used herein, refers to an organism, microorganism, or cell that is substantially identical to the subject organism, microorganism, or cell, except for the engineered genetic manipulation or introduced mutation disclosed for the subject organism, microorganism, or cell, and can provide a reference point for measuring changes in phenotype of the subject organism or cell. "Substantially identical" thus includes, for example, small random variations in genome sequence ("SNPs") that are not relevant to the genotype, phenotype, parameter, or gene expression level that is of interest in the subject microorganism. Depending on specific purposes of their use, a control organism or cell may comprise, for example, (a) a progenitor strain or species, cell or microorganism population, or organism, with respect to the subject organism, microorganism, or cell, where the progenitor lacks the genetically engineered constructs or alterations that were introduced into the progenitor strain, species, organism, or cell or microorganism population to generate the subject organism, microorganism, or cell; b) a wild-type organism or cell, i.e., of the same genotype as the starting material for the genetic alteration which resulted in the subject organism or cell; (c) an organism or cell of the same genotype as the starting material but which has been transformed with a null construct (i.e. a construct which has no known effect on the trait of interest, such as a construct comprising a reporter gene); (d) an organism or cell which is a non-transformed segregant among progeny of a subject organism, microorganism, or cell; or (e) the subject organism or cell itself, under conditions in which the gene of interest is not expressed. In some instances, "control organism" may refer to an organism that does not contain the exogenous nucleic acid present in the transgenic organism of interest, but otherwise has the same or very similar genetic background as such a transgenic organism.

As used herein, "genetically engineered" algae refer to a non-naturally occurring recombinant algal cell that has altered nucleotide composition of its genome, or altered expression of a gene, including overexpression or repression of expression of a gene under different temporal, biological, or environmental regulation and/or to a different degree than that occurs naturally and/or expression of a gene that is not naturally expressed in the recombinant cell. The altered nucleotide composition (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. For example, a genetically engineered algae having altered expression of a gene as disclosed herein can have an altered nucleotide composition, which can be one or more nucleobase changes and/or one or more nucleobase deletions and/or one or more nucleobase insertions, into the region of a gene 5' of the transcriptional start site, such as, in non-limiting examples, within 2 kb, within 1.5 kb, within 1 kb, or within 0.5 kb of the known or putative transcriptional start site, or within 3 kb, within 2.5 kb, within 2 kb, within 1.5 kb, within 1 kb, or within 0.5 kb of the translational start site. Genetically engineered algal cells are algal cells may be manipulated by introduction of a heterologous or exogenous (e.g., non-native) recombinant nucleic acid sequence into the organism, and includes, without limitation, gene knockouts, targeted mutations, and gene replacement, promoter replacement, deletion, or insertion, or transfer of a nucleic acid molecule, e.g., a transgene, synthetic gene, promoter, or other sequence into the organism. Genetically engineered algal cells also includes the progeny of the genetically engineered parental cells.

The term "expression cassette" as used herein, refers to a nucleic acid construct that encodes a protein or functional RNA operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

A "functional RNA molecule" is an RNA molecule that can interact with one or more proteins or nucleic acid molecules to perform or participate in a structural, catalytic, or regulatory function that affects the expression or activity of a gene or gene product other than the gene that produced the functional RNA. A functional RNA can be, for example, a transfer RNA (tRNA), ribosomal RNA (rRNA), anti-sense RNA (asRNA), microRNA (miRNA), short-hairpin RNA (shRNA), small interfering RNA (siRNA), a guide RNA (gRNA), CRISPR RNA (crRNA), or transactivating RNA (tracrRNA) of a CRISPR system, small nucleolar RNAs (snoRNAs), piwi-interacting RNA (piRNA), or a ribozyme.

The term "DNA of interest" is used broadly to refer to any segment of a DNA molecule encoding a polypeptide or expressed RNA. Thus, DNA of interest include sequences encoding expressed RNA which can include polypeptide coding sequences or, for example, functional RNAs. DNA of interest may further comprise regulatory sequences required for or affecting their expression, as well as sequences associated with the protein or RNA-encoding sequence in its natural state, such as, for example, intron sequences, 5' or 3' untranslated sequences, etc. In some examples, a DNA of interest may only refer to a protein-encoding portion of a DNA or RNA molecule, which may or may not include introns. The DNA of interest may optionally comprise heterologous introns, i.e., introns that are not native to the gene from which the protein or functional RNA-encoding sequences are derived. A DNA of interest is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. DNA of interest can be obtained from a variety of sources, including cloning from a source of interest or synthesizing from known or predicted sequence information.

Non-limiting examples of proteins encoded by DNA of interest include a protein associated with lipid biosynthesis a lipase, a protein that participates in photosynthesis, a protein associated with carbon fixation, a transporter protein, a dehydrogenase, a transcription factor, a transcriptional activator, a cell signaling protein, an enzyme, a reporter protein, a selectable marker, and a recombinase.

Non-limiting examples of proteins associated with lipid biosynthesis, a protein associated with carbon fixation and/or photosynthesis include those described in US Application publication 20140220638, US Application publication 20160304896, US Application publication 2017005830303, US Application publication 20180186842. Each of these patent application publications is incorporated herein by reference in its entirety.

Non-limiting examples of enzymes include recombinase, e.g., Cre (NCBI Protein database accession numbers: YP_006472.1, WP_063075144, WP_052200029.1), CRISPR Cas9 (NCBI Protein database accession number WP_117329810).

One exemplary nucleic acid sequence of Cre recombinase comprising N-terminal nuclear localization signal and six *Parachlorella* nitrite reductase introns is shown below.

Non-limiting examples of reporter protein include (NCBI Protein database accession number: YP_002302326.1). One exemplary sequence of Cre recombinase is shown below.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

A DNA molecule may be "derived from" an indicated source, which includes the isolation (in whole or in part) of a nucleic acid segment from an indicated source. A DNA molecule may also be derived from an indicated source by, for example, direct cloning, PCR amplification, or artificial synthesis from the indicated polynucleotide source or based on a sequence associated with the indicated polynucleotide source. The DNA molecule may be part of the algal genome or can be an exogenous DNA sequence. The DNA molecule can be exogenous DNA integrated into the algal genome. The DNA molecule may comprise one or more genes, 5'- and 3'-untranslated regions (UTR). In some embodiments, the 5'- or 3'-UTR may comprise one or more regulatory elements.

DNA molecules or DNA of interest that may be derived from a particular source or species also include genes or nucleic acid molecules having sequence modifications with respect to the source nucleic acid molecules. For example, a DNA molecules or DNA of interest derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis, or any combination thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild-type" refer to a form found in nature. For example, a naturally occurring or wild-type nucleic acid molecule, nucleotide sequence or protein may be present in an isolated from a natural source, and is not intentionally modified by human manipulation.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, a shRNA, a ribozyme, etc.), of an expressed gene. The term "increased expression" includes an alteration in gene expression to facilitate increased mRNA production and/or increased polypeptide expression. "Increased production", when referring to protein abundance or the abundance of active protein resulting from gene expression, protein turnover rates, protein activation states, and the like, includes an increase in the amount of polypeptide expression, in the level of the enzymatic activity of a polypeptide, or a combination of both, as compared to the native production or enzymatic activity of the polypeptide.

As used herein, the term "expression of the DNA of interest is induced" refers to a selective increase in expression of the DNA of interest under a given condition as compared to the expression of the DNA of interest in the absence of such condition. For example, when the algae comprising the DNA of interest that is regulated by algal nitrite reductase promoter is grown in a media comprising nitrate ion, the expression of the DNA of interest is increased as compared to a the level of expression of the DNA of interest when the algae is grown in a media in the absence of nitrate ions.

As used herein, the term "expression of the DNA of interest is repressed" refers to decrease in expression of the DNA of interest under a given condition as compared to the expression of the DNA of interest in the absence of such condition. For example, when the algae comprising the DNA of interest that is regulated by algal nitrite reductase promoter is grown in a media comprising ammonium ion, the expression of the DNA of interest is decreased as compared to a the level of expression of the DNA of interest when the algae is grown in a media in the absence of ammonium ions.

Further, the term "exogenous" as used herein in the context of a gene or protein, refers to a gene or protein that is not derived from the host organism species.

The term "transgene" as used herein, refers to an exogenous gene, that is, a gene introduced into a microorganism or a progenitor by human intervention.

The term "ortholog" of a gene or protein as used herein refers to its functional equivalent in another species.

Gene and protein Accession numbers, commonly provided herein in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present disclosure, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host alga operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

The term "heterologous" when used in reference to a polynucleotide, a gene, a nucleic acid, a polypeptide, or an enzyme, refers to a polynucleotide, gene, a nucleic acid, polypeptide, or an enzyme that is not derived from the host species. For example, "heterologous gene" or "heterologous nucleic acid sequence" as used herein, refers to a gene or nucleic acid sequence from a different species than the species of the host organism it is introduced into. When referring to a gene regulatory sequence or to an auxiliary nucleic acid sequence used for manipulating expression of a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome, chromosome or episome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. An intron inserted into a gene that it is not associated with in nature (for example, an intron derived from a different gene) is referred to herein as a "heterologous intron," even though the promoter may be derived from the same species (or, in some cases, the same organism) as the gene into which it is engineered. Similarly, when referring to a protein localization sequence or protein domain of an engineered protein, "heterologous" means that the localization sequence or protein domain is derived from a protein different from that into which it is incorporated by genetic engineering.

"Regulatory sequence", "regulatory element", or "regulatory element sequence" refers to a nucleotide sequence located upstream (5'), within, or downstream (3') of a coding sequence. Transcription of the coding sequence and/or translation of an RNA molecule resulting from transcription of the coding sequence are typically affected by the presence or absence of the regulatory sequence. These regulatory element sequences may comprise promoters, cis-elements, enhancers, terminators, or introns. Regulatory elements may be isolated or identified from UnTranslated Regions (UTRs) from a particular polynucleotide sequence. Any of the regulatory elements described herein may be present in a chimeric or hybrid regulatory expression element. Any of the regulatory elements described herein may be present in a recombinant construct of the present invention.

The terms "promoter", "promoter region", or "promoter sequence" refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked transcribable polynucleotide molecule, e.g., a coding sequence. Promoters may contain, in addition to sequences recognized by RNA polymerase and, preferably, other transcription factors, regulatory sequence elements such as cis-elements or enhancer domains that affect the transcription of operably linked genes. An "algal promoter" is a native or non-native promoter that is functional in algal cells.

The term "operably linked," as used herein, denotes a configuration in which a control sequence is placed at an appropriate position relative to the coding sequence of a polynucleotide sequence such that the control sequence directs or regulates the expression of the coding sequence of a polypeptide and/or functional RNA. Thus, a promoter is in operable linkage with a nucleic acid sequence if it can mediate transcription of the nucleic acid sequence. A terminator is in operable linkage with a nucleic acid sequence if it can mediate termination of transcription of the sequence. When introduced into a host cell, an expression cassette can result in transcription and/or translation of an encoded RNA or polypeptide under appropriate conditions. Antisense or sense constructs that are not or cannot be translated are not excluded by this definition. In the case of both expression of transgenes and suppression of endogenous genes (e.g., by antisense or RNAi) one of ordinary skill will recognize that the inserted polynucleotide sequence need not be identical, but maybe only substantially identical to a sequence of the gene from which it was derived. As explained herein, these substantially identical variants are specifically covered by reference to a specific nucleic acid sequence. When a control sequence (e.g. promoter or terminator) regulates transcription or termination of transcription of a nucleic acid sequence it is operably linked to the sequence it regulates.

The term "selectable marker" or "selectable marker gene" as used herein includes any gene that confers a phenotype on a cell in which it is expressed to facilitate the selection of cells that are transfected or transformed with a nucleic acid construct of the invention. The term may also be used to refer to gene products that effectuate said phenotypes. Non-limiting examples of selectable markers include: 1) genes conferring resistance to antibiotics such as amikacin (aphA6), ampicillin (ampR), blasticidin (bls, bsr, bsd), bleomicin or phleomycin (ZEOCIN™) (ble), chloramphenicol (cat), emetine (RBS14p or cryl-1), erythromycin (ermE), G418 (GENETICIN™) (neo), gentamycin (aac3 or aacC4), hygromycin B (aphlV, hph, hpt), kanamycin (nptII), methotrexate (DHFR mtxR), penicillin and other β-lactams (β-lactamases), streptomycin or spectinomycin (aadA, spec/strep), and tetracycline (tetA, tetM, tetQ); 2) genes conferring tolerance to herbicides such as aminotriazole, amitrole, andrimid, aryloxyphenoxy propionates, atrazines, bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, or urea; acetyl CoA carboxylase (ACCase); acetohydroxy acid synthase (ahas); acetolactate synthase (als, csrl-1, csrl-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acteyl transferase (pat, bar), phytoene desaturase (crtl), prenyl transferase, protoporphyrin oxidase, the psbA photosystem II polypeptide (psbA), and SMM esterase (SulE) superoxide dismutase (sod); 3) genes that may be used in auxotrophic strains or to confer other metabolic effects, such as arg7, his3, hisD, hisG, lysA, manA, metE, nitl, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

A “reporter gene” is a gene encoding a protein that is detectable or has an activity that produces a detectable product. A reporter gene can encode a visual marker or enzyme that produces a detectable signal, such as cat, lacZ, uidA, xylE, an alkaline phosphatase gene, an α-amylase gene, an α-galactosidase gene, a β-glucuronidase gene, a β-lactamase gene, a horseradish peroxidase gene, a luciferin/luciferase gene, an R-locus gene, a tyrosinase gene, or a gene encoding a fluorescent protein, including but not limited to a blue, cyan, green, red, or yellow fluorescent protein, a photoconvertible, photoswitchable, or optical highlighter fluorescent protein, or any of variant thereof, including, without limitation, codon-optimized, rapidly folding, monomeric, increased stability, and enhanced fluorescence variants.

The term “terminator” or “terminator sequence” or “transcription terminator” as used herein refers to a regulatory section of genetic sequence that ordinarily signals RNA polymerase to cease transcription in the usual manner. The terminator can normally mark the end of a gene, coding sequence, or operon in DNA.

The term “transformation” as used herein refers to the introduction of one or more exogenous nucleic acid sequences or polynucleotides into a host cell or organism by using one or more physical, chemical, or biological methods. Physical and chemical methods of transformation (i.e., “transfection”) include, by way of non-limiting example, electroporation, particle bombardment, and liposome delivery. Biological methods of transformation (i.e., “transduction”) include the transfer of DNA using engineered viruses or microbes (e.g., Agrobacterium).

The term “intron” is used herein to refer to a nucleotide sequence within a gene that is removed from the RNA transcribed from the gene by RNA splicing. (The term intron is used to refer to the RNA sequence as it occurs in RNA molecules prior to splicing as well as to the DNA sequence as it occurs in the gene.) The introns disclosed herein are “spliceosomal introns” that occur naturally in the nuclear genes of eukaryotes and are spliced out by the splicing machinery (spliceosome) of eukaryotic cells. Also considered are introns derived from naturally-occurring introns, e.g., introns at least 65%, 70%, 75%, 80%, 85%, 90%, 95%, 96%. 97%, 98%, or 99% identical to the sequence of a naturally-occurring intron or an internally deleted variant thereof, for example, a variant having from 1 to 1000 bp deleted from within the borders of the intron. Also considered are chimeric introns that comprise intron sequences of two or more naturally-occurring introns. Introns include a GT (GU in the primary RNA transcript) at the 5' end, a branch site sequence near the 3' end of the intron, and an AG acceptor site at the 3' end of the intron. The surrounding exon sequence includes a GG at the 5' border with the intron, and a G after the AG at the 3' end of the intron. Such sequences can optionally be engineered into the coding sequences of a gene as provided herein at the site of intron insertion.

An intronylated gene as provided herein is engineered to include at least one heterologous intron, that is, at least one intron that does not naturally occur in the gene that encodes the polypeptide encoded by the engineered gene, and an intronylated gene in some embodiments is preferably engineered to include at least three, at least four, or at least five heterologous introns, that is, at least three, at least four, or at least five introns that do not naturally occur in the gene. For example, amino acid-encoding sequences of the engineered gene can encode a polypeptide that is not encoded by the gene from which the heterologous introns are derived. The heterologous introns are inserted into a gene that they do not occur in naturally, for example, using genetic engineering or gene synthesis techniques. The amino acid-encoding sequences of the engineered gene may optionally be altered for example to generate sequences immediately proximal to a heterologous intron to allow for correct splicing of the introduced intron and/or to alter the codon usage (for example, to reflect a codon preference of the host) and/or to introduce a mutation. In some embodiments, the at least three heterologous introns are derived from one or more genes other than the gene from which the amino acid-encoding sequences of the engineered gene are derived, for example, the at least three exogenous introns can be derived from naturally-occurring introns. In various embodiments, the at least three, at least four, or at least five exogenous introns can be naturally-occurring introns from another gene of the same or different organism from which the amino acid encoding sequences of the engineered gene are derived, or can be derived from naturally-occurring introns from another gene of the same or different organism from which the amino acid encoding sequences of the engineered gene, for example, by one or more sequence modifications or internal deletion of sequences from the naturally-occurring intron(s). In some embodiments, the at least three, at least four, or at least five exogenous introns inserted into an engineered gene are all naturally-occurring introns of the same gene, and in some embodiments multiple introns of the same naturally-occurring gene may be introduced into the engineered gene in the same order in which they occur in the naturally-occurring gene from which they are derived. In some embodiments, the engineered gene is operably linked to a promoter, and the promoter and exogenous introns can optionally be derived from the same organism. In some embodiments, the engineered gene is operably linked to a promoter and a terminator, and the promoter, terminator, and exogenous introns can all be derived from the same organism and can all be derived from the same gene. Further, in various embodiments the amino acid-encoding sequences of the engineered gene can be codon-optimized, and in some examples can be codon optimized for expression in an organism from which the exogenous introns are derived.

Expression Cassettes

Expression cassettes disclosed herein comprise one or more regulatory elements as described herein to drive the expression of DNA of interest. These cassettes a DNA molecule that include any one of the algal nitrate reductase or nitrite reductase promoters sequences described herein operably linked to a DNA of interest, wherein the DNA of interest is positioned downstream of the promoter sequence, and optionally with any one of the algal nitrate reductase or nitrite reductase terminator sequences described herein or any combination thereof operably linked downstream of the DNA of interest. The algal nitrate reductase and nitrite reductase promoters of the invention can be used with any heterologous or homologous DNA of interest. In case of homologous genes, these promoters are not juxtaposed to these homologous genes of interest in nature. Thus, the algal nitrate reductase and nitrite reductase promoters do not regulate the expression of these homologous genes of interest in nature. The DNA of interest may optionally comprise heterologous introns, i.e., introns that are not native to the gene from which the protein or functional RNA-encoding sequences are derived. In some embodiments expression cassettes can be integrated into the genome of the algal cell or organism. In some embodiments integration occurs through transformation of the cell or organism.

The basic techniques for operably linking two or more sequences of DNA together are familiar to the skilled worker, and such methods have been described in a number of texts for standard molecular biological manipulation (see, e.g., "Molecular Cloning: A Laboratory Manual," 2nd ed. Cold Spring Harbor Laboratory Press, Cold Spring Harbor, N.Y.; Gibson et al. (2009) Nature Methods 6:343-345).

Vectors

The present invention also provides vectors that can comprise the regulatory elements and/or expression cassettes described herein. The vectors can further optionally comprise at least one origin of replication ("ORI") sequence for replication in a cell. The vectors may further optionally comprise one or more selectable markers under the control of one or more eukaryotic promoters, one or more selectable markers under the control of one or more prokaryotic promoters, and/or one or more sequences that mediate recombination of an exogenous nucleic acid sequence into the target cell's genome. In some embodiments vectors can be integrated into the genome of the algal cell or organism. In some embodiments the integration occurs through transformation of the cell or organism.

Additionally, a vector described herein may also comprise a selectable marker as described above.

The selectable marker gene can be operably linked to and/or under the control of a promoter as provided herein. The promoter regulating expression of the selectable marker may be conditional or inducible but is preferably constitutive, and can be, for example, any promoter disclosed herein or another promoter. Alternatively, the selectable marker may be placed under the control of the expression cassette promoter. If a selectable marker is placed under the control of the expression cassette promoter, the selectable marker and the expression cassette may be operably linked with an internal ribosome entry site ("IRES") element between the expression cassette and the selectable marker (Komar & Hatzoglou (2011) Cell Cycle 10:229-240 and Hellen & Sarnow (2001) Genes & Dev. 15:1593-1612, incorporated by reference in their entireties) or a "2A" sequence (Kim et al. (2011) PLoS One 6(4):e18556, incorporated by reference in its entirety).

Transformation Methods

The present invention also provides transformation methods in which a eukaryotic cell is transformed with an expression vector as described herein. The methods comprise introducing an expression vector as provided herein that includes at least one promoter or DNA sequence as provided herein and then selecting for a transformant. The expression vector may be introduced by many methods familiar to those skilled in the art including those described in U.S. Pat. No. 10,041,079 and US Patent application publication 2017/0073695, which are incorporated herein by reference in their entirety.

The algal cell can be a green alga, such as an algal cell of a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria*, and *Volvox*. For example, the eukaryotic cell transformed using the methods provided herein can optionally be a species of *Parachlorella*, such as non-limiting examples: *Parachlorella kessieri, P. hussii, P. beijerinckii*, P. sp. CCAP 206/1, or P. sp. pgu003.

In other embodiments the algal cell can be any eukaryotic microoalga such as, but not limited to, a Chlorophyte, an Ochrophyte, or a Charophyte alga. In some embodiments the alga can be a Chlorophyte alga of the taxonomic Class Chlorophyceace, or of the Class Chlorodendrophyceae, or the Class Prasinophyceace, or the Class Trebouxiophyceae, or the Class Eustigmatophyceae. In some embodiments, the alga can be a member of the Class Chlorophyceace, such as a species of any one or more of the genera *Asteromonas, Ankistrodesmus, Carteria, Chlamydomonas, Chlorococcum, Chlorogonium, Chlorodendrales, Chloroellales, Chrysosphaera, Dunaliella, Haematococcus, Monoraphidium, Neochloris, Oedogonium, Pelagomonas, Pleurococcus, Pyrobotrys, Scenedesmus*, or *Volvox*. In other embodiments, the alga can be a member of the Class Chlorodendrophyceae, such as a species of any one or more of the genera *Prasinocladus, Scherffelia*, or *Tetraselmis*. In further alternative embodiments, the alga can be a member of the Class Prasinophyceace, optionally a species of any one or more of the genera *Ostreococcus* or *Micromonas*. Further alternatively, the alga can be a member of the Class Trebouxiophyceae, and optionally of the Order Chlorellales, and optionally a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus*, or *Viridiella*, or any of all possible combinations or subcombination of the genera. In another embodiment the alga is a Chlorophyte alga of the Class Trebouxiophyceae, the Order Chlorellales, the Family Oocystaceae, Chlorellaceae, or Eustigmatophyceae, and optionally a genera selected from one or more of *Oocystis, Parachlorella, Picochlorum, Nannochloropsis*, and *Tetraselmis*. The alga can also be from the genus *Oocystis*, or the genus *Parachlorella*, or the genus *Picochlorum*, or the genus *Tetraselmis*, or from any of all possible combinations and sub-combinations of the genera disclosed. Any of the alga described herein can comprise a DNA molecule or sequence of the invention, such as comprising the algal nitrate reductase or nitrite reductase promoter operably linked to a DNA of interest, as described herein.

Culture

Transformed algal cell cultures can be diluted, plated on agar, and allowed to grow until isolated colonies can be selected for further propagation as clonal strains.

Transformed algal cell can be cultured in an inducing medium (IM) such as in the presence of nitrate ion or a nitrite ion such that the expression the DNA of interest is induced. The transformed algal cell can also be cultured in a repressive medium (RM) such as in the presence of ammonium salt such that the expression the DNA of interest is repressed.

Additionally, a photosynthetic organism can be cultured mixotrophically, in which the organism is grown in the presence of light for at least a part of the day, and also provided with one or more sources of reduced carbon. The photosynthetic organism can be grown mixotrophically for a period of time, followed by a period of phototrophic growth, or vice versa.

Media for phototrophic or mixotrophic growth of algae are known in the art, and media can be optimized to enhance growth or production of fatty acid products for a particular species. Artificial light sources can be used as the sole light source or to enhance or extend natural light.

The growth of algae can be in open areas, such as, for example, ponds, canals, channels, raceways, or tanks, or can be in bioreactors. Bioreactors are preferred for mixotrophic growth, and can also be used for phototrophic growth. The bioreactors can be of any sizes and form, and can include inlets for providing nutrients, additives, or gases, such as but not limited to air or $CO_2$. A bioreactor preferably also has an outlet for a sampling of the culture. A bioreactor can be configured such that the algal culture is mixed during the growth period, for example, by stirring, rocking, shaking, inverting, bubbling of gases through the culture, etc. Outdoor ponds, raceways, tanks, canals, etc. can also be designed for mixing of cultures through, for example, paddles, pumps, hoses or jets for circulation of the culture media, or tubes, hoses or inlets for supplying air or $CO_2$ to the culture.

EXAMPLES

Example 1

Identification of *Parachlorella* Regulatory Sequences

Multiple sequences were evaluated for their ability to function as promoters or terminators. Intergenic untranslated nucleic acid sequences flanking nitrate reductase and nitrite reductase genes based on a genome assembly for the wild-type *Parachlorella* strain WT-1185, RNA sequencing data, Hidden Markov Model analysis, BLAST analysis, and Pfam analysis of Pfam PF01077 and PF03460 were examined for promoter sequences.

Figure 3:
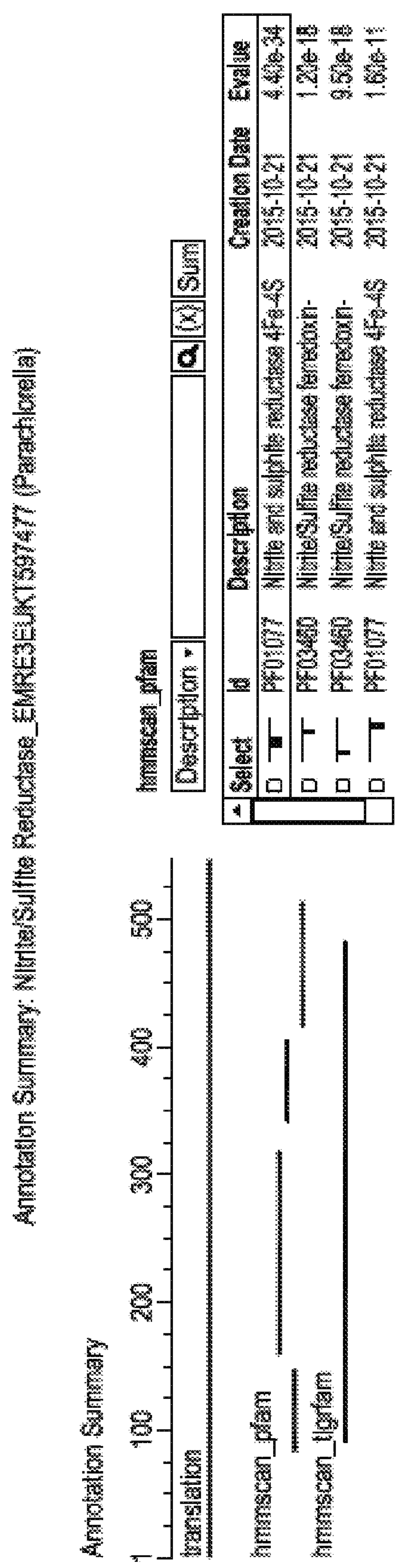
FIG. 3 shows the results of the Blast Alignments for the Nitrite/Sulfite reductase gene in *Parachlorella*. The results show that the top Pfam hits are all nitrite/sulfite reductase genes.

Blast alignments for *Parachlorella* show that the top Pfam hits (PF 01077 and PF 03460) are all nitrite/sulfite reductase genes (FIG. 3). The nitrite reductase and nitrate reductase genes in *Parachlorella* strain WT-1185 are in opposite orientations in the same chromosome (FIG. 4). The nitrite reductase and nitrite reductase promoters were identified in the intergenic regions of the nitrite reductase and nitrate reductase genes (FIG. 4). The nitrite reductase and nitrite reductase terminators were identified in the 3'-UTR regions of the nitrite reductase and nitrite reductase genes, respectively (FIG. 4).

Example 2

Generation of Expression Cassette

Figure 5:
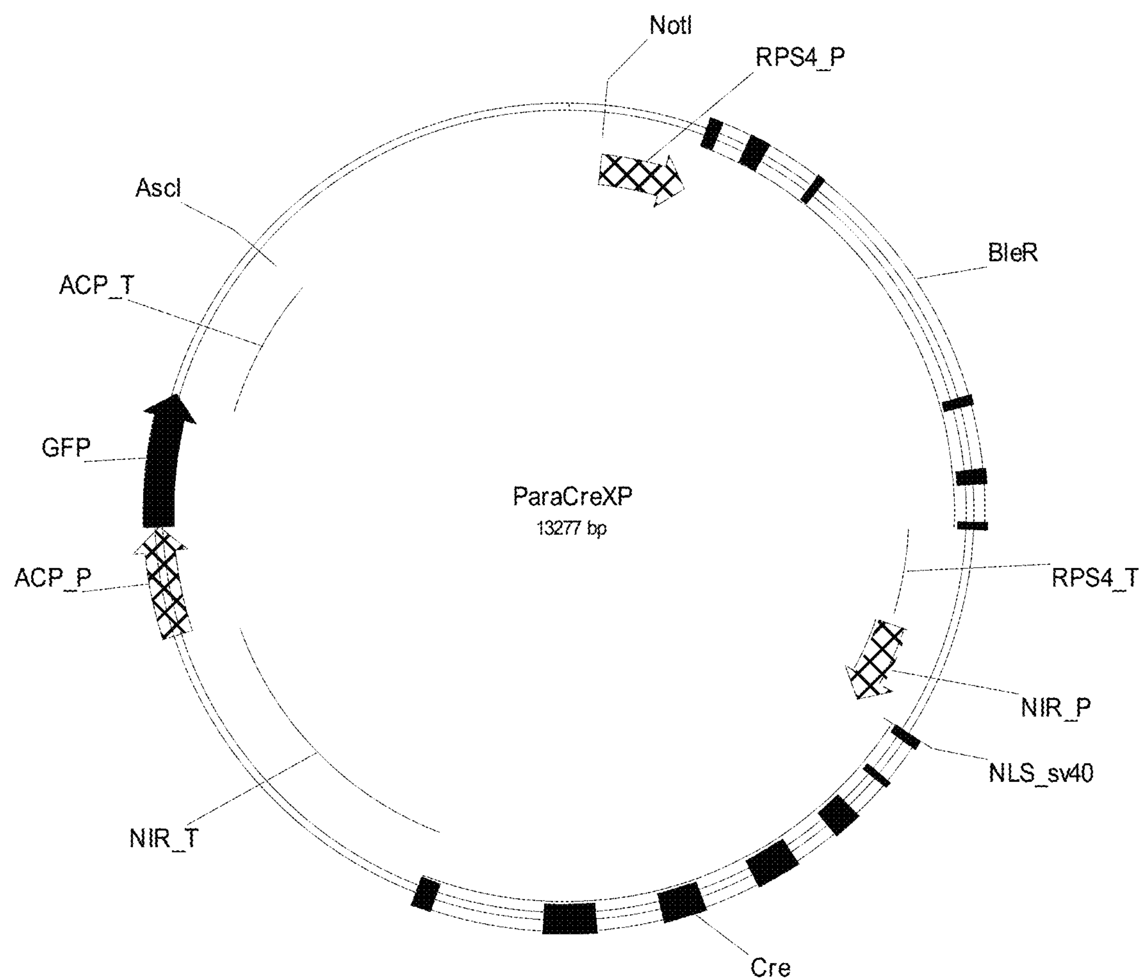
FIG. 5 shows a plasmid map of plasmid pSGE06785 that was used to express Cre recombinase (containing native *Parachlorella* introns) in the absence of ammonium by using the nitrite reductase promoter/terminator. Expression of the BleR and GFP gene is driven by constitutive promoters/terminators.

A ParaCreXP vector construct was used in the successful generation of a *Parachlorella* recombinant strain (FIG. 5). The vector construct comprised expression cassettes for the selectable marker bleomycin (Ble), Cre recombinase, and TurboGFP. The Ble and Cre genes were optimized for *Parachlorella* codon usage, whereas TurboGFP was directly amplified from pTurboGFP-C purchased from Evrogen (Moscow, Russia). The Ble gene comprised 5 introns from the *Parachlorella* 40S ribosomal protein S4 (RPS4) gene and was under the control of the constitutive RPS4 promoter and terminator. The expression cassette also included green fluorescent protein (TurboGFP) reporter gene. The expression of the GFP gene was regulated by the constitutive Acyl carrier protein (ACP) promoter and terminator. The Cre coding sequence (SEQ ID NO: 53) comprised an N-terminal NLS (sv40) and 6 introns from the *Parachlorella* nitrite reductase (NIR) gene and was under the control of the inducible/repressible NIR promoter and terminator. The expression of the Cre gene was regulated by the *Parachlorella* nitrite reductase promoter (SEQ ID NO: 1) and nitrite reductase terminator (SEQ ID NO: 2). The vector construct was assembled from these parts into a pucl9 vector backbone with the Gibson Assembly® HiFi 1 Step Kit (Synthetic Genomics, La Jolla, Calif.).

Example 3

Transformation Via Electroporation

The ParaCreXP vector construct was linearized with AscI/NotI restriction enzymes. *Parachlorella* WT-1185 strain was transformed with the linearized vector using a transformation method as described in US20170073695A1, which is incorporated by reference herein in its entirety. Several *Parachlorella* transformants comprising randomly integrated construct in its genome were analyzed on the Accuri™ C6 cytometer (BD Biosciences, Franklin Lakes, N.J., USA) for GFP fluorescence and carried forward for Western Blot analysis.

Example 4

Media Formulations and Culture Conditions

Inducing medium (IM-NO3−) consisted of 35 g/L aquarium salts, 10× F/2 trace metals and vitamins, and 0.361 mM NaH2PO4. The N source was 15 mM NaNO3. Repressive medium (RM-NH4+/NO3−) comprised of the same ingredients as IM media, but further supplemented with 10 mM NH4Cl and buffered with 15 mM HEPES pH 8.0. Cells were grown in culture flasks with vent caps for 3 days on an orbital shaker in a growth chamber (25° C.) supplied with 1% $CO_2$ and illuminated in continuous light (50 µmol photons $m^{-2}$ $S^{-1}$) from cool-white fluorescent lamps.

Example 5

RNA Extractions and QRT-PCR

Figure 1:
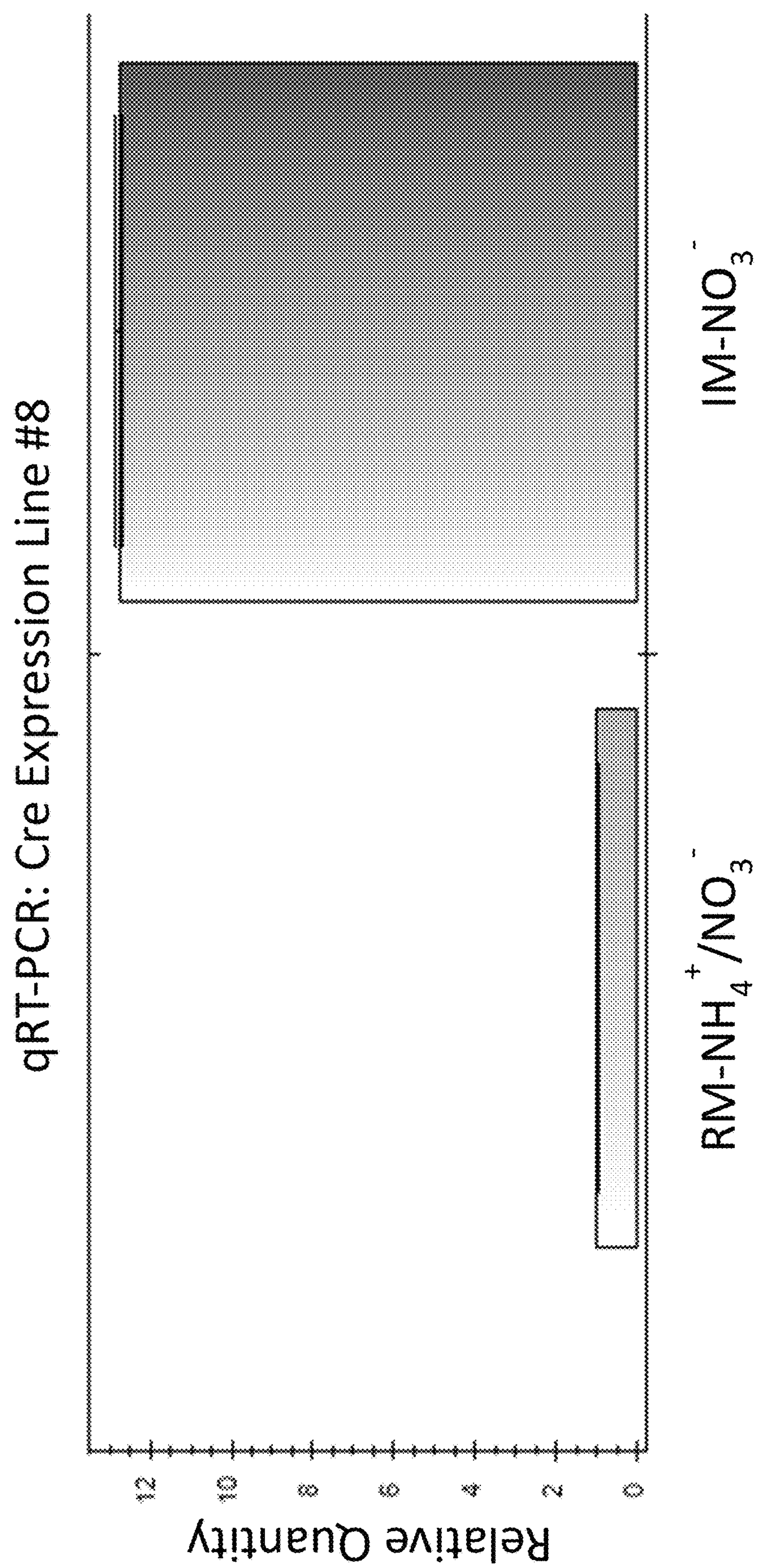
FIG. 1 shows the qRT-PCR results of induction and repression of expression of Cre recombinase gene operably linked with *Parachlorella* Nitrite reductase promoter in *Parachlorella* cell expressing Cre recombinase in selective media. Recombinant *Parachlorella* cells grown under Repressive Medium (RM-NH4+/NO3−) are repressed (left column), while recombinant *Parachlorella* cells grown on Inducing medium (IM-NO3−) are induced (right column)

Strains were grown to an $OD_{730}$ of 2.0 in either IM or RM media, and 5 ml of culture were pelleted by centrifugation. Cell pellets were resuspended in 1.8 ml extraction solution (5 ml grinding buffer, 5 ml phenol, 1 ml 1-bromo-3-chloropropane and 20 µL mercaptoethanol, where grinding buffer includes 9 ml of 1M Tris pH 8, 5 ml of 10% SDS, 0.6 ml of 7.5 M LiCl, and 450 µl 0.5 M EDTA in a final volume of 50 ml) and vortexed vigorously for 5 mM at 4° C. in the presence of 200 µm zirconium beads. After centrifugation, 1 ml of 25:24:1 phenol extraction solution (25 ml phenol pH 8.1; 24 ml 1-bromo-3-chloropropane, and 1 ml isoamyl alcohol) was added to the aqueous phase in a separate tube. Tubes were shaken vigorously and centrifuged for 2 min at 21,000 g. The extraction was repeated with 1 ml 1-bromo-3-chloropropane and the resulting aqueous layer was treated with 0.356 volumes of 7.5 M LiCl to precipitate the RNA overnight at −20° C. After LiCl precipitation, RNA pellets were resuspended in 50 μl H2O and RNA quality was assessed by on-chip gel electrophoresis using a 2100 Bio-analyzer according to manufacturer instructions (Agilent Technologies, La Jolla, Calif.).

cDNAs were prepared with the iScript™ Reverse Transcription Supermix kit (Bio-Rad, Hercules, Calif.) and used as templates for qRT-PCR with the Ssofast™ EvaGreen® Supermix (Bio-Rad). The primer sequences for Cre were F: 5'-GATCTTTGAGGCAACACATCG-3' (SEQ ID NO: 54); R: 5'-AATGCTCACTCCAGCTCTTG-3' (SEQ ID NO: 55). qRT-PCR primers were evaluated for efficiency and the 2-ΔΔCT method was used to estimate gene expression normalized against a control gene (EMRE3EUKT595283; with primer sequences F: 5'-GCCTTTGGTTATCGTGCTTTAG-3' (SEQ ID NO: 56); R: 5'-TCCCTCCGATCCTTTACTCTC-3')(SEQ ID NO: 57) that was empirically determined to possess a low coefficient of variation across different conditions.

qRT PCR results indicate that the expression of Cre in the recombinant *Parachlorella* cell lines was induced in the presence of nitrate ions and repressed in the presence of ammonium ions (FIG. 1).

Example 6

Western Blots

Cre expressing *Parachlorella* strains were grown to an $OD_{730}$ of 2.0 in either IM or RM media, and 5 ml of culture were pelleted by centrifugation. Pellets were washed once with TBS buffer (50 mM Tris-Cl pH 7.6, 150 mM NaCl), then resuspended in 300 μl of SDS-PAGE extraction buffer consisting of 125 mM Tris pH8.8, 10% glycerol, and 2% SDS. 100 μl Zirconium beads were added to the cell slurry and cells were vortexed for 30 seconds before a 10-minute incubation at 85° C. Lysates were vortexed for 30 seconds three more times throughout the incubation at 85° C., then centrifuged and the supernatant was collected. The supernatant was mixed with NuPAGE® LDS Sample Buffer (Thermo Fisher Scientific, Waltham, Mass.) at a 3:1 ratio, and incubated for 10 minutes at 85° C. 25 μl of the mixture was loaded into each well of the gels. For CRE detection, a 4-12% Bis-Tris gel was used and electrophoresis was performed using MOPS running buffer. iBind™ Western blotting devices (ThermoFisher Scientific, Waltham, Mass.) were used to incubate the blots with primary and secondary antibodies. CRE blots were incubated with primary antibody (Rabbit Anti-CRE, Millipore at 1:1000 dilution) and secondary antibody (Goat Anti-Rabbit AP, Novex™ at 1.5:1000 dilution) Immunosignals were detected using the Novex™ AP Chromogenic Substrate BCIP/NBT kit (Thermo Fisher Scientific, Waltham, Mass.).

Figure 2:
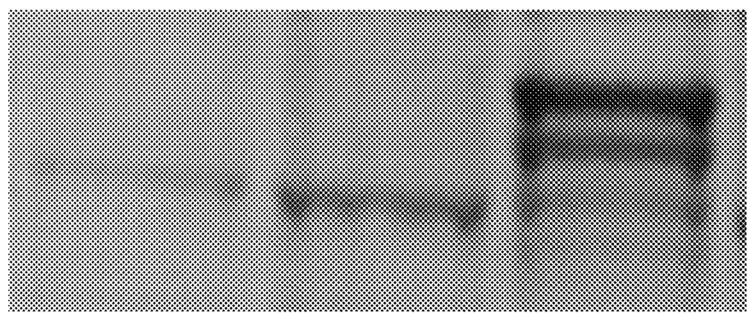
FIG. 2 shows the Western Blot results of induction and repression of expression of Cre recombinase gene operably linked with *Parachlorella* Nitrite reductase promoter in *Parachlorella* cell expressing Cre recombinase in selective media. Recombinant *Parachlorella* cells grown under Repressive Medium (RM-NH4+/NO3−) are repressed (middle column), while recombinant *Parachlorella* cells grown on Inducing medium (IM-NO3−) are induced (right column). The results of the wildtype *Parachlorella* cells are shown in the left column.

The expression of Cre in the presence of nitrate ion, ammonium ion was compared wild-type strain lacking the Cre gene. The results indicate that the expression of Cre is induced in the presence of nitrate ion while it was repressed in the presence of ammonium ion (FIG. 2).

Although the invention has been described with reference to the above examples, it will be understood that modifications and variations are encompassed within the spirit and scope of the invention. Accordingly, the invention is limited only by the following claims.

What is claimed is:

1. A genetically engineered alga comprising a DNA sequence comprising an algal nitrite reductase inducible promoter having at least 90% sequence identity to SEQ ID NO: 1 operably linked to a DNA of interest encoding a polypeptide or a functional RNA, wherein the DNA of interest encoding a polypeptide or a functional RNA is not regulated by the promoter in nature, and wherein the DNA molecule is integrated into the algal genome.

2. The genetically engineered alga of claim 1, wherein the algal nitrite reductase inducible promoter is from the same algal species as the genetically engineered alga.

3. The genetically engineered alga of claim 2, wherein the DNA of interest encodes a polypeptide, and wherein the polypeptide is heterologous to the algal species.

4. The genetically engineered alga of claim 3, wherein the DNA of interest comprises at least one intron, wherein the intron is heterologous to the DNA of interest encoding a polypeptide or a functional RNA.

5. The genetically engineered alga of claim 2, wherein the DNA of interest encodes a (a) a protein associated with lipid biosynthesis, (b) a lipase, (c) a protein that participates in photosynthesis, (d) a protein associated with carbon fixation, (e) a transporter protein, (f) a dehydrogenase, (g) a transcription factor, (h) a transcriptional activator, (i) a cell signaling protein, (j) an enzyme, (k) a reporter protein, (l) a selectable marker, or (m) a recombinase.

6. The genetically engineered alga of claim 5, wherein the DNA of interest encodes Cre recombinase.

7. The genetically engineered alga of claim 1, wherein the DNA molecule further comprises a terminator sequence operably linked to the DNA of interest encoding a polypeptide or a functional RNA.

8. The genetically engineered alga of claim 7, wherein the terminator comprises a sequence having at least 90% identity to at least 800 contiguous nucleotides of a sequence selected from the group consisting of SEQ ID NO: 2.

9. The genetically engineered alga of claim 2, wherein the alga belongs to a genus selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Elhpsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria, and Volvox.*

10. An expression cassette comprising DNA molecule comprising an algal nitrite reductase inducible promoter having at least 90% sequence identity to SEQ ID NO: 1 operably linked to a DNA of interest encoding a polypeptide or a functional RNA, wherein the DNA of interest encoding the polypeptide or a functional RNA is not regulated by the promoter in nature, wherein the DNA of interest encodes (a) a protein associated with lipid biosynthesis, (b) a lipase, (c) a protein that participates in photosynthesis, (d) a protein associated with carbon fixation, (e) a transporter protein, (f) a dehydrogenase, (g) a transcription factor, (h) a transcriptional activator, (i) a cell signaling protein, (j) a metabolic enzyme, (k) a reporter protein, (l) a selectable marker, (m) a recombinase, n) an antisense sequence, (o) a shRNA, (p) an siRNA, (q) a gRNA, or (r) a ribozyme.

11. The expression cassette of claim 10, further comprising a terminator sequence operably linked to the DNA of interest encoding the polypeptide or a functional RNA.

12. The expression cassette of claim 11, wherein the terminator comprises a sequence having at least 90% identity to SEQ ID NO: 2.

13. The expression cassette of claim 10, wherein the DNA molecule encoding a polypeptide or functional RNA comprises at least one intron, wherein the intron is heterologous to the DNA of interest encoding a polypeptide or functional RNA.

14. A method of selectively expressing a DNA of interest in an algal cell comprising: a) transforming an algal cell with an isolated DNA molecule comprising an algal nitrite reductase inducible promoter having at least 90% sequence identity to SEQ ID NO: 1 operably linked to a DNA of interest encoding the DNA of interest, wherein the DNA of interest encoding the DNA of interest is not regulated by the promoter in nature to generate transformed algal cells;

b) growing the transformed algal cells in a media that selectively permits the expression of the DNA of interest in the algal cell.

15. The method according to claim 14, wherein the isolated DNA molecule is transformed by particle bombardment.

16. The method according to claim 14, wherein the isolated DNA molecule is transformed by electroporation.

17. The method of claim 14, wherein the promoter sequence is a nitrite reductase, and wherein the algal cells are grown in a media comprising Nitrate, wherein the expression of the DNA of interest is induced.

18. The method of claim 14, wherein the algal cells are grown in a media comprising ammonium salt, wherein the expression of the DNA of interest is repressed.

19. The method of claim 14, wherein the DNA of interest encodes (a) a protein associated with lipid biosynthesis, (b) a lipase, (c) a protein that participates in photosynthesis, (d) a protein associated with carbon fixation, (e) a transporter protein, (f) a dehydrogenase, (g) a transcription factor, (h) a transcriptional activator, (i) a cell signaling protein, (j) a metabolic enzyme, (k) a reporter protein, (l) a selectable marker, (m) a recombinase, n) an antisense sequence, (o) a shRNA, (p) an siRNA, (q) a gRNA, or (r) a ribozyme.

20. The method of claim 14, wherein the DNA molecule comprises a terminator sequence operably linked to the DNA of interest.

21. The method of claim 20, wherein the terminator comprises a sequence having at least 90% identity to SEQ ID NO: 2.

22. The method of claim 14, wherein the DNA molecule encoding the DNA of interest comprises at least one intron, wherein the intron is heterologous to the DNA of interest.

23. A genetically engineered alga of claim 1, wherein the alga is a Trebouxiophyte alga.

24. A genetically engineered alga of claim 23, wherein the alga is from the genus *Parachlorella*.

* * * * *

SEQUENCE LISTING

```
<160> NUMBER OF SEQ ID NOS: 57

<210> SEQ ID NO 1
<211> LENGTH: 511
<212> TYPE: DNA
<213> ORGANISM: Parachlorella sp.
<220> FEATURE:
<221> NAME/KEY: misc_feature
<223> OTHER INFORMATION: Nitrite Reductase Promoter

<400> SEQUENCE: 1

tcttgcgaag attgaattgc taatagaagg ttctcatcta tacatgagtt accagtgaac     60

cccatatctg ctctataata tagtccccgc tgaggcgcag tgctgaggtt ccagctcgaa    120

cgagccagta gggcttcgac tcacggctca tttattttag agctaggttg acttcccagt    180

ctcatgcaat acatgagagc aggtgttggt cgcacgcctc tctcacggtg cctcttgatt    240

ttcggcccct tgcacccgct ctcatatgac atattcgcgc tgcacccttg ctcagagcag    300

gcgcagcatg tggagtagcg ggcgcaagcc gtaatgagga gtctcagctc aacatgattg    360

aggtcagcat cactgtaaca atacaaatca ttgtggtcct tatatatttg gtaaatgctc    420

gctgcagtat tcaaatcgac cttcactgca agcaactcga ttgaactacg cgcgttattg    480

aaggcacata caaccgggag ttcagaggag t                                   511


<210> SEQ ID NO 2
<211> LENGTH: 1814
<212> TYPE: DNA
<213> ORGANISM: Parachlorella sp.
<220> FEATURE:
<221> NAME/KEY: misc_feature
```

<223> OTHER INFORMATION: Nitrite Reductase Terminator

<400> SEQUENCE: 2

```
tcaggatgtt ttgagcggtt gtaggttctg tagttgtatg gtaggttgca tggaggaaat     60
aggccaacaa caattccaaa tcaaaggaga ttgtagcgtt gctcttggtc cccctgaaaa    120
tttttgttgt tatgtgtcta taaatctagt tctgcacctt gcaaactgtg ggatgccctg    180
tccagagcag aaggtaatcc caaaacagtc gagaaagtct cgttgggtgg ttgtgtaaag    240
tacaaatgta tgttttccac cttgtctttg tattgtgcac gagctacagc attggtggaa    300
gggcttatag ctgctgggtc atcatgctgt cctgttcttg atggtttagg tgtcatccct    360
ttcactgact cagcgaaatc ggatgcgtac cattcatgaa cggtgttgca cttgctgttt    420
gtgaaaggta ctgcatgtgc attgtacaat agactactat aatgtctcat gcacgtggtc    480
aatgatgtag atttctggaa tatgcatcgt gtaattgatt cgatgaaccc ctcgtttgga    540
actctatttg aaaagcaatc gagtgtcatt atccataatg gatgatgatc atgagcattg    600
caaatagcac cattagaaca aactgaatat tgtacacctt gacctggata tgcatccgtc    660
cttcatccca ctttattaag gcaggttata attggcaagg agtcggcaga atagtcgttt    720
ggttataccc cagttttagt ggggcctttg gcagctatat tatggtcgcg actgtaaccg    780
ggtccgttta aagttcgatt acatctcaga aatataattg ggctgcatgt tagaaacttt    840
tcgccgggta taaccggggt ataatcggca tactgcccaa tgacggccag ccgctggtca    900
gtgaccgtca aacggtcgga cggtctgcat cgcatgtgcg ctgacatgtc aagtgcatgc    960
ttctcttaca ttcaggcaaa agactacaag tcattgaaga attgtcaact cagtaagctg   1020
acaattacgt tcatgaaggt cagtcgtatg aaactcgtat ttctccctaa gtcgttacta   1080
tggaaagtac atcgtgccac gtcatcgtca tcgtggcaat gacagatgat ggatagggtg   1140
gggttggcat taattgctat cattttcttt gcagaaaaca aatacctggc acataatttg   1200
ttgataatca tatgtatgta tgtccacatg tcaacgttat atgtataaaa atcaagactt   1260
gtttgcttaa ctctaaattt aatgtaagaa tttcggtaat aatctgatct acattatcac   1320
ttgtgattaa tgttgaaatt tgttatcctt aattatcgtg cttggcacaa ctttcagatt   1380
ttgtctgctg tcacattcat gcagtttcat ttgcagtaaa ttctcaatca tttatgtagt   1440
tgataagaat atttgatctg cttttcatta agcaaatttt gttagctttc tccccttgat   1500
tgttcattca atgagattac attgaatgat gtctacacat ataataagaa cgcatgtcta   1560
cacaaatcta aaaatcagct gcacgctccc aattactatc gcacactctg acaccagacc   1620
gtgctgtgac aatataagct gcactgacaa atttggaaaa cacaagattc agaagaaaac   1680
aaatactgga acccctcaca caccaccttt ctacagcaca aacacgaagc agtagccaag   1740
gtaagaaaat ccgatcaaaa tacattaaat catgtctaat atacagcata agtatagcta   1800
atgaaatcgt tggt                                                     1814
```

<210> SEQ ID NO 3
<211> LENGTH: 2000
<212> TYPE: DNA
<213> ORGANISM: Parachlorella sp.
<220> FEATURE:
<221> NAME/KEY: misc_feature
<223> OTHER INFORMATION: Nitrite Reductase Promoter

<400> SEQUENCE: 3

```
catgtttttg ctatcagaaa aggggccaaa aagccaagga cctcttgatg catacttttg     60
```

-continued

```
atggtatatt gacattgatg gtatcaacaa gtctgtcaag aaaaatgcat tgctatggac    120
agaatagcgc tgtcgtgtgt tggatttggc gcagatgcag ttgtttgcac agcttagctg    180
atcttttaca tagagttatc cacaccatca gtggtagagg cacctgcaac aaatgctggt    240
taatgatcac tagaaacagt gaggtctgca agcccagcat tgcatgatgt gcttagaaaa    300
caccatgttg aaattcctga tcgtagtggc gtaccggcct gcaaacactt cagcattgct    360
tggcctacat attcattacg acacggcttc ctgtgtcgct catcggttta gcattgctca    420
ggctctcttc atcatggata aaattgggca agctgcatgg tgtccagtag gaattgaata    480
aattgttttg gtttgtctga tattgcctca tctgcatgca tggcctgatg gagtcagaca    540
agtgacttgg ctccccatta ttttctagca aatgtagaat cgatatctgc aaattgccaa    600
cttcgcttgt gtatatggac atcctgaatc gctgagaggt tctttccctg attcaccata    660
ccaagcaggg atctgctcat ctgtgtgatg cgatgcatgt tccaagataa tatggcttca    720
ttggtggtaa tgacctcgct attgctggtg caccatacca ggctgaagtt tcaaccgtgc    780
aatctgccac atcgagttca ctgaatctgg aagatgcaga gctgccgaaa tctgcgccgc    840
taatcccttt ctatgtggta gtgaagctgc tgaataaact cttggtgctt tgcaatgcaa    900
caatcatgtt gcatggctgc ctcctttttg ctgatgaggt gatggggggg ctatttttgc    960
gttggggaat gtctgggtgt gaggaatatg tgctgcagta ccacttgaga tctgacaacg   1020
gtgtatgcct gcaacggctc gtttctgctc tatattgagc tgcgcattcc tttgtggccc   1080
tgaaaactgg tggcattgaa tcaaaaactt gacgctcatt tacatgacta aaatattgat   1140
tgtctgtggt gcaatactgt gtccaaatat ctatgaccat cacgggccca catgtttgtt   1200
gaatgcctag tttattcaga aatagttgcg tcgagccttc atattttcca ctcttctcta   1260
tccggcttga cgccggtccg tggagcaaag ctgtatgtac ctcgtgaaaa tacagtgcgc   1320
ttctgctctt ggagatttcc tgggacgtga aatcatggtg ttagcaatgc ccaagcaatg   1380
atgttatcct agctaccaaa cacagttact tccttcaact gcagagactc gcttgcgagt   1440
ctgaactgcg tcaagtcatc tggcatacaa ctcgcaaacg tgaacgtaca ttttattact   1500
gcctctggtt tagcctacag tttcgccagg agttctttaa gaagtaaaaa tccaaccgcc   1560
aggaaggcag ttggcagcaa aacacgttgc aagggcaatg aagttggaca attcatacga   1620
tgtaatatga ataatacaaa tcaatgtgac tcacaagctt tgtacgctgc tgttcgggtt   1680
gcaatagcaa acttcacttg tcaccatgag tacccaccgc accaaacgaa ttccgactta   1740
ggtacccttc aacagcagct tgagatcaga cattatgttc aaaggactac ccctactatg   1800
gcgttgtatg atagctaatt taatttcgct tgccactata taagtgaaag tatgtggctg   1860
tactgtgctg agcagcagta cagtgctagc aatactgaga tctgcattga aacatcaaac   1920
gctgcccaat caaggattat cccgaccctg aatgtgacta tttcaatatt tcaggataac   1980
tttctgctgc ttacgccacc                                               2000
```

<210> SEQ ID NO 4
<211> LENGTH: 853
<212> TYPE: DNA
<213> ORGANISM: Parachlorella sp.
<220> FEATURE:
<221> NAME/KEY: misc_feature
<223> OTHER INFORMATION: Nitrite Reductase Terminator

<400> SEQUENCE: 4

```
gctgctgtac tgtaccattg aaacacctgc gaagggttcc gtgcacctgc tgtgtggcaa     60
```

```
tccgcagaag gagcatggag tgcatgctgt gataccagct gaatgcaagc aagctcgtgg    120

cctatgcatc atgccacagt ctggaacgtc tctgtgctgc tcctggtggg agggagacca    180

gaatcacagt cttcaaacgc tttgttcatg cggcatctat ctgaagcagc tctggtccgt    240

acacagctcg ccgtgtggtt ggtgaacagc tattgactat caggttgtgt attaagtgtg    300

gatgctccag gcctcaatgc ttcctgtgtc tcaaatctct tctgttgcat gtgtttgata    360

cgctatgata ctaactttac tacatttaaa ggcgtatttc cagctgtctg cgaagttttt    420

gcgtggtgtt gcagctgata tgctggcatc aatattgtaa tatacaacgc ctgtgcactg    480

cgtcatagat aaatgatcac tgcaacgtgt gaaagcacgt gtgaaaggcg tgcgccctga    540

tatcacgatc aggacaaccc aacacacatt gggttgattg tgaaacgcaa cattcagcac    600

gtcattacca acagaagacg cacgtgtcgc aaacatcccg acggcatcag ggacctgccg    660

acggaccccc ttcccaattg gtgcgcgcgc caagcgcagg tgtcgagcat gctgcgggca    720

acacatggca gcgaaattgc tgtcgttgca tagagaaatg ccttgctaca tttagaccac    780

agatgatttt ctcggtgcca cgcgtctggg actcgcttgt gcacagcatc tacatcccag    840

tgaaggagcg tac                                                        853
```

```
<210> SEQ ID NO 5
<211> LENGTH: 512
<212> TYPE: DNA
<213> ORGANISM: Parachlorella sp.
<220> FEATURE:
<221> NAME/KEY: misc_feature
<223> OTHER INFORMATION: Nitrate Reductase Promoter

<400> SEQUENCE: 5

actcctctga actcccggtt gtatgtgcct tcaataacgc gcgtagttca atcgagttgc     60

ttgcagtgaa ggtcgatttg aatactgcag cgagcattta ccaaatatat aaggcaccac    120

aatgatttgt attgttacag tgatgctgac ctcaatcatg ttgagctgag actcctcatt    180

acggcttgcg cccgctactc cacatgctgc gcctgctctg agcaagggtg cagcgcgaat    240

atgtcatatg agagcgggtg caaggggccg aaaatcaaga ggcaccgtga gagaggcgtg    300

cgaccaacac ctgctctcat gtattgcatg agactgggaa gtcaacctag ctctaaaata    360

aatgagccgt gagtcgaagc cctactggct cgttcgagct ggaacctcag cactgcgcct    420

cagcggggac tatattatag agcagatatg ggttcactg gtaactcatg tatagatgag     480

aaccttctat tagcaattca atcttcgcaa ga                                  512
```

```
<210> SEQ ID NO 6
<211> LENGTH: 2000
<212> TYPE: DNA
<213> ORGANISM: Parachlorella sp.
<220> FEATURE:
<221> NAME/KEY: misc_feature
<223> OTHER INFORMATION: Nitrate Reductase Terminator

<400> SEQUENCE: 6

aggcactagg gaatgcaatg gcagttgcga agtatttgat cgcgaaactg cgttgtatct     60

gctttttgaa cgtttacaac attcccaact gttcaattaa cccagcacac gctgcggtaa    120

cttatggact attgagatgt ccgaggattt tataatggtg ttttatcaag catttcatgt    180

tttgttgtgc actcacattt gtgttctcct tgccgtaatt ctttcctgtt ccgtgttttg    240

gtttctttct gccgctgtac atcctggagg tgctgataaa cacaggatgt gtattcgctc    300

gatttccaaa tctgtctttt gcaatcatgt ttcccaaacc cacctgacga taactgcagt    360
```

```
agagccgaaa tggactatta tacatgtctg ccatggacct tgcgttccct tttcattct    420

attgtatttc ctcctacagt caagaaatat atagaatgaa gcagtttttc ctgctgattc   480

aagtgcactt gttgcattac agatatgtac tttgctgtta tcaggaataa tgcatgctaa   540

atgtggaatt ccaaaatcat tccacaaccc tgtaatgagg aaagctacgt tgtcccaatt   600

ttccaactta tttgaagcac actttcgacg aacatgccat cccagggatt tacgcaatta   660

tatagcttaa caatactatt ggattaaata cgggttgatc tgtccttgca tgtgcgcatc   720

cacagcctca ggctcagttg gggggttatta ttgctctttt tgattcttgg gcagggtttc   780

tcggaatgca actcgtctta aagctaactg cgaaagtata atcatgactg agttgcataa   840

atcctattac ttcgaactct gtcgcataag catgagtgcc atggcgtcca ggacctcgat   900

atttggtcga gtacgggaca gggtcaaccc cccctgata atggcgccat tatcaggggt   960

gatactgagc aattatcagg tcgcaattca gcataactta tccttaatcc ttctgattat  1020

ggttattatt aatctcatag aattattttc atcggattgt ggcaactgca ctgcacgttc  1080

tttgagattg gaagcttgtg tgtcagccgc gaggtagatg gcgaacaccg cacagcagca  1140

tctggaaggt aggagagcaa tataaatagc ttgatttttt gggtattgta tttttgaagt  1200

tgatttcagt tctaatgcag tggccaaagg ccctcccaga ggccctttcc ctgctgaccc  1260

ttaccggctt ttcgacaggc ttgttcaagc cgcatgtagc ctaatcgacg attttggggg  1320

aagctttctg gcactttacg tcggaaggga caataatgta gtggtctatg gtacccgaga  1380

cttggttgac gctgccatgt cttcagaggg cgctcaagtg atcagagagg agtttgccgt  1440

cctcctacaa tcagatcatt tcggagatcg aggaaccttt ctcccgcagt tgtatcctca  1500

ttatcacatt cctttatttc aacggaagcg gaacgccaaa cgccgttgga aacaacgcag  1560

tagttcagtt gacaacataa ttcagcgcat ttcagcccag ttttcaaggc atccttttac  1620

tctttattat attggtgttt ctgcagaacc cctgcaggca gcacagccca acactatgct  1680

tcaaaccacc tggtggaaga ggtggtttga atcaaaccgt tctacatctg gcgatgctga  1740

gatcgacccg ggtaaggcat caagatctgc tccggcaggc agctgatgct gctgtgcctg  1800

tactgattct tcttgctgac tgcagttgcg cagtcgtttg ggttgccgtc ggtctgtcct  1860

ttgtttggac ctattcgcct gtgatggagc tacaaaaggc tgcaagcttg agaggtatgg  1920

gagctccagg ttgttctgca ccctgctctt ccaccaggtg gtttgaagca tagtgttggg  1980

ctgtgctgcc tgcaggggtt                                               2000
```

<210> SEQ ID NO 7
<211> LENGTH: 862
<212> TYPE: DNA
<213> ORGANISM: Oocystis sp.
<220> FEATURE:
<221> NAME/KEY: misc_feature
<223> OTHER INFORMATION: Nitrite Reductase Promoter

<400> SEQUENCE: 7

```
ggttgctgca agctctcccg gctgtcagcg aaaagtctga gcgattgctg atatgcacca    60

tcgtgggacg ggccaagctc ttgtatgcgt ggcttcagca gcgtcgttgg caccggaggt   120

tgcacgggag gcagccgggt cgggtgcctc ccgacgggaa gaggcgcagc tcctcgcacg   180

gagcgtggcc tcaaaaaccg aggcacaaaa atttttggtc tgcgccccac tcggcacgtg   240

ggaacccgtg gggccaaaaa aacgcgccaa attgaaggcg cccccattga aatgttggtt   300

ccgcccccca aagcaaatgc cccccaacca cccaaaaaag ggtcccttgc ctgggcacct   360
```

```
ttctgcgcct tagggccccg agcgcagtaa agttcttgcc ctcctcgccc aacccggagt    420

gtctggtgaa cgaccatggg agctacgcta agctctaata aatttacgta tcttgcacgc    480

tttcgcttac tataacttcc tcgctagtgt gaacaaccat agttgtaagt ttatcgaaac    540

cgcacttgct atcggagaat caaccgacgc cagcgcgcac gtcgcatcga ggcacctcgg    600

gacactgatc acaaggtgaa acttaggact actaaggacg cttatgcgct tgccaaaacc    660

gtttcttgca accctcaaat aaagcgagtt aagggtgttg caaacccacc gcatgcatca    720

tcctgtacta tactgttctc cgcgtcgagc catcagcacg tgctgctgcg caaaaacaca    780

aagatactat tgtaggagac tactccgata cgacacgtca ttaatagctg cgcatcgcgg    840

ttcatctgca tcgcgcagga ca                                             862
```

```
<210> SEQ ID NO 8
<211> LENGTH: 2000
<212> TYPE: DNA
<213> ORGANISM: Oocystis sp.
<220> FEATURE:
<221> NAME/KEY: misc_feature
<223> OTHER INFORMATION: Nitrite Reductase Terminator

<400> SEQUENCE: 8

acaaggagcg tgaaccgcac cgccccccacc caccttgatt ttttttacac ggtgctggct     60

ggcggggagc aatgggtgga cgggcggagg tgggcagcag cagccgtccc acctaagcgt    120

gcgtatgtgc gccattgtca ctgcctctgc caggggtggt gaaaacactg cttggagagg    180

tgcctaagcc gccaggaggc aactgacagt cccccgcctg cgcgccagcc agtcagcccc    240

cagttatttg tttgatgttc ctcggcgcct gtatttactg tttgccgtct ctagtgtcat    300

gttaatgctg ttcagttgtt aggcctccac ttgctgtggc tcaagctgca tgaaaatata    360

ttttgtgcat gtagaaggtt tttttgctta tgttgttgct gttatgtaca gcagacggac    420

atgtgctgct gttgaaagga caggcccttc aaagcccttt tctttccttc atttccttgc    480

agcaacgtcg tgcgttttgc atcacagtga gcactatttc cactgcagtg gacccccccct    540

ctccctgaca ttaaagcact cgcacaccaa ctcgagtgaa aacacgtggc aaccagcaca    600

atccttcgac ctccctcccc ggggcccgga tccatcaaga tagcgtacgg ttaattgcta    660

ttaagaaaga ttccaaaacc aggaaaaagg gcaattgata agtgaggtga atgaacatag    720

ggcggctgag agcaagtttc caaggcggta tcaatgttac atattgtata gacagtatca    780

atgtcacaag tgacacataa tgcaaggcag tatcagtgac aattgtgggc ataaggaata    840

ttgaattgaa tccagatgat accggcaaat taaggcatgg gaaaccgctt tcctgaaggc    900

cttactggcg ctcgtgccga cgccgccggc gcccgtatcc tcgtgccaac gctgtggccg    960

ccactctcct cgatcaggcg cccgtgccgc cgccaataca acacctttgt ttagtttcga   1020

tttggggcac ttatctctag ttgggccctt ttcgggcctc ccctacccag cgccttgttg   1080

gaaagcgcag ttttaatacg atagttccaa taacgacggt ttccaggtac ccattcgccc   1140

tgcttgctgt tttaggcgct tggggcagct ggctggtggg tgctgccgcc gcagccacgg   1200

ccaacgcttt cctagatgcc ttactggcgc ccataccggc gccgccggcg ccggtatccc   1260

cgccagcggc gcccgtgccg ccgccatggc caccgctctc ctagattcgg cgctcatgcc   1320

gccgccattg gcgcccgtac ccccgccatc agcacccctg ccagaggccg ctgtggccaa   1380

cgcttcccta gaggccttat cggcgcccgt agcagcgccg ccagggcccg tatccccgcc   1440

gctggcgccc gtaaaccccg gagccggccc ccgagtttca gccgccgttg gtcgggctcg   1500
```

```
ggtcgtttct cgtgcttgca cgatgtttaa cgattcttta aaaaaaaaaa cgtttgtgcc   1560

gagccacagg ggcccgttct cccgccggca gcgcgcatgc tgacgacgcc atgaccaacg   1620

tttccctaga ggccttacag gcgccatacc ggcgccggcg gtgcctgtaa ccctaccggc   1680

ggcgccgcgg cgctgccgtg atggccagcg ccctcataga tccggcgttc gtgccgcagc   1740

caccagccgt ttgcccgtcg gcagcacgca tgctgacgtc gccgagccaa cgtcttccta   1800

gaggccttac aggcacccat accggtgccg cccgcatccg tacccccgcc ggcagcgcct   1860

gtgttgctgc cgtggtggcc aagctgccat cctagatcct gctgcattca tgctgcagcc   1920

accggcgtcc attcccctgc cggcagcgtg tgtgcccacg ctgctgtggc caacgtttcc   1980

ctagaggcct taccggcgcc                                                2000
```

<210> SEQ ID NO 9
<211> LENGTH: 2000
<212> TYPE: DNA
<213> ORGANISM: Oocystis sp.
<220> FEATURE:
<221> NAME/KEY: misc_feature
<223> OTHER INFORMATION: Nitrite Reductase Promoter

<400> SEQUENCE: 9

```
attgacagtg gcatgtagcc ggtgagagcc aggcatggtg gcaaggtcgt tcttttacta     60

agagagtttt cctcacgagc tggacgtgat ttagccggtg agctggacgt gattgaactg    120

gcgagctttg cttgtgctgt ggctcctcat ttggaagaaa atagcttgtt ctgttttgct    180

gccagaacct tttggcgaca acacctttcc attgatccgg ccttttgccc tggtgtcgaa    240

cacgttccct gcagccattt ttgaattgag ctgggccctg ttaaaggcgg gcatctagtt    300

tgcgtgcaat ggtgtccagc acctgccccc ttttgcccct cagtatatac tgaccagagt    360

gggatcatgc aaaagcatgc aattaaccta ggaggggaat tgggacaaca aaaggaggga    420

atgcaaacgt tttccaagtg aaaccgggaa gggcagccta agcacccccc ctacaaacac    480

atgcctaaat tactacaaga tcgggtctta tattatgctc ttgcagcaag cggaaccgca    540

ccaaaaggac taaagcggta accgaatttc cgtgagcacc agccgcgagt tggcagctgc    600

gatgacccac ctgctgcaac acgccagcca gaagtgttca tgccctcaat aagggggatt    660

gcgctcagtt tgtcaccgtc gtcctcgatg acgcagctgc tgcagcgcct ggcagggcca    720

ctgtgaccca ggctgcagcc tgccagcaaa agcagctcgt tgaattaagc ggggtcacat    780

agatgcagcg tcatcgtctc atcgtagtgt ttattccgtg atgggggccg tggatctaat    840

tcctgaccgc cccccgctcg attttagtgt gtttctctct cggtgggcgc accgtgatgt    900

gctgtgctct tgtccggccg taggcgggcc cttggtcgtc catttatccc tagtatcccc    960

cgtccctccc ccttccccgt ccgcctagct cgctttcctt ttgcccttcg cttgcctgca   1020

tctcttgtgt gcctcataag gtttatgctt gagcccgttc tgtctttgct ctgccgggtg   1080

ttctgggttg ccctgggtgc tagtgatagc gtggcggggc cgctcctctg gctccggcac   1140

ggccggcgtg ccgtgtcgga cagcctggct gcgtggagag cggaagcgtt ggccgctctt   1200

ggcctcgctg cgggcgtggc gcacccccgt tcttccacac cgcacactat ttgctcagtt   1260

cccgcccggt tcgcctgacg ttgcattgat agggttggtg atagtgttaa ccctttgtgg   1320

gcgccatcgt tgatggtttt ctatagaatt tcgttagtgg gatcttgttt tccctttta    1380

ttgtcccccct ccgggagcgt gttccttgtc atggtgggcc cgtttcttgc ggcccgccca  1440

cctgccattc attggccccc tgtcgtcatg accacctcgc ccttgtggcc ccccgagttt   1500
```

```
cgatcgccct tggtcgtcct cgggtcgttt ctcgtgcttg cgcgatgttt aacgattctt   1560

taaaaaaaaa aaaatgcagc gtcaacctgg cgaggcgttt gggaagtgcg ggtgcactgc   1620

gaggtggatt ctcgctgagg gtcctcggca gaactcggca gaatgtaata tccataatat   1680

ggtgactgtc acatgccaat ttgaaatggc agaataaagt gccgcgaaca gtgatttgac   1740

agtatgaaac actaaaatac aaataaaaca ccaaaacatt aatagggtta gtgcttgagc   1800

ctgcaatacc ctacacagcc aggtgtgtcg gcaccgggca caaagtcaaa agtgaagcaa   1860

cggcttaagc ctgcgacaac gttccatcca tatcaaaaat tgaaagggtt ggcacttcgc   1920

aatcttgctt tgctgcgtgg tcggagcgcg gagcgcacag cccgccttgt tgccccggct   1980

tctaacctac cgaaaccgtc                                                2000
```

```
<210> SEQ ID NO 10
<211> LENGTH: 2000
<212> TYPE: DNA
<213> ORGANISM: Oocystis sp.
<220> FEATURE:
<221> NAME/KEY: misc_feature
<223> OTHER INFORMATION: Nitrite Reductase Terminator

<400> SEQUENCE: 10

tagcaggatt acaaggagga ctacccaggg ctgcggtccc tcctggacgg cgccttgtag     60

taccatgatg acaaggagga ctgccagggc tgtaattttt cctggacggt gcccattagt    120

accaggatta caaggaggag ggcctagggc tgctggatgt gcgttcctgg gcggtgcaac    180

gttgtagcgc ttttgtgctg ggtgtgcttt cctggcggcg ccggatagtg gtaggattct    240

tggacagcgc gctgagtaca ggaagaggga gtgggaggac tgccaggtgc tgtggcatgg    300

taggtagagc gggagcgagc ggatgaggta ggggctagtg ggcctgtagg agaggagaag    360

cagggcagta gccgagacga ttcagtaagt aagcaggatc gtgagcaggc cgggcgcgag    420

ctacacctgt tgtgaaggca cctccccaag cggtgtttgc acccgttgtg aattatgatc    480

gtttgtgttt taattgtgaa cgcgcagcgc gctcgctgtc tgtatttccc aggccgctcg    540

tagcgtgcac cagtgcagga acatgcattc ttgttacgtc agaattgaaa attggcatgg    600

ttaggtaggc agcaagcctg tcaggttgtg cttctcttgc tcaactgctt tcatgctgcg    660

tgcagcctcc aaccaggtgc cccagattct attttgcctg cttcaccaca aggcacatgt    720

aacgtatgag gttatgtctt tccctcggcg catcagggaa tgtagagtac actcctaact    780

aaccccctag caacgtcact atccaaagcg aaatttaatt tttcatgagt ttcaacgcca    840

cttccatcgt cttaaatata ggctgctact cgcggttgtt cttcttggta agttgcggtt    900

tgattaccac caatggcgag cccactgaca cggatagcaa tttgcagcac ctggcgcagc    960

acatggcgga aagggcattg cacatgaaca cggctgattc cccatcggac acggcatgca   1020

ctgctagctg gcagcaatca tgcctgcacg gcatgcatac atccaagggg ctcatttttt   1080

tttatgtgaa acgtgttaca cgaagaaaac acattgaccc caccgaagtg gggcgggcca   1140

tgaaggccta cctagggcta tggaagccat gcatatgggg gccaataaga atggcttatt   1200

ggtgctttga agccttggct atggcgaaag atgagccata aaaactgaca atgcaagggc   1260

ctggacgggg cccaaattgc ctccactgaa aaagaaaaaa ctatttaatc tgatgaaaat   1320

ataatatctg ctatataacg cggtggaaca taacaaagca ggtacactcc caaattaaaa   1380

ctgtgcccaa ccagtgaaag gagccccatc ctggtgtgtt gcatgccggt ttttgtcgtg   1440

agcaggagca accacatgat acgtttatga gttaccaaaa gtcatttgta atagcaaaca   1500
```

ggccaacccg ccattgagag gataaatggg ggaaactatg aggctgatgc gtgctcagat 1560
ggggctgccc cggttccccc cacatcacct tcattaaggc tgcccgcgat ttaagaccaa 1620
acaattggcc agccccacat ggggagaaca aaagaacgag gagcactaca gctatcttgt 1680
attttgtcca aacaagcata ttgggaaaag gcgaccatta tcgttgatga ttgagcagag 1740
actgtacatt cagcgacatt ttagcactat tgctccagct gccgccactt gctgacgagt 1800
tttattgagt tttattgact gaaacaagta gacaaattgc gccaatcggc aggagcaagg 1860
ccgtacgcaa aacaaactca gcaagtagcg ccccaaagcg ggtgaccacc agctcgcaca 1920
tgccattgat tgaagtctgt gcctggccga tagaagcacg gcaaaaaaaa cagctgccat 1980
gagtactcta agggtcctaa 2000

<210> SEQ ID NO 11
<211> LENGTH: 862
<212> TYPE: DNA
<213> ORGANISM: Oocystis sp.
<220> FEATURE:
<221> NAME/KEY: misc_feature
<223> OTHER INFORMATION: Nitrate Reductase Promoter

<400> SEQUENCE: 11
tgtcctgcgc gatgcagatg aaccgcgatg cgcagctatt aatgacgtgt cgtatcggag 60
tagtctccta caatagtatc tttgtgtttt tgcgcagcag cacgtgctga tggctcgacg 120
cggagaacag tatagtacag gatgatgcat gcggtgggtt tgcaacaccc ttaactcgct 180
ttatttgagg gttgcaagaa acggttttgg caagcgcata agcgtcctta gtagtcctaa 240
gtttcacctt gtgatcagtg tcccgaggtg cctcgatgcg acgtgcgcgc tggcgtcggt 300
tgattctccg atagcaagtg cggtttcgat aaacttacaa ctatggttgt tcacactagc 360
gaggaagtta tagtaagcga aagcgtgcaa gatacgtaaa tttattagag cttagcgtag 420
ctcccatggt cgttcaccag acactccggg ttgggcgagg agggcaagaa ctttactgcg 480
ctcggggccc taaggcgcag aaaggtgccc aggcaaggga ccctttttttg ggtggttggg 540 gggcatttgc tttgggggc ggaaccaaca tttcaatggg ggcgccttca atttggcgcg 600 ttttttggc cccacgggtt cccacgtgcc gagtggggcg cagaccaaaa atttttgtgc 660
ctcggttttt gaggccacgc tccgtgcgag gagctgcgcc tcttcccgtc gggaggcacc 720
cgacccggct gcctcccgtg caacctccgg tgccaacgac gctgctgaag ccacgcatac 780
aagagcttgg cccgtcccac gatggtgcat atcagcaatc gctcagactt ttcgctgaca 840
gccgggagag cttgcagcaa cc 862

<210> SEQ ID NO 12
<211> LENGTH: 1694
<212> TYPE: DNA
<213> ORGANISM: Oocystis sp.
<220> FEATURE:
<221> NAME/KEY: misc_feature
<223> OTHER INFORMATION: Nitrate Reductase Terminator

<400> SEQUENCE: 12
gaagaggcag gcgcatccga actgcttgcc atctcttagt gttgttccat gtcttctttt 60
atttatctgt gtgtgtgtgt gtgtgtgttc gctcgcatgc gacgcatttg tttgttgggt 120
gtgccccccc tcatgctccc tgatggagca caccacgtag acacacagtt gcatcctgca 180
ctttatttgc tgctgtcagc gctggcggtg tggtgcgttt gtcaacatgt atgttgcgtt 240

-continued

```
ttcctttgta cctattttgc ccattcctct cttccatctc tttctgcttt atggagtgaa    300

tggtgctccg tgatgccctt ccggtcgccc taaacaggtg cagaagctgc aactgtttca    360

ttattgatga ggcagttctt gcctctctct cactagcttt atttttggcc ttgatttctt    420

tcctggtggt acttgttttc gtaatgcagg cctcacccgt gtttgttgct ttgcgtgctt    480

atttccgttt cttgcactga tgcacgcgtt tcttgacggt gtattttctg taaccagcat    540

cgttttccct tggaaccacg cttcttcaat acgcatgcac agaagaatgc actgacatca    600

tgcgggtggt gttcaaatcg ttgcgcagaa ccgtctgcct cgttgcaccc ttcgactgcc    660

gcgccgaacg tactgtacag tatctttacc ataagacaac gacgtggaat gtgaggcaga    720

aagacccctg cctgccttat cacgcacgta ccgaactact catttgattg acacttcaaa    780

gataaccaat ctatgatcaa gtcgagtaat tgccaagccc ttcgtacact tgcctcatta    840

acacgcacat gttccttttt gtgcatgcat gcgcacatgt gtgcgcttcc ctgcacaaaa    900

atattaggta ttccatacac atcctgacac acacatcatg cccctgctgc atccaacatg    960

ttctgcagcc cttggtggct attgcatttc gactgccagt gtttatcagc ccctcccaca   1020

cccaattgtc catcacacaa accacgccca tcccaaccca catcagtctg acgcaacgga   1080

ttcccacgtg atggctaccc tagccaaaac ttaaaatagc aacatccgtg tccagcatcc   1140

acccattccc tcctctgaac acctgcccgg acacccaccc tacaccactg gcccgccgcc   1200

ccaaacccac tgcccgcccc cccccccccc accccaccca aaaaaaaaaa aaaaactgtg   1260

cataatgacc atatttcaaa cgaaaacaac tgaatgttaa cgggtaccct ctcctgaggt   1320

ttacccagtc tattgccgcc ctgcttttcc tgctgtagct tactctagct accttttcta   1380

ctttccccca aaccgtttgg ttctagggtt tccctgtccc ccttccaccc cctttcaggg   1440

ttgccagggt tgctgagggg ttgtcccccc tccacttctg cactggtgct ctaacggtcg   1500

tcttgtgccg ttgtccgggg ccctgtgccc gtccatttga tcgagttact gcatgagcag   1560

ttaatcactt gcgttaccac catcctacct tgtaacacct aaacattgcc ttagtcttat   1620

tagattatga gcccacgagg cctttggctt tgtttctagc cgctttcctg tcccatcggt   1680

tcgattccgt cggc                                                      1694
```

```
<210> SEQ ID NO 13
<211> LENGTH: 411
<212> TYPE: DNA
<213> ORGANISM: Picochlorum sp.
<220> FEATURE:
<221> NAME/KEY: misc_feature
<223> OTHER INFORMATION: Nitrite Reductase Promoter

<400> SEQUENCE: 13

atgattcgag agtcaatata aagttatcta atctaaataa tagaaagcat gtgtgtattc     60

gacgtgattg acccagcacc caagttttcg tgtacctgaa tcctaccaga tcgtcaccag    120

cttgttgagg tgcccatgac accaaccatc gctatattac tatcagtcac tctcgagacc    180

attatttatc cactaataat gaatactggt attcatatac catgatatct gagaatactc    240

tgggacatga accggatgct gagtcgttga caattcgttg cagaaggaat cccatcgaga    300

cacaccattg accgtaatgg ttgaaattct tcgatggatt gccatgctct atgagagtgg    360

atgatatctg cagtcaaacg cagtcgtcaa agtcatattt gagcagcaaa a             411
```

```
<210> SEQ ID NO 14
<211> LENGTH: 96
<212> TYPE: DNA
```

<213> ORGANISM: Picochlorum sp.
<220> FEATURE:
<221> NAME/KEY: misc_feature
<223> OTHER INFORMATION: Nitrite Reductase Terminator

<400> SEQUENCE: 14

```
tcgacacgcc gcatgcacac atgctaacgt aacgttcact gtactatgat cattacatgc     60

aaaactcatt tccaatctta ctattgtaaa gagtgt                               96
```

<210> SEQ ID NO 15
<211> LENGTH: 361
<212> TYPE: DNA
<213> ORGANISM: Picochlorum sp.
<220> FEATURE:
<221> NAME/KEY: misc_feature
<223> OTHER INFORMATION: Nitrite Reductase Promoter

<400> SEQUENCE: 15

```
cttctatata tcttcttctg gtattgcaca taaataaaga gagagagaga gttgtgtgca     60

gcaattacat cctcctctgc agatttcttt actgcatgaa atccatctca atcaagcgat    120

ataatataat gcaaattctt gaaggcctca ttgttaaggt aacctcgatc aagggtttct    180

cgacggaaga acaaggtgag tctcacgcac tcaccaccgt gagtgtgagt ctgcagactc    240

actcgaaacc ttgggaggcg aatctcatca ttatcagcct caggcaagca cctaatgaga    300

aataaatatt actataacgc ttttattgac aacagactgc gtacgacgtc agagagtaac    360

a                                                                    361
```

<210> SEQ ID NO 16
<211> LENGTH: 155
<212> TYPE: DNA
<213> ORGANISM: Picochlorum sp.
<220> FEATURE:
<221> NAME/KEY: misc_feature
<223> OTHER INFORMATION: Nitrite Reductase Terminator

<400> SEQUENCE: 16

```
taataataat gcaatgaggg cggatcaagt cgattgtggg atttctattg cccatgggat     60

tttctcagaa ttggacatga ttttgtaaag tgataatttg agccaaatca actctacttg    120

gtctttaatc aaccctttttg atgcattcaa acatc                              155
```

<210> SEQ ID NO 17
<211> LENGTH: 436
<212> TYPE: DNA
<213> ORGANISM: Picochlorum sp.
<220> FEATURE:
<221> NAME/KEY: misc_feature
<223> OTHER INFORMATION: Nitrite Reductase Promoter

<400> SEQUENCE: 17

```
ccacgccgcg gttccgaatt gtatataaag ccatggtcat atgtttgacc tcatgcatgg     60

atgaacatca atttgcatga agatcagcga ttgcctatac agtatcgatg gatgcgttgt    120

cattttcaaa aagatacatc tttaagaata tcagcaacca tatgggcctg ctcttgtatc    180

aaatggataa gaggaagcat gatcaaagtc cagacctact actcctaccc tggctcacga    240

ggagattcag tttgagtctg agtccactga ctcacataca tcagggtttt ccatgaacga    300

tgaacagatg gaaggcgttg ctgataatct aatttcacat ttaattacat ttcatgattt    360

ttaaaacaca tcagttgtag tcttttggcc tcaatctcac tgtgggattt ttcaactggg    420

tgatactgtc ttcaag                                                    436
```

<210> SEQ ID NO 18
<211> LENGTH: 929
<212> TYPE: DNA
<213> ORGANISM: Picochlorum sp.
<220> FEATURE:
<221> NAME/KEY: misc_feature
<223> OTHER INFORMATION: Nitrite Reductase Terminator

<400> SEQUENCE: 18

```
gttcttgcat ggccttttga ttgctgattt aatgaaagtt tacattccat ttaataattc     60

atagcgcccg tgtgtgtcaa ataaaatcaa agcattacaa aatctctaca ttcaaaaccg    120

tttgaatggc cttgtctcat gaaaacataa tccaatcaaa gcgaagaata accaggcagt    180

aaacttatac tccttgcttg aatcttcctt ttggtatgtc acaatggaac caatgcatgc    240

aaccaacccc atcaagaatc caacacaata cctaaactgt agccaaggag ttgtcagctc    300

ctgccaaact gtacgcttat tcttattact ctgtactgac ggttctttcg gttgttgctc    360

tacacccttc ctgcttttcc gccgtctcag ctctacagca gcaccagtct tggcagagga    420

cctagcttca ggcatactca atacgttttc cacagaaatc tccgtttctt cgagaatggg    480

cgtaaatatc gtcaatatta aattcgaaca aaaattaacg ctgcaagtac agtgaaattc    540

aaaatataga ttcaatctgc ccaaaccaaa cctagggcac ggtcatatga cgcaacccag    600

actcaattgc aattctgagt ctgcagactc ctcattcatt catcatggat ccgattgagc    660

tttgacaccc atgatggtgg atggacgata tctcatactc gctcttattc tcatgtatgt    720

atcgcatcgg atgaattgac tgtgccagcc tggagaagaa gaagtcttgg accaatgcat    780

tattactgca ccattaccag gccttggaaa gatccacaga gacttgtgca tatgattgat    840

tacaactcta gccttctagt gtacattata ttttaacatc gaaacgcaaa tttacatgaa    900

aaaaaatcgt tattgttact atcaaatca                                      929
```

<210> SEQ ID NO 19
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Promoter

<400> SEQUENCE: 19

```
acggggccac ccacgtagca agcgcaagtc cgtcaccagt gccagccagg ttggcgtcgt     60

cagagccttt cgcggtggat ttgttattgg ccttgagcaa ttcacagcag taccggaagt    120

agcgcgcgca agtagttgaa tggtagtaca ggtatccgta tatataatag gtatttttg    180

ggggggtttt aattaatagt aatttactat taattaccgc ataaccggta ttgtacaata    240

aattagcccg agcgcgcggc gcgcaccggg ccccgctgcg agccagacac ggacgatgcg    300

acggtgttat tttgagtacc ggcggcacca gtaaactgcg cactgccgtc ttcccgccca    360

gcagagctag gcgccacgtc ccgcgccggg caggcgagga agcgaatgtt tgtgctagtt    420

caatagcatg cgtcatggtg ggtgaaccgg ctagcacttc gtcggtacgc atccgattgg    480

cacagccggt accatgccgc ggtactgttg tggtggagta ttgccttcgg agggatattg    540

ctctccgcat cttgtcatgc ttgcccgtcg catgccctgt ggagcgcacg aatatcgtcc    600

acatgcgtgt ggccaccaag acccgcgctt ctctcaaaca tgagaatgtg gtgaagttgt    660

agtattgcta tatgaatttg ggcttgctgg agaactacga caaagatgtg ctgaacatgg    720
```

```
tggaggatgc taacgacctg ctagaatagc agggtcaagc aacaccccaa gcacccctag    780

cacccccctgt tgatgatgct atgattattc ttgactgatg tacgcatgta gcgagtaggt    840

atatggggtg caatatgcac tgtgacaagc cctttggctg ccatcgccga tgtgttagcg    900

agtctaaatt gccaagacat gagctccagc aatatattat ttatattcct ttatctaata    960

aaacgcagta atttttgatt tcggagtttt aattgatata aatttactat taattaaaaa   1020

aatagaataa aataccataa attactgggc ccaggtagta caggtagcag tcgcagttgc   1080

tgtagaggac ctctctgatt gtcctttttta ggtgatttcc tgatatcgcc ttctgctgct   1140

agctaatgta atattagtac aggtagcagt cactattaaa aagaaagaaa tgcccgtatt   1200

attattaatt gttttattgt tatattttta gcggtaatcg ctgtactact acttggtttc   1260

cgtctgcagt aaactactaa gggttactgc taccgttgga attaattaat taatagtacg   1320

aatattgcaa aatcagtaat gtaataaaca ccaatacaga accaatgcca gcagtatcgt   1380

ctggcctttt tgcaaattca caccaatacc agcagtaggt actacggcgg gtaccagccg   1440

cctgggcacg ggtacaggtt ctcgcatggc accggtaata aataatggca tgccgaattg   1500

ccgatatcgc cccgtgattt ccgtgacacc gcgccccccc ctgctgacca gtacctgcgc   1560

tgctagcgac taatcacgcg cggggcgcca gcaacagcag ttgcgcattg cgcatatatt   1620

gagcgttcaa tatttgccgc ggtcatagaa agcaaaaaag ccccgcccct acccaccccc   1680

ctcctccacg cccgcctgcc aatctccgac accccgctag tagctggcgt ccctccacgc   1740

gctaccgcac cgcacctccg ccaaaaacct cagtccatag cgccagagta tggcttccca   1800

ggtgaggcgg cctgtggact gtcgacggac ggcgtttagt gaagactcca gcaattagct   1860

tccgccgatc catattttgt cacgtgatac ctagtacata actgctgtgg gtttgccccc   1920

cccccccccc cccccccccg cggcaattgt cagccagtaa ggcactgacc accatcgctg   1980

cacctggcgt gtaggcctcg                                               2000
```

```
<210> SEQ ID NO 20
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Terminator

<400> SEQUENCE: 20

taggccagtt gcgcatgtgc tgcgcgcact gggacccaag cagttagtgc agccctacaa     60

gcgcggggga tgccatattg tatatgtttc tattaggcat tcgggcctgc cacgatgcca    120

tggaggcgca actacatgag atatagacta gtttgtcact gatgcggcca tattaaagag    180

tccatatgtt ctgccaccgg ctgggcgata ctgcgccgtc cgcatgccta agcgtcatgg    240

aattcgcgag tgggtgcatt accagggccg ctgtctacta tcaatggaag atgggacggc    300

gttttgaagg ttgagttgtc gctcattacg agtggatgat gagcaaaaaa tccgcgcgtg    360

ctttcactag gcgcaacagg tattggttcc tttatggatt ggatatatcg ctgcagcata    420

tgtcgtaatc gtcactatgt agtcgactta cagactgccg ggcatggcca tgatatgttt    480

gcgtacatca atcacaacga tacggtaagc acactgcttg acctgtgcac atatgctcta    540

gcagcagaag gcgatatcag acaatcacca gaaaaggaca aacagaaagg tcctccaacc    600

tgtgcacaca tccgacccca gcatcgtcca cgacgaccac tagcgacaat acaggattgt    660

tcccacgacc cagcgctact acgagtacgc tcccgaacat gaacaggcac cggttttgat    720
```

-continued

```
atggactggt acgatgacga ggcggatgat ctgacaacga cggccgtcga cgagaccctg    780

caagggtttc actggtgcca gtcctgtccc gggggcgggg gaaaaaatgg cgacaactgc    840

tgtaaaaaat ggctccccgt actcgtacca aaacccgcga gtagcatcgt cgtagtacag    900

gtagtcggag tccccgcccc gcgtagcccg tggtacccgt acggggtagt accagtaccc    960

gaggtttttt ttcacacttc accgccgact ttcccagtgt taagcgcagt tctgccgtta   1020

agtacggtgg gacccgtctc cgcccgccgc ccgccgcgca gcgggggcgg gcgggagatc   1080

ggaggacatg ctcgtgacaa agcgtcacgg cgggcagcca ccaggccgtc cgaggcgtag   1140

gagacggtgt gctcgtgccg ctggcggcac gctgggggtg gcgcgggcgg gcgcgtggtc   1200

gatgccgcct ggagccgcag gcgttgactg cgctgtccgt ggtcgtcccg gtttttcgat   1260

ttcttgcagt actttatgca gtacttccga tgccggcgtc attcccaccc agcccacagc   1320

cccctcccga cccctcagcc caagccccaa ccccgccccc atccccgcag ccacaccacc   1380

gccggcgcgt atccccgagt cacccgcggc accgtccgag gcagcttcac agcacctatc   1440

ttcgcccgtc ggtccgcact tcacggtgat gactccgcgt gcgcgccgcc cgccatggtc   1500

caagccgcac ccctccgccc cccattcccc aaccacaccc gctcccctcc ccaaccccgc   1560

agccacacca ccgccggcgc gcatcccgag tcacccgcgg caccgtccga ggcagcttca   1620

cagcacctat cttcgcccgt cggtccgcac ttcacggtga tgactccgcg tgcgcgccgc   1680

ccgccatggt ccaagccgca cccctccgcc ccccattccc caaccacacc cgctcccctc   1740

ccaaccccgc agccacacca ccgccggcgc gcatccccga gtcacccgcg gcaccgtccg   1800

aggcagcttc acagcaccta tcttcgcccg tcggtccgca cttcacggtg atgactccgc   1860

gtgcgcgccg cccgccatgg tccaagccgc acccctccgc cccccattcc ccaaccacac   1920

ccgctcccct cccatccccg cagccacacc accgccggcg cgcatcccga gtcacccgcg   1980

gcaccgtccg aggcagcttc                                                2000
```

<210> SEQ ID NO 21
<211> LENGTH: 1492
<212> TYPE: DNA
<213> ORGANISM: Tetraselmis sp.
<220> FEATURE:
<221> NAME/KEY: misc_feature
<223> OTHER INFORMATION: Nitrite Reductase Promoter

<400> SEQUENCE: 21

```
actgagccct gacaatgccg tgcgcagggc gtcgtgctag cgcaggcgga taatatcgac     60

aaggatcgct tcccctcgcg gcacaggtgc cgcgcgattg ctggtgcgtg aagcgcaaca    120

gcaaaaggga tgagcgctat ggtctagaca gttggctaag tagtagctgc aggcaggcag    180

ggaaacaggt cgggagctgg tgcggtcgcg agtccgctgc tcactgtccc atcctggaag    240

attctagaca gagccgatga ctggctactg tgctatattt tccaggtggt agtcgttcga    300

ccgcacaact cggtccgtcg tctgactaaa ctcagttaag tacttaacaa cgaataattg    360

tcaaaatttt aggatgtgca cgggtacgtg tacgagcatc atgtaaaaat gcaaatgttt    420

ccaaaatagg caagaggatg aagatcccca ggatcggggt agaatgttcc tttaattaat    480

agaaatttac tattacttaa aaaaaataga aaataccata aattactggg cccaggtagt    540

acaggtagca gtcgttgttg ctgtagagga cctctctgat tgtccttttt aggtgatttc    600

ctgatatcgc cttctgctgc tagctaatgt aatattagta caggtagcag tcactattaa    660

aaagaaagaa atgcccgtat tattattatt aattgttcta ttattatatt tttagcggta    720
```

```
ttcgctgtac tactacttgg tttccgtctg cagtaaacta ctaagggtta ctgctaccgt    780

tggaattaat taattaatag tacgaatatc gcaaaatcag taatgtaata aacaccaata    840

cagaaccaat gccagcagta tcgtctggcc tttttgcaaa ttcacaccaa taccagcagt    900

aggtactacg gcgggtacca gccgcctggg cacgggtaca ggttctcgca tggcaccggt    960

aataaataat ggcatgccga attgccgata tcgccccgtg atttccgtga caccgcgccc   1020

ccccccgtga ccggtacctg cgctgctagc gactaatcag gcgtggggcg ccagcaacag   1080

cagttgcgca ttgcgcatat attgagcgtt caatatttgc cgcggtcata gaaagcaaaa   1140

tagcccgtcc cacagccccg cccctaccca cccccctcct ccacgcccgc ctgccaatct   1200

ccgacacccc gctagtagct ggcgtccctc cacgcgctac cgcaccgcac ctccgccaaa   1260

aacctcagtc catagcgcca cagtatggct tcccaggtga ggcggcctgt ggactgtcga   1320

cggacggcgt ttagtgaaga ctccagcaat tagcttccgc cgatccatat tttgtcacgt   1380

gatacctagt acataactgt tgtgggtttg cccccccccc cccccccccc cgtggcaatt   1440

gtcagccagt aaggcactga ccaccatcgc tgcacctggc gtgtaggcct cg           1492
```

<210> SEQ ID NO 22
<211> LENGTH: 1460
<212> TYPE: DNA
<213> ORGANISM: Tetraselmis sp.
<220> FEATURE:
<221> NAME/KEY: misc_feature
<223> OTHER INFORMATION: Nitrite Reductase Terminator

<400> SEQUENCE: 22

```
taggccagtt gcgcatgtgc tgcgcgcact gggacccaag cagttagtgc aggcctacaa     60

gcgcgggga tgccatattg tatatgtttc tattaggcat tcgggcctgc cacgatgcca     120

tggaggcgca actacatgag atatagacta gtttgtcact gatgcggcca tattaaagag    180

tccatatgtt ctgccaccgg ctgggcgata ctgcgccatc accatgccta agcgtcatgg    240

aattcgcgag tgggtgcatt accagggccg ctgtctacta tcaatggaag atgggacggc    300

gttttgaagg ttgagttgtc gcccattacg agtggatgat gagcaaaaaa aaccgtgcat    360

gctttcacta ggcgcaacag gtattggttt ctttatcgat tggatatatc gctgcagcat    420

atgtcgtaat cgtcactatg tagtcgactt acagactgcc gggcatggcc atgatatgtt    480

tgcgtacatc aatcacaacg atacggtaag cacactgctt gacctgtgca catatgctct    540

agcagcagaa ggcgatatca gacaatcacc agaaaaggac aaacagaaag gtcctccaac    600

ctgtgcacac atccgacccc agcatcgtcc acgacgacca ctagcgacaa tacaggattg    660

ttcccacgac ccagcgctac tacgagtacg ctcccgaaca tgaacaggca ccggttttga    720

tatggactgg tacgatgacg aggcggatga tctgacaacg acggccgtcg acgagaccct    780

gcaaggggtt cactggtgcc agtcctgtcc cgggggcgcg ttcgaaagaa tggcgacaac    840

tgctactgta aaaactaaaa aatggctccc cgtactcgta ccaaaacccg taaaatacag    900

gaagacgctc tagagagcca tatttaagaa atatgtacga gagtaaatta agattagata    960

ttccattgag gacggaattc tctgaaattt tctgattgtc cttttttttgg tgatttcctg   1020

atatcgcctt ctgctgctag ctcatgtatt aagtataata tatatatgtt ccgatactcg   1080

tacagcacct ttccgtacgg ggcggtacgt gattggtaag tgtgctcgtc ctgccggtgt   1140

atatccgcct gttttcgtct gcccactaca ttgtctacta cattgtggag cgcacgcgta   1200

catagcgact ttactgctgc gcgtccgtcg atccataggc tatagcagcg tcgtcgaccg   1260
```

```
tccagcggac gacgggacgt cgtctgtagt acttgcactg taagcggggc ggataccggt   1320

acatcagtat gtgtggccaa tagcagccac ttcacatccc gccccgcacc ctggcctgcc   1380

ggtgtaaacc agaaccagca tcgccaactg tcgtcccata ccaaacaagc gggctgctct   1440

cgctcagacc cgccgtatct                                               1460
```

<210> SEQ ID NO 23
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Promoter

<400> SEQUENCE: 23

```
agatatatgg ggtgcaacat gcaccgtgac aagccctttg gctgccatcg ccgatgtgtt     60

agcgagtcaa aattgccaag acatgagctc cagcactata tttctatata ttcctctaaa    120

cgcagggggt aatttttgat tttggagttt taatcaatag aaatttacta ttcatcaaca    180

tggcacatgc agacaacgtt cttggcgggg tcgcgggggc gcgtgcggca cgtgatggtg    240

ctcctgctcc tgcatcgcgt cgctcgtcaa cctgtgttgc tatgacccgg gtcattggct    300

gcaagcgtcc tcgccgcggc tgatggccta ccctagggcg gtggtccctt tggtttttgg    360

cagcttggcg acttcgtggt tcccttggct ccttcttggt tcttggctcc ctggcctcct    420

gctcgacctt ggtctcaggc ttgtgtctct cttttgctgg caagctttca tagttgttgt    480

tagttcaatt tgtagtgcgc atttgtgcaa tccctgatgt aaaaatcaat ttactattaa    540

taaaaaaata gaaaatacca taaattcccg ggcccaggta ccggtagtac aggtagcggt    600

cgcagtcgct gtagaggacc tttctgattg tccgttttag gtgatttcct gatatcgccg    660

tctgctgcta cctcatgtaa ttagtacagg tagcagtcac aattaaaaag aaagaaatgc    720

ccgtattatt attattaatt tgttttatta ttatattttt atttttagcg gtacagtaaa    780

agtaaagtaa agttcgcccc gggacatcgg ccgaagccgc cccagcactt gacctcgtgc    840

gccaactgca gtcgtaggtc tggcatggcc catagaccat tgcctcattc gaaccccgaa    900

gggctaatgc atcaaccgag taaacccggg acacgccggg ccgatattgc cgaaatacat    960

cggccaggaa tcgaacccgg tacctctcgc acacgagacg accgctctac cgagcggaca   1020

agggatgtac cttgtaaagg tttttgccgg tattgcgggt acaggtactc gtaatccggg   1080

cagacggcct aggcgagctg ggaccagccc gcctatccgc acgttggccc ataattcagg   1140

tcctcattca attcgcgacg taccccggta ctgaatcact gcgtctttgt tacgagatga   1200

gacagtaccg gtacgaatat gcagtgacga ctaagctctc acggcccggc cggtctcgag   1260

ccgccgactt acatactcgt agtcactcgc tctacaactg agcgcccgag tcagcataag   1320

ttcccgggtc tgatggtggg atcgaccagg gaactcatac gaacgaggga tatctctcgc   1380

atacgagacg accgctctac cgagcggaca agggatgtac agtattcggt acagtactac   1440

ttggtttccg tatacagtga actactaagg gttgctgcta ccgttggaat taattaatta   1500

taattaatta atggtacgaa tattgcaaaa tcagtaatgt aataaacaac aatacagaac   1560

caatgccagt agcaatatcg tctggccttt ttgcaaattc acagcaccaa taccagcagt   1620

aggtactacg gcgggtacca gccgcctggg cacgggtaca ggttctcgca tggcaccggt   1680

tgaaaataaa taatgacatg ccgaattgcc gctatcgccc cgtgatttcc gtgacaccgc   1740

gccccccccc ccctgaccgg tacctgcgct gctagcgact catcacgcgt ggggcgccag   1800
```

```
caccagcagt tgcgcatttg gcatatattg agcgttcaat attttccggt tcaaaatagc   1860

ccgtcccaca gccccgcccc tacccactcc cccctccac gcccgcccgc caatctccga    1920

caccccgcta gtagctggcg tccctccacg cgctaccgca ccgcacctcc gccaaaaacc   1980

tcagcccata gcgccacagt                                               2000
```

```
<210> SEQ ID NO 24
<211> LENGTH: 1803
<212> TYPE: DNA
<213> ORGANISM: Tetraselmis sp.
<220> FEATURE:
<221> NAME/KEY: misc_feature
<223> OTHER INFORMATION: Nitrite Reductase Terminator

<400> SEQUENCE: 24

taggccagtt gcgcatgtgc tgcgcgcact gggacccaag cagctagtgc aggcctacaa     60

gcgcgggaga tgccatattg tatatgtttc tattaggcat tcgggcctgc cacgatgcca    120

tggaggcgca actacatgag atatagacta gtttgtcact gatgcggcca tattaaagag    180

tccatatgtt ctgccaccgg ctgggcgata ctgcgccgtc cgcatgccta agcgtcatgg    240

aatttgcaag tgggtgcatt aacagggccg ctgcctacta tcaatggaag atgggacggc    300

gttttgaagg ttgagttgtc gctcattacg agtggatgat gagcaaaaaa aacctgcgtg    360

ctttcactag gcgcaacagg cattggtcct ttatcgattg gatgtatcga tgcagcatat    420

gtcgtaatcg tcactatgta gtcgaccgac ttacagactg ccgggcatgg ccatgatatg    480

tttgcgtaca tcaatcacaa cgatacggta agcacactgc ttgacctgtg cacatatgct    540

ctagcagcag aaggcgatat cagaaaatca ccagaaaagg acaaacagaa gggtccaacc    600

tgtgcacata tccaaccccg gcatcgtcca cgacgaccac cagcgacaat acaggattgt    660

tcccacgacc cagcgctact acgagtacgc tcccgaacat gaacaggcac cggttttgat    720

atggactggt acgatgacga ggcggatgat ctgacaacga cggccgtcga cgagaccctg    780

taagggtttc actggtgcca gtcctgtccc ggggccgggg ggggaaatgg cgacaactgc    840

tgttaaaagt ggctccccgt actcgtacca aaacccgtaa aatacaggaa gacgctctag    900

agccatattt taagaaatat gtacgagagt aaattaagat tagatattcc attcccgcag    960

tcgatgtaga ggacctttct gattgccttt tattttggtg atttccgata tcgccttctg   1020

ctgctagctc atgtaattat attccattga ggacctttct gattgtcctt tttttggcgg   1080

tgatttcctg atattatcgc cttctgctgc cagctcatgt aagtaaagta aagtaaagtt   1140

cgccccggga catcggccga agccgcccca gcacttgacc tcgtgcgcca actgcagtcg   1200

taggtctggc atagcccata gaccattgcc tcattcgaac cccgaagggc taatgcatca   1260

accgagtaaa cccgggacac gccgggccga tattgccgaa atacatcggc caggaatcga   1320

acccggtacc tctcgcacac gagacgaccg ctctaccgag cggacaaggg atgtaccttg   1380

taagtattat agacatattc cgatactcgt acagcacctt tccgtacggg gcacgtgatt   1440

gacgtctgta cgtgattggc aagtgtgctc gtcctgccgg tgtatatccg cctgttttcg   1500

tctgcctact gcattgtcca ctacattgtg aagcgcacgc gtacatagcg actttactgc   1560

tgcgcgtccg tcgatccata ggctatagca gcgtcgtcga cggtccagcg gacgacggga   1620

cgtcgtctgt agtacctgca ctgtaagcgg agcggatacc ggtacatcag tatgtgtggc   1680

cagtagcagc cacttcacac cccgccccgc accctggcct gccggtgtaa accagaacca   1740

gcatcgccac ctgtcgtccc ataccaaaca agcgggctgc tctcgctcag acccgccgta   1800
```

```
tct                                                                 1803

<210> SEQ ID NO 25
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 25

aaacagattt aaaaatctgc aagccgcgta aaagcgggcc gctgactact ggtgtgcatt     60

acaaaaaggc cggtacccaa cccaccgcta aaagttgcat taccccccaa aaaaaaaaaa    120

aagcagcact acaagatcag caatacagta caagccgcgc ctacaggccg cccgcatccc    180

gcacgaggcc gcgcaggtcg ggccggtcgt caggtctacg ggggcgggca cggcgcgaat    240

cgccacgccc gccgcctgta ccggcaccgg acgccggacg gcgtcgttcg accgtcgccc    300

gtccgtcgac ggacgccggg ccccgggtcg gcggactgcc cccgcaccgc ggcgacccct    360

ttttacagca tcatgttaca gcatatcctc ggaccaccgt gtatatagtc gctgtataaa    420

tatagagggc gagtctcgct tgctgattca gcagtaaaaa cgcgctgcgg taccgcgtta    480

ttttggcgtt ttagacgaat atatgacgtg cctgggctag aatacacgcg catccattca    540

gaatcttgcc gtcttcggac cagtgcctag aaatcaaacg agcgaacact gaacgtatga    600

cggttcattc acgaagacgc agcacaggag gacggaggac ggaggacgga cattcgtgat    660

ttttgcagta tgtttccggt ataattcacg atagatccgt cttagtcgca ggattttaac    720

ggactgtggt aggagtgcct agaaatcaaa cgagcacaga tcgaacgtat gacggtgcat    780

tcacgaagac gcagcacacg aggacggagg acggaggacg gaggacggac gcctaaaact    840

ccgtgataaa accgtattgc gaccggtatc aattcttacg tattccaggc gatttcggac    900

gcggctctcc ttttcctccg ctcaacccaa gaggtagggg aatcgtctgt aatgcgtgac    960

atccgcgaac cgatccacac tgggaatcga tccgtggact ccgcgctgtc aaaagcgcgg   1020

agggtccgtg gatgacacac tgcaacagtg tatcgtaaca atatcttctc atcacaacag   1080

gtatcagtac cgccgtaccg tacatgtacg atgatacatg agctagcagc agaaggcgat   1140

atcggaaaac atgtacgatg atggaacgcg tggacggcgt ctgtggccga gaattgcacg   1200

tgcaacgatc cggtcacgat ctggacgtac atggtatcaa tgattaatta ataaggattg   1260

tgagggagta ctccctgcgg ttagcgatta tgcctagtcg ctacaggtac ctggagttac   1320

acttatcgcg atcgtcattt taattaaatc ctgagacggg accggaagga atatgcacta   1380

ctgaaataaa cattatttat gccgtacctg tagcgactac cggtacctgt agctatgtgt   1440

tttcattcgt agtcgtcgct gcctcgtccg tccatctgcg tgagccgctt ctggacgttt   1500

tggacttatt catcgtccag ccagcttcat cgattattta attaaatcaa tgtgagcata   1560

catgttgaaa aatcgtcatg acaagtaccg gtcagccggt accggtaaat aatttaaaca   1620

gcatattata ctgcaccgca tgaccctacg accgtgacag taggtatgcc agtgggggtt   1680

tatataatta atgtgctcac atatatgtat tataattgcg caatgaattg ctgccaatta   1740

tgttagcgct atgtggtcgc tgctggtgac ggctgcgccg gattaatatc ccacggctca   1800

caacatttcg cgccgccgca catggggtgc ggatacaaga ccagcggggc aaatcttgcc   1860

gtatcacatt ccgtcttccc cctcccccac ctgcttccct cccatccacc caacacacta   1920

ctctcttcct acttttctac tgtccctcca caccgggcca cttgcatctg gcaggaattt   1980
```

```
cgggaggcga cgcggataca                                              2000


<210> SEQ ID NO 26
<211> LENGTH: 1501
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 26

gaagtaatat agcgcctgca cattggttgt cagataccct ctgactgccg caccctgctg      60

gggcgcagaa ataatcggcc tcactgagcc atctgagtag agcttatgta atttatcatg     120

atgtgcgaat gcatctcctg gcccctacgc catgggcatc tgcactatgg gatctatatg     180

ctttgacacc agggtgcctc tttctcctgc tgacatgata agcgggccta cacacatttt     240

ctttcccgct gcgtttgata tatcctgaat cccattaaca gtcgggcgga aatgtggaca     300

catgggccca cagcgtgcgt gatacccaac cgccgttgca ctctaggggt ggtgacgtcc     360

tcattggggt ggagtcatat gctctggcgc ttacattgga cataagttac ctcataacat     420

tctaatttcc atggtgactt ttgtggtgaa tgtcgttcct cagcggtata tgaccccgga     480

cacacagtcc agcttgtaaa ggggttgcag gtgggagtca gatgacaaga gtaaaacagc     540

gcgctccgcc tgctcctggc attcaccagg gccgaagctc catgcggtgc ggtgtcatct     600

gccatgctgc gcgcccgatg ctgacggcgt agcccccccc agagtgtcct gatgcggcgc     660

gtggcgctga aaatcgcgag gccacaagtg aaacagccga ccgcttgagg ggcgcgagct     720

gccgcttgat ctcgtcaatc gacggctgct cccccgcaca cgccaccgcc ctcagcgcaa     780

cgcaaagaat cttgtggtac agacgcagca gattttgctg cgaggcgacg ccgcctgaca     840

agatcgctgt gagccactcg gcgctcccat cggcgccatg tgcaggttcc tccgcgggtg     900

actgcctgtg gccggtagca tctgcttgcg acgcactgag tagaggacgc acagcggctg     960

catccacgct ccctgttggc gcacggcgga aacgcagccc cgttcctctg ttgttggtga    1020

gtgcgttgct gcccgcaccc acccgctgac gtttggggcg gttgatccaa caagtcatat    1080

atctgattag cggttgcgat gacctgtgca attccacgtt gcgcacaggc gcaaaaactg    1140

tcaggtattc tctcatctgt tctgcgtgag acacccctag gatttcacac aagacgtatc    1200

gtctcccaca atgtctcgca caaatgtctc tctcaaagac ctatcctatc gtggtcaaat    1260

tacgtcttat ctgcatgtca gtaatcacta gaatgcgaac cgcagtcccg ccccaaagac    1320

tgttgcatac acttgtactc agtcttggag tcagatgggc accactatcg ttatcagagg    1380

catgccattc ctcatgcatc atatgtgatg gcaggtaggg ttctatggac gctacaccaa    1440

tcacgagctt catgtttgct ttcacgccgg cacttaaatc acggtgcatg tcatgtgtca    1500

t                                                                    1501


<210> SEQ ID NO 27
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 27

gcgcgcacaa gtacgcgaag ccgctgccga tggcaacgag ctgaaagatg gcagacgagc      60

tgctggtggc tgtcctaagt agttccccgg tcgggagcgc agggctcgcg ggcgatgggg     120
```

```
cagcccttac tgaaacgcga tgttattgga tacctaaccg gttaaaacca ccaacagacc    180

gtaacagtaa tttaacatat tttgcaccgt gtatttcatt ttgcaccgta gggtttgatt    240

ataccctagt tcccgggtct actatcagta cttaagactc acgggtggtg tagcttgggt    300

ttgtagaact agggtgcatg gcggcattca tcagcgtgca caccagccgc gatgcatatc    360

caatgctggt tttggagcat tttgtacaag atgggacaaa gtgggggcaa gtcaatatta    420

ttattatgat taaatccatc gccgcgtagc cacaagacgt tgctaataga ttactctttg    480

agcatcccca actcaagcaa gtccttcttc gtggctgcgt taaacttgac gactccgccg    540

ggtttgcgtt gcgctggggt ggctgacatg acatggacgc agttgtttcg tggctggctg    600

atttgccacc ctgtttgcgc gtatgtcttc acaacttgaa cggcgtacgg gtcgaactgg    660

gacagttaaa ttgttagaaa attccacgtt cggaaatacg tttagatcaa aatatctcct    720

cacattccat ccccctgtaa ggtaggtgta ttggttattc ctttcgccgt ttccgagttc    780

gcctcgctgg ccccggacgc tgtggccttc tttgtggagc tcgcgaaagc tagccacaca    840

cagcacactg accaaaaaaa tcggccagct cttgtctacg tggcgcatca gccgtttctc    900

cttgctcatc aacatggcac atgcagacaa cgttcttggc gggatcgcgg ccgcacgcgc    960

ggcacgtgat ggtgctcctg cgcctgcgtc gcgtcgctcg tcggcatgtg ttgctatgac   1020

ccgggtcatt ggatgcaagc gtactcgccg cggctgatgg cttacccccg ggcggtggtc   1080

cccattgttt catattcccc atttggtctt tctggtcgtt ccttggcttc gatgcttccc   1140

ttgacccttt ggttcatggg agcttggcga ctttgtgatt ctcttggctc ttccgtggtt   1200

cttgactcca tggcctcctg ctcgcccttg gtttcaggct tatgtctctc ttttgttggc   1260

aacctttcat agttgctgtt agttctgttt gtagtgcgcc tgtgtttaag gctctgatgt   1320

aaaaaatact tattggcact tagttagcca cggtattcta tgtcactgtt agttggtcat   1380

atcgtggttt tcgtgataca gcattgttag ttgatcatat catatcatat cgtctgtaat   1440

gcgtgacatc cgcgaaccga tccacactgg gaatcgatcc gtggactccg ctttgtcaaa   1500

agcgcggagg atccgtggat gacacactgc tacagtgtat cgtaagaata tcttctcatc   1560

acaacaggta tcagtaccgt accgtacatg tacgatgatg gaacgcgtgg acggcgtctg   1620

tggccgagaa ttgcacgtgc aacgatccgg tcacgatctg gacgtacatg gtatcaatga   1680

ttaattaata aggattgtga gggagtactc cctgcggtta gcgattatgc ctagtcgcta   1740

caggtacctg gagttacact tgtcgcgatc gtcattttaa ttaaatcctg agacgggacc   1800

ggaaggaata tgcactactg aaataaacat tatgccgtac ctgtagcgac taccggtacc   1860

tgtagctatg tgttttcatt cgtagtcgtc gctgcctcgt ccgtccatct gcgtgagccg   1920

cttctggacg ttttggactt attcatcgtc cagccagctt catcgattat ttaattacag   1980

gtaaatcaat gtgagcatac                                                2000
```

<210> SEQ ID NO 28
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 28

```
gaagtaatat agcgcctgca cattggttgt cagataccct ctgactgccg caccctgctg     60

gggcgcagaa ataatcggcc tcactaagcc atctgagtag agcttatgta atttatcatg    120
```

```
atgtgcgaat gcatctcctg gcccctacgc catgggcatc tgcactatgg gatctatatg    180

ctttgacacc agggtgcctc tttctcctgc tgacatgata agcgggccta cacacatttt    240

ctttcccgct gcgtttgata tatcctgaat cccattaaca gtcgggcgga aatgtggaca    300

catgggccca cagcgtgcgt gatacccaac cgccgttgca ctctaggggt ggtgacgtcc    360

tcattggggt ggagtcatat gctctggcgc ttacattgga cataagttac ctcataacat    420

tctaatttcc atggtgactt ttgtggtgaa tgtcgttcct cagcggtata tgaccccgga    480

cacacagtcc agcttgtaaa ggggttgcag gtgggagtca gatgacaaga gtaaaacagc    540

gcgctccgcc tgctcctggc attcaccagg gccgaagctc catgcggtgc ggtgtcatct    600

gccatgctgc gcgcccgatg ctgacggcgt agcccccca gagtgtcctg atgcggcgcg     660

tggcgctgaa aatcgcgagg ccacaagtga aacagccgac cgcttgaggg gcgcgagctg    720

ccgcttgatc tcgtcaatcg acggctgctc cccgcacac gccaccgccc tcagcgcaac     780

gcaaagaatc ttgtggtaca gacgcagcag attttgctgc gaggcgacgc cgcctgacaa    840

gatcgctgtg agccactcgg cgctcccatc ggcgccatgt gcaggttcct ccgcggatga    900

ctgcctgtgg ccggtagcat ctgcttgcga cgcactgagt agaggacgca cagcggctgc    960

atccacgctc cctgttggcg cacggcggaa acgcagcccc gttcctctgt tgttggtgac   1020

tgcgttgctg cccgcaccca cagctgacgt ttggggcggt tgatccaaca agtcatatat   1080

ctgattagcg gttgcgatga cctgtgcaat tccacgttgc gcacaggcgc aaaaactgtc   1140

aggtattctc tcatctgttc tgcgtgagac accctagga tttcgcacaa gacgtatcgt    1200

ctcccacaat gtctcgcaca aatgtctctc tcaaagacct atcctatcgt ggtcaaatta   1260

cgccttatct gcatgtcagt aatcactaga ttgcgaaccg cagtcccgct taaagactgt   1320

tgcatacact tgtactcagt cttggagtca gatgggcacc actatcgtta tcagaggcat   1380

gccattcctc atgcatcata tgtgatggca ggtagggttc tatggacgct acacccatca   1440

cgagcttcat gtttgctttc acgccggcac ttaaatcacg gtgcatgtca tatgtcatct   1500

acttttgcca tgcatgcacc aagaatgcac gcacctctgg cggaaaacca cacgactcag   1560

caagccggat gccatacttc ttctgagcaa ctgttccggg ctccagtctc ctcgtaaact   1620

gaagctcgtc tgactgaaca tcgatgccaa aattcctgcc gcccaccaca acacaatgca   1680

gtcaatgctc cacccagcgc ttgctgccct gctgaacagc tcaaatcagt gaaaaaaagg   1740

tgcaattgga caggagataa catggaattc atgagggcag aggggcaagt agccaattca   1800

ccagattctg gccctgcttt gcgctagcgg aagttccgct agcgagggga agtgcgtggt   1860

gaaaatggtc agcgcgccag atgatatgag ctcctccgcc actgcgactg aaagcgccaa   1920

tccatcggtg gtagatgttg acctgctcat catcatccat tatcgcgggt cagggcataa   1980

aatgtaccat atccatcatc                                               2000
```

<210> SEQ ID NO 29
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Promoter

<400> SEQUENCE: 29

```
cccgcgaatc ttcgctttac ggcacaccca tatgaacgcc catcccctcg acgtcagaaa     60

gcctcagctc aaaacctgcc tcgatcaagt tgtattcctg tgagagggct tctagtagag    120
```

```
ccactcacat cgaggtttga ggttgcgacg gcgatgcatt ttgctaaacc gaattgctag    180

tcgatacacg ctccaaaaaa tgtggattga ctagccttga ctcgaccttg agcgcgtgca    240

caattgggct acagaattga gggggtagta catgcacggc gggttataca ctagtagtct    300

tggtactgtg tcgacgcagt tcaatggaat cttgcgacgc catggtgagt cggtggggct    360

tttttagcgt ttcctagcgc tatgtcactg cggctacgca gcctcctgcc gagccgatgc    420

gccaccattg ttagcttccc ttgacaatat tccaccccta tagtagaccg aggtatggga    480

tgcccttgtg gtgcccgctt ggcgccccag aggcagcggt gtgtggcttt gttggggatg    540

ggggactgtt ggatattgga aaattgtatg ggtacttgac gtcgtacggc ggataggtaa    600

atgacggatt attatccttg cttggggtgc agtgtgaggt ggctttcctc ctctttgcag    660

ttgataccct tgcggtagag gcgcatctat accatgcatt ggagaacatt gttgccggtg    720

cacactcatg caaaggagct aagccgctag tacgggtgtg tgacaatatc ggagcaaaaa    780

agcgggcgca acaaagcagg ttaaccacgc ggagagagca acattttagc attagccagc    840

atgcgcgacg cacgaccatg gcacccgcca tgcgcatcgc aggcaagcgt agcgtgcgat    900

aagtgtagat taataatatg atatgtaatc gtaacattgt ggcattgatt catccatcac    960

cacacatcca tgatattaat ggtagccttg catcggccgg gagcgcaagg ggtttacaat   1020

tccacactgt aatcatgcgg ctttttcttc ataattgtcc tatatgaatc ttgcgcatgt   1080

attgcatgtg gcaataggtt gcttgccaat gtgcactagc ttgacatcac cactagcatt   1140

tcgtatcata gcccaataat tgctaaatca actcctgcat cttttgaagt gttttggcag   1200

tactttactg tagaacctgt gaatgcagca ggagagaaaa agggccgctg aaaaaggggc   1260

gagggggggg gggggggggg gcactcaaaa taacaaatca acttgtcatg gcattacaat   1320

gattcataaa caaggatata tatatacatt gtgctttcta atacgctgtg cagtacgtgg   1380

atcatggacg caacaccatt cataagctgc cgttatgaat ccaaatgact gagcctggcg   1440

ggccatcacg cgcgcgcaca cgtgtgtaca ggtactcgta cgatattcag tatcgcttcc   1500

gttcgtcgaa ctattattta tctatcgtaa gtatatttaa ttatatttac gggtatctgt   1560

cgactactat ccagtcgcta ttccccgtgc tgtagcagac tagcaggact ggacgagggg   1620

tagagtacac caccactcgt ggttgagcgc ccggtgtata gcgactacta atccggtata   1680

tgaggatcgt actaaaaaat agttcatccc atcgatcagg gcactatttc agcgccggct   1740

gcacatagaa atagccaggc gcacgtcagc ctgcggggac cccactcatt catttttccg   1800

ccactccgcc acttcgagtc tgctcgagct tagccatctc accctggcct gctgcaaagg   1860

aggactgtct cctgtgcgac agcccacagg ggtgtcatag ctttccttcg cctcgagtca   1920

caaggcatat cgcgccaagg ctcgctatcc gcccgttggc gacgtccgcc gttgaaaagg   1980

ccggaagata tcttcaaccg                                               2000
```

<210> SEQ ID NO 30
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Terminator

<400> SEQUENCE: 30

```
gctggcagcc tctactgcgg caaacgaggc atggatcgcc aaatcctcgc tgctcgacct     60

cattggcggg tatatttgcg cttctgctgg accatggatc aagacccgga tgtggcggct    120
```

```
gcggtgtcgc attattagca gtagtactgt tgatatttaa tgcacatgtt tgtgcttaga    180
cgcaggtatg tatgtaagac atgcaacaag attgctgtag atttgttagt gtagcacgcc    240
aatcgcatgc tgtaaaattg cagaggcgtt cttggcaaat gtgatggctt ggttccactc    300
gccatcagag gatgtcggct tcattgactt aatttgcaga tactgtggca acttcaagca    360
tccctgcgtc gaggcgttca gcaggctatc tgaacgcatc cctgtggctc tgtgcagcat    420
ccaacgattc tggaggcacc gccactagtt taccgactca acatatagga tatggtggtt    480
aaggtcgcaa ttcccatccc tggagatcgg agaagggagg tctatgcgta attgcgtacg    540
tcaaattccc tatgcatcag tactcaacgc tccgttctag ccacgatcgt ctggcgtcgt    600
acacgacccg tcagattgcc cccgcgggag ccttcctttg ttttcaattc aattctctct    660
gtcgcgactg gttttcacaa ccgcctccac actcaacaag tggagctcat tcgaatcacg    720
gttgaacatt aaccactgtc gtgcacgtat aataaacgcc tctatcttcg ctgtctactt    780
gtactcgttg tatcagcatc gtccgcccgc gagcgctgga ccgtcctatt ttttatagcg    840
ctagtaccac tattttatta tttttcttga aatagtcata ccaataataa gctcatgtat    900
cggggtattg gtgtagcgct cgactgaaac cgacacatat atcacggttg tggcgctgct    960
gtagtcaata acggcttgct gtcgttcggt gtagcatagg caccgaatcg aacaaatatc   1020
acggccaacg tttatggttc ggtgtaacag ttgccgaaac caacccaaaa taatcgcaga   1080
cgatttcgtt tctggtacgg tataagagat gccgcggaaa acattgatat acgcctaact   1140
agaagtattt tgtggttcgg tgtatccatc caggacggta gtataacata cacctctccg   1200
cataagtccg ggttttgaat tctcgatcgc aaagcgcatg catgggcgag gataccgccg   1260
gctgcatgtg catacacgct aactgcagtg ggaagagttc gggcaaacgc atattgtgcg   1320
ctttataccc acccgcgcga caacacgacc atttgtgggc gccctttata aaatgcgaaa   1380
tcagtgcatg atgcgttggc gctagaaaat tgcgggttgc gccaaccgtc caaacctatg   1440
gaaatagcgt cactcgtcgc accaaactcg atgaatacgg cccttggcat aagttgcaca   1500
caccgtgcgt gtagtccact gaaagcatgt cgctataggc acgccgtgac accccaacgt   1560
taagttggct actgtgggga gcagttttgg ggtgaaaatg ctgctgtttc tgtggcgaac   1620
gcatgtagga gaggcgctcg atggccctct tggtgtaggt caatgctcta ctatgggggc   1680
gcgtggtgga atgccagttg caccgtttcg tgggcggggt ggcgcggtag gggcgtggac   1740
tttaataaat atgaacttcc ttgaaaaatg ctgtggaaaa tggcattttc cctggtagat   1800
gtgtgtatcg caaggaggcg gcatatccca agtgttggtg gtctatagtc atccacacac   1860
ataacgctct cgcgcaaccg agtatggggc tcagacacgc acgtggcgga aaggcacgcg   1920
cccgacatgg gtgggcacat gaggcagtga ggagcaactt ggatgatcat ctttggggat   1980
tttttccggg gcccccagaa                                                2000
```

<210> SEQ ID NO 31
<211> LENGTH: 658
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 31

```
ggcctgagct ggcagctggc ggagatcacg gagcgcgaga cgccgcggtg ggcggccaac     60
agcagcaatg acaaggccaa gcactggtgc tgggtgcgcc cccgtccccc ccccccttccc   120
```

```
ttttccccac ccaacactac cccatccata tatccatgta aaaccctagt tggggctcgc     180

ccagtggtta ggttgttgct ataggtgtcc agttggggga ggaaggatgg atgggggagt     240

ttttgggggt ttttgtttgt cccaggggcg ggaaaaatac ccccatccat cgttcctccc     300

cggactggac acccatcgca ataaccgagc cactgggcga gccccatata gggtttcaca     360

ttagctgaaa cagcgtgaac ctgatataaa gatcctaaat ccttgcatat ttcaaaacaa     420

cctaagctca gcctagctct aaatcaaacc cacgtcaagg gcctgacacc gatagcccta     480

gaactgttaa cctcgctagg tatggcaact actcctgacc aagtttagtc attgggtggg     540

ccacaatcag ggttctgggg cataccctaa ccttatgccg aaacactggg gctacttcaa     600

ccctacaatc agacctgcat tgcaaccctg attatgcccg catatcctaa accctggc       658
```

```
<210> SEQ ID NO 32
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 32

tcgcatagca gactggccgt gtgaacacgt tgtgaacacg tgactgggaa tgcgctgtac      60

ccatttaagt acgctgccac ccgctttctg tgcgtcagtt ccgtcctgtg tcctgtaccc     120

gttatcctga tgcttgcccc cccccccccc cccccccccc caaacatgta ttttcctgaa     180

cggcgaatat tcgctcacgt tcaaaagaca gcacacttgc agcaacccct gcagtttgga     240

gcaaggccct tgagattatg atgaatgcag caacggacaa atgaagcaag tgtagccctt     300

gcaggtcttc atattattgt ttaatttata tatcaatata tgcacattca aaatatgtgt     360

atctatgaat aatataaata actatctacg taaaactaca tataactgta tatatagtca     420

tgtatttacg tgactatgtg tgtaactaca tatatatgtg tatacaactg tatatcacta     480

tatgtatgtt tacgtatatt tatatatgtg taaaagtaat caaaataaag cagcaaatga     540

atgcgttgat tgacgcgcgt gccttgtgat attattcgca aactgcactg gtcgctaact     600

gttacacacc tccacaaaaa tggtgtccaa aattataaat tattggagcc gcagtgtcgt     660

ggtgccgcct gggctgctgt agttggtcat ctgcgcaatc gacatcactg gtgtacttgc     720

gcagtgcgga tacttcaacc agcagtcggg acgacacgaa ctcataccat accatgcgtg     780

cccagcaagc gcctcgtcat caccgctcaa cagcccccaa tgcagcagcg gcgccgtcac     840

gcagcagggc cacgtccgcc accccggcca ccagctatag ccggcctcga acaggtcgcc     900

tgcgctccgg ctgccggcgc ggaaacctga cagcagcttg ggctgctggc ccaggtgctc     960

ctcgatgcgg gtcatcagcg cctgcacctg gttgcaggca tcattgcgca ggggaggagg    1020

gggggggggg ggagggtcgt gaggaaagaa aggcttgatg gctcgttgcc gggtaagcaa    1080

cagttcagaa cacaacatcc gaggcgcatt gctgctttgg aattgggcgg gcggcatgtc    1140

atgcaggtag ttctcatata tacatacata tacatatata tgtatatatg tgtatgtatg    1200

tatatctata catatatatt aatgcataca tagatataca gacatatata cacatataca    1260

tatatgtgtg tgtatagtgt acatatatat ggtatgttaa aaagcttgtg ctttattcta    1320

cttcagcgca tatatggtac tggatacgat acgacatcgc tcgatgtgat atatatatag    1380

cttaacattt tttcgatgta gcttgattta aaaataagta tccatactgg ataaaataaa    1440

tatggggata aatattttat tgtactcttt ttatttcaag caatagtcgc taattgtttg    1500
```

```
acggggaatg ggggagggag taggcagtat gcctcaggac tgtccacgcg gcccagctgc   1560
cctgcgctag cggagaggtc cagcgggccg acaaagactc cgtcgaggcc atcgatgccc   1620
agaatggccg ggagggcgtc caccgccgcg gccgtctcag tttgtacgag gaggaggagg   1680
tcgtcccggc actgctctga gtactccgcg ttggtgccgt accgggacgc gcgcaccagc   1740
gggtacgcca cgccacggcg gcccttatat tgtggtgggt agcggaggcg cagacaagag   1800
ggtgtcagag cagacctaca cgaaagacgt taacagtgca gcatgcggcc ggaacaacct   1860
agcaaaccct aatctcaaaa aaacatacag ccggagcaga caccagtacc ggtacccggg   1920
aaccgcagga gtatagcgct agtagagata cccgagagga gtttagtcaa gttaccccag   1980
taataacagt accggtagca                                                2000
```

<210> SEQ ID NO 33
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 33

```
cggggggggta catcgtcatt cacctccctc ggagggccca cttgcccaca tagcgaacgc     60
atcctcgaac gacaccacgg cggaacgcac acgtgtctcg atctgctcac cctagttccc    120
tttttccttt tatttgccaa agaactgttc gagttcggcg tgcggcgggg ggggacctag    180
tcagcgggga agtcgatgcg tcggggtgct gcaactacgg gtagtcggct tcaaccctaa    240
aaccccgttc acgagggggc gggcgacggt tagggcgcat ggccccttgc atgcgttcgc    300
tgtgtcctcg aaggccctcc agatagcgcc ggtgagatgg aatattccgg ccgtagtaaa    360
gaatctcgtg aacgggacac cgtgggtgcc cacctcggcg gctgtcctcc caacccgaaa    420
cttctcaaag tagtcaagca aatcgttgta tagccagtgc tcagtggtca ttttcttgaa    480
gtcgcgccga ggggggcaag cacaacccgt cgggactttg cgcagcgtaa agcctatcta    540
atgcgttgac aaggtttcag ctgcgaggtt gtcatgctta tttaatgaga acattgaaga    600
tgaagttgtc agttgggagg gatatgcagt actcgaccgg gtgtagcacc acatctgtgc    660
actccatcgt gttgcccgtc cccaaccgct gcttcttcga ccggctatcg cgaggcgaga    720
cgtgcaccaa ctcctgcttc agcagcacct gcttgagcga aatctcctct accttgctgg    780
cgtcctccag cgtgagcaac agagttgccc cgtccggggc agctgcgatg cagtcttaaa    840
cacgtgcatg caatcgtagt tctccaccca ttcttggctc ttcaagagca actttttgta    900
ggtgttgcca agaactaagt ttatcgttcc acctaacgga aacgcggagc gtgtgcatag    960
gaaccggtcg tgacgacgac gccatggtgg tgcgcatgca ctagtacgtg agagttggcg   1020
gccaacatag attgctggcg ggcgctagaa gtgtgatgag gagcagtcgc cagtcggtag   1080
gaggtagctg gaaggtagct agatttgcat gcgggcgagc acggtggcaa catcggcggc   1140
ggcgcagaat aaggacaaat gggaggtgca cattgggctc tggaaggctg tatactgctt   1200
gaagtactaa ttgcaaaact ttcgcaagtt gcaaaacccc ctccgtttac acggataaga   1260
ctgacctaaa ccaggtcatt tgtcggaatg gcctaataat ttattttatc ataaggatta   1320
aatgtatttt atgtatcagc agcggggatg gataccgtat cgtacatcta taagcgatta   1380
atccttatac atcaataata atccctcacc tggcctcctg ctcgaccttg gtttcaggct   1440
tgtgtctctc ttttctgctg gcaacccttc acagttatcc ctgttcgtta tgtttgtagt   1500
```

gcgcattttt aaggccctga tgcaataatg ttacttacat gagctagcag cagaaggcga 1560
tatcggatga aatcaccaaa tctgatgtaa taatatcaat aatcctcaga ctgtcagaga 1620
acggatactg gtacgggtac ggccgggcgg ccagccgtac gtgcgtcata ccataaagga 1680
ttcatatccg gacactgcta ccctgtatat accctttcca ggtcctgggc cctacatgag 1740
catcagctgg ctcatcactt tgcggccccg cgctgcgcag ttcaactaag agtcgacgat 1800
gcgccaatac agttcggatt acatcgacga ctagacgatc cagcagcgag taaatctccc 1860
aactccgcgt tgcattcgca ccattgggta cctgttcacg cgcacaacac acacaacctt 1920
cagcttccat tcagtctcat atactccccg atcccacgag tcgccgaacc tgtccgctgc 1980
actgaataca gtccgtttga 2000

<210> SEQ ID NO 34
<211> LENGTH: 326
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 34
gtgcccccag cctgagcgca cctactaccg ccagaaatca ctctgttgtc ctgtccctcc 60
tggtcttgcc ctgcgctgtc gtgttatcgc aaccactctt ccgaaccagc cgcatgtcgc 120
tgtttattaa tcccccacaa agggagccat ctgggcttct atcaaagttc accatgaata 180
catggcatac aatctccaac cagatgacga aaaacaattc actgttttgt gacccgcaaa 240
tccaatcacg ggtgctgacg cacctctgag aaccattagt aaagggctca tattgggctt 300
gcatccaacc tatacggaca ttcgct 326

<210> SEQ ID NO 35
<211> LENGTH: 326
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 35
gtgcccccag cctgagcgca cctactaccg ccagaaatca ctctgttgtc ctgtccctcc 60
tggtcttgcc ctgcgctgtc gtgttatcgc aaccactctt ccgaaccagc cgcatgtcgc 120
tgtttattaa tcccccacaa agggagccat ctgggcttct atcaaagttc accatgaata 180
catggcatac aatctccaac cagatgacga aaaacaattc actgttttgt gacccgcaaa 240
tccaatcacg ggtgctgacg cacctctgag aaccattagt aaagggctca tattgggctt 300
gcatccaacc tatacggaca ttcgct 326

<210> SEQ ID NO 36
<211> LENGTH: 307
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 36
aggccctcgc cgacgccaac tttgacaccg gttccgttaa cccccccccc cccccccaac 60
accccccggc gaaccgagcg accctcctcc tgcccagtgc cttgtttaga tggcgcagcg 120

```
ccaccactgc cgcacatagg gcttggatgt atattgatgg tgttggcatc ctgccgctcc    180

gtatccactg taactgagag actcccaaaa atcacccggc atacgcctca tcgcatccgc    240

agagcacggt gcgcagcaaa ctgactgcca ttcaccggtg aatgttacat gcgaggtggg    300

ctgcatc                                                               307


<210> SEQ ID NO 37
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 37

tgaagacgtg gctgactgca ggaggtgagg gcgtcccctg aacaacctcg aggtcagcgt     60

ctaagtgggg gtattgggat gtgggcgttc aggactaaga ccacttagga acagccactc    120

tttggcttcc caaacgatcg cctaacagac tcttaggcat gtggtcttgt gtacgtgtcc    180

tggcctctaa gtctctgtct aagacttgct gactcttggc cttggttcct atgactcctg    240

tagaagtacg tctcacagtg ccatcggccg tactggccgg cactacacac gcgtgcgagt    300

tgcttggtta ctcggcgtga cagaggtgtg tgtgtgtggt cgatcgacgc gaaatacgtc    360

aagcactcct caccctgtgc tgcacgacat gcctcacgcg aatggactac gagtgcccgc    420

acgcgcgcaa tgcgtacgcg tacggtatca cgacacgact cgacgacgac gacgcgcagt    480

accgactgct cgcatatggc aacaagcaag ccagtgctga tcaggcacgt tcggcacgtt    540

aatcggtcgg tcggtcggtc gacaagtcca ggcagtcggt acgacgggtt cacaggaggt    600

aaaagcaaga cgggcgtcac gacgcaaaca acacaggcgt aaccgcgact caccaccgtt    660

gcttgctgcg cgatatcact cgcagctcga cagcaggttg tactgccctt gatggacagc    720

aatagacgaa gcacgtgcag gtgtgatgtg cacagagtct aggtgtttgt ggtgtagtag    780

tgtggttaca agatgggtgg gatgagacgt ttggaaagcc aaagagtggg cgggcagcgc    840

gccgacaggt ttctaaagca tcccgcgggc gcgcgagccg actaagcccc taggccttcc    900

tacgcgctat tggtctgcac gggcgccgtg gttggcggca gttagccgtt ggtacgggcc    960

ctaggtctgt cggtggttct aggtgtgaga gctgagcgac agacagttgg tcgttgcgcc   1020

atgggtgatt gcttgcttgg acatcaggca tacacataca acgcagtact gcaagtacta   1080

aaattgatac ccgtatgaca ggcgacgagt attcgccggt atgccaagta agcaagtccc   1140

cgtacgcgcg catgcgtacg ctgaaacgtt gtacgctgtg acagcatcac atgtacagaa   1200

attggtagcg aatctaaatt attccactgt ttgttattta ataacatgtc tgtcacgtga   1260

ctcctaatcc gcttgtgggg gtgggaattg caccggcggg tttgcattga aatttaaatc   1320

agacgcgcgt cggtcgacct cagcgaaggt gagtaaattc gccaccgcag ctaccggccg   1380

gccggatatc cggatggcgt cactaaaccc gtaccagtcg ggctacagac catgtaaatt   1440

acgcgcgtta tatgtatcag ggttcgcgga tgtcaacgtc caaatttatg atgcgctgaa   1500

ttaattacat gtagcgagca gctgaattaa ttcctggtga tgttgaaatt tcctcaacaa   1560

cgctgcaaca tcaccagtag ctgggtcgta cctgtagcaa gccatatgtt catgtaccaa   1620

tactatatta tgcccgtcat tcgtacattc gcaccacatg cagtacccgg agcgactctg   1680

gcaggtgcta cgccacaggg gaggctgccc tgagtcgcgg tggccgagga cgacatcaac   1740

caaactcatc acatcaaacg aggcgcgctg ctcaagcaac attctcacac gagatacaac   1800
```

```
ctcacactag gtaccggaac tcgaagcagc gagtcgcagc aagcacctcc gctcgacgct   1860

gagcgacata gcagcgacct aggcctccca agcctaggtc cactgctact ctactcttgg   1920

ttccagtcgc caacgtagca acccatatga agggtcgcta caactcagca ggtcacgtga   1980

ccacagtcgt acaaacagca                                                2000


<210> SEQ ID NO 38
<211> LENGTH: 822
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 38

tcgcatagcg gactggccgt gtgaacaggt tgtgaacatg tgactgggaa tgcgctgtac     60

tcatttaagg acgctgccac ccacgttttg tgcgcttttt gtgcgtcagt tccgtcctgt    120

gttctgtcct gatcagcaga ggtacccgtc atcctgatgc ttgcgccccc cccccccccc    180

cccccccca tgtattttcc tgaacgagcg aatattcgcg ttcaaaagac atacacactt    240

gcagcaaccc ctgcagtttg gagcaaggcc cttgagatta tgatgaatgc agcaacggac    300

aaattaatat acacactggc aggtcttcat cttaatatat ttcatttaca tatcaattta    360

tgcacattca agatacgtgt gtatatgaat aaatatatat aactatacat gtataacttc    420

atacagctgt atgtatagtc atgtatttat atgactatgt gtgtaactac atatatgtat    480

atacaactat atataagtat atgtatattc atgtatattt atatatgtta aaagtaatca    540

aaataaagca gcaaatgaat gcgttgattg acgcgcgtgc cttgtgatat tattcgcaaa    600

ctgcacgggt cgctaactgt tacacacctc cacaaatatg atgtccaaaa ttatacatca    660

ttggagccgc agtgccgtgc gtggtgccgc ctgggctgct gtagttggtc atctgcgcaa    720

tcggcatcac tggtgtactt gcgcagtgcg gatacttcaa ccagcagtcg ggacgacacg    780

aactcatacc ataccatgcg tgcccagcag agcgcctcgt ca                       822


<210> SEQ ID NO 39
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Promoter

<400> SEQUENCE: 39

tgggtgtggt cgcaaaacaa ggtgcaaatc ggggtattaa ggcaaattgc aaaacagggt     60

gacaggcggc cggcggcccg gcccgtaagc gacggtccgt cctcctatca cgtggcaagg    120

cgcagccgag ccgggtgagg tgacaacact gcgacgatcc tctaggctta atgaacgcgt    180

ggtacatccc ttgtccgctc ggtagagcgg tcgtcttgtg tgcgagagac ccgggttcga    240

ttcttggccg atgtatttcg gcaatatcgg cccggcgtgt ctcgggttta ctcggttgat    300

gcattaggcc ctcggggttc gaataaggca atggtctacg ggctatgcca gacctacgac    360

tgcagttggc gcacgaggtc aagtgttggg gcggcttcgg ccgatgtccc tgggtgaact    420

ttacttaacg aacgcgcacg cccataggaa tcgccacact tgcgactggt gaggcggaaa    480

ggcgacgggg cgcgaatata agccgcactg ccgatacggg cacgcgcgac tggcacatcg    540

ccgttgctgc tcgcccgcgg cgaaaagcac acgcatcgcg cttcagccgg cggcagcagt    600
```

-continued

```
tctgggcgtg tgcaccaacg acccgcccca ccgtccgctg caggggtcgc gctccgagat    660

ttgtgcactg cttggcggcg ccggggggag gatccccggc tggaggtggt acatgggtcg    720

ctcgcaccat gttttacaat tcgtcatcgc accataaaag ttcgccccgg gacatcggcc    780

gaagccgccc cagcacttga cctcgtgcgc caactgcagt cgtaggtctg gcatagccca    840

tagaccattg cctcattcga accccgaagg gctaatgcat caaccgagta aacccgggac    900

acgccgggcc gatattgccg aaatacatcg gccaggaatc gaacccggta cctctcgcac    960

acgagacgac cgctctaccg agcggacaag ggatgtacct tgttaaaggt tttgccggta   1020

ttgcgggtac atgtactcgt aatccgggca gacggcctag gcgagctggg accagcccgc   1080

ctatccgcac gttggcccat atttcaggtc ctcattcaat tcgcgacgta ccccggtact   1140

gaatcactgc gtctttgtta cgagatgaga cagtaccggt acgaatatgc agtgacgact   1200

aagctctcac ggcccggccg gtctcgagcc gccgccttac atactcgtag tcactcgctc   1260

tacaactgag cgcccgagtc agcataagtt cccgggtctg atggtgggat cgaccaggga   1320

acgtcatcgc accatgtttt gaaaaatgcc gggttttgac cctgttctgc taccggtaat   1380

aatgtcagaa ttgtataccc tttcgcaggt ttccctaaat attattacgt tatacataca   1440

gtaccacatt gcagcaggat tgattttatt tacaatatta cctaacgacc tatatatata   1500

caatattacc tggcgagttt atggatacag ggtaccgccg cgtaggtagc agcacaaaga   1560

tgtgagatac gtagcgacta ccgtacgact gtagtaagaa taccggcccg ggtacaggta   1620

tagataccgg tacctggtac cagccacagc aatcgccctc cctaccggta gcgactattc   1680

cttagttaga tgcccaacaa gtgcggcttt ggactcttct gcaaacatcg cgcctgaatg   1740

gcgatgatcc gatgatccca ctgtcaatca aacatctaag tattgagtgt ctacttgtaa   1800

aggcagagct gttgtcacgt gcagagcagg ccagcggtcc ccctctggtg ttccgcgccg   1860

tggatccacg agcaagtgac actgccctca ctcgaagctc agcgctacaa agcacgcctt   1920

gtcaccgcag cgctgcctgc acccagggtc gagtgccatt tgccgcatta cattgactgg   1980

ttccgggttt ctgtccgaac                                               2000


<210> SEQ ID NO 40
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Terminator

<400> SEQUENCE: 40

gccggggggc gcgctgtatt cctgatcttg gctgtagcca cgtctccttg atctcaaccg     60

gtaacggcac tgatgtgacg tggctcagca taacctgcta tgtgcgagtc ttggaatccc    120

ttgggcgatt tccacgtgta aagctgtagc ctttgtggct gcagatcagc gcggcactgt    180

gccgtgtctg cactgaagag aggtaggtag cggtactacc cctcccaaag aaaaatgatc    240

tttgctgtaa tgcactcaat tcaggaccat gttgagtctg ctgcagtaag catgccacgc    300

tacgatcatg ccagcaagcc tgtgcccaca caatcctcca actgtcagta cctgtaagtg    360

tcactgtcct ggctggcagc attccgaatg cagagcttag cgactgctgg taggtacagg    420

tagtcgccat ttttttaaa atgagacggg caacgagggc ggagaaaagt tttccaggac     480

cccaacccga agaggttttc atgctcagaa cccccccccc ccccccctc ggcctacgca     540

ggcagggcac cctaaaatag ggactagcaa agttctactg tgaaacactg gcatacatcg    600
```

```
atcatggcat atattgacat gtgctgaggc tcgtattgat gtgctcctac tggtatgtcc    660

aggctaaaat atgattacat gtgctagatg caaaagattc ttctggattt tggctcttcc    720

gagtttggct cgttggcccc gcacgctgag gctttcctgg tggagctcgc gaaagctagc    780

catgcacacg ctggccaaca aatcggcaag ctcttgtctg cgtggcgccg ccgtttctcc    840

ttgctcatca aaatggcaca tgcagacaac gttcttggcg gggtcgcggg ggcgcgtgcg    900

gcacatgatg gtgctcctgc gcctgcatca cgtcgctcgt cggcctgtgt tgctatgacc    960

cgagtcattg gctgccagcg tcctcgccgc ggctgatggc ctaccccggg gcggtggtcc   1020

ctttggttct tggcagcttg gcaacttcgt ggttcccttg gctcctcttt ggttcttggc   1080

tccctggcct cttgctcaac cttggtctca ggctaatgcc tctctttgct ggcaaccttt   1140

cacagttgtt gttatttctg tttgtagtgc gcatttgtgc agtccctgat gttaagattc   1200

ttctggattt ccaggcgaaa gcataccctc accctacact gtcgttgtgt acgttgcgct   1260

tttactacat gcgtcaaaat tagtgaacgg gtaggtctta atccgtgcgc aggctgcacg   1320

ccacatatcg acaaaagtga ttgctgcccc acgggcatgt atcatcatct tccctcgagc   1380

tagccggccc taggagtcgc tcaatgaatg tgatggcatg tgatagacaa atacatactc   1440

atttgcatgt agcatggtga agtggtgcat ttttgccaga tttaaatgcg ttacataaca   1500

tgtacgcgtt gtacacatag ggatattcag agtatctcga agccctactc tgagcacatg   1560

cgaggttctg atgttacggc tagcttgcgt cgagagccca tggctgcgct gggcgtgtgc   1620

gcttaaaaaa tcagcgatgc ccgcgcgctg gtgcgcgccg gaaaaacttt aaccgccggt   1680

cggcaataaa atgcgcaaaa tcgcaaaata agcgcgcagc acatgaggtc acggtgcggc   1740

tgtaaactgc gtgctgtatt cagtcgcgcc cgctaagcac catggttcgc gcgcggcggg   1800

ccccctgatt gcgaggaaat ctgcccactg cgagacccaa acatgcgcac gggcgtgtaa   1860

gcgtacggag agcgccgctt aaacgctcag gccgcagccc gaaagtaaca atgtcgcttt   1920

gtttcgttgt atatacccgg taagtcgtcg gctccgtgct gcgagtccga gttgcggaca   1980

gtacgggaga agttggcccc                                               2000
```

<210> SEQ ID NO 41
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 41

```
tcttcaggag caacttattg taggtgttgc caagaactaa gtttatcgtt ccacctaacg     60

gaaatgcgga gcatgtgcat aggaaccggt cgtgacgacg acgccatggt ggtgcgcatg    120

cgctagtacg tgagacttgg cggccaacat aggttgctga cgggcgctag aagtgtgatg    180

aggagcaatc gccagtcggt aggaggtagc tcgaaggtag ctagatttga atgcgggcga    240

gcacggtggc agcatcggcg gcggcgcagg ataaggacaa atgggaggtg cacatggggc    300

tctggaaggc tgtatactgc ttgaagtact aactaattgc aaaactttcg caagttgcaa    360

aactccctcc gtttccacgg ataagactga ccttaaccag ttcatttgtc ggaatggcct    420

aatagtttat tttatcataa ggattaaatg tattttatac cagcggggat ggataccgta    480

tcgtcgtaca tatatatata taagcgacta attcccctac ctcttgggtt gagcggagga    540

aaaggagagc cgcgtccgaa atcgcctgga atacgggaga atcgataccg gtaacaatac    600
```

```
ggttttatca cggattttta ggcgtccgtc cgtccgtcct cctgtgctgc gtcttcgcgt     660

atgaaccgtc atacgttcga tctgtgctcg tttgatttct aggcacacct ccgaagacgg     720

cgagattctg aatggatgcg cgtgtattct agcccaggca cgtcatgtat tcgtctgaaa     780

cgccaaaata acgcggtacc gcagcgcgtt tttattgctg aatcagcatt cgaggctatt     840

cagcgactat tccttaccta cacacggtag tccaagtatg gtgctgtaaa aaggggtcgc     900

cgcggtgcgg gggcagtccg ccgacccggg gcccggcgtc cgtcgacgga cgggcgacgg     960

tcgaacggcg gcgtccggcg tccggtgccg gtacaggcgg cgggcgtggc gattcgcgcc    1020

gtgcccgccc cgtagacctg acgaccggcc cgacctgcgc ggcctcgtgc gggatgcggg    1080

ccgcctgtag gcggcttttt tttggactgt attgctgatc ttgcagtgct gccttttttt    1140

tttctttggg taatacaact tttagcggtg ggttgggtac cggccttttt gtaatgcaca    1200

ccagtagtca gcggcccgct tttaggcggc ttgcagattc aatctgtttt acaaaataaa    1260

taaatacgtc tcttttgaaa aataaattac tgagaaatct atctaacgct aaaagcatta    1320

ttacccggaa acaacagtat tacaggatca acactactgt acaagccggc taaaagcggc    1380

ccgtatcccg cacggccgca ccacgctcaa cccaagaggt aggggcacct ccacaaatcc    1440

ccggcgcgaa gcgccgctta gtccttatac atcaataata taatccctgg cctcctgctc    1500

gaccttggtt tcaggcttgt gtctctcttt tgatggcaac ctttcacagt tgctgttcgt    1560

tatgtttgta gtgcgcagtt ttaaggccga tgtaataata taataatcct cagactgtca    1620

aagaagggat actggtacgg gtacggccgg gcggccggcc agccgtacgt gcgtcatata    1680

ataaaggatt aatacccgga cactgctacc ctgtaccctt tccaggtcct gggggcccta    1740

catgagcatc agctggctaa tcacttcgcg gccctgcgct gcgcagttca actaagagtc    1800

gacgatgcgc caatacagtt cggattacat cgactagacg atccagcgag taaatgtccc    1860

aactccgcgt tgctttctca ccattgggta cctgttcacg cgcacaacac acaaaacctt    1920

cagcttcctt tcagtctcat atactccccg atcccacgag tcgccgaacc tgtccgctgc    1980

actgaataca gtccgtttga                                                2000
```

<210> SEQ ID NO 42
<211> LENGTH: 594
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 42

```
aggcccctcg ccgacgacac cggttcccgt taaccccccg ccccaacacc ccccccggcg      60

aaccgagcga cccctcctcc tgcccagtgc cttgtttaga tggcgcagcg ccaccactgc     120

cgcacatagg gcttggatgt atattgatgg tgttggcacc ctgctgctcc gtatccactg     180

taactgagag actcccaaaa atcacccggc atacgcctca tcggatccgc agagcacggt     240

gcacagcaat ctgactgcca ttcaccggtg aatgttacat gcgaggtggg ctgcatcagg     300

cccctcgccg acgacaccgg ttcccgttaa ccccccgccc caacaccccc cccggcgaac     360

cgagcgaccc ctcctcctgc ccagtgcctt gtttagatgg cgcagcgcca ccactgccgc     420

acatagggct tggatgtata ttgatggtgt tggcaccctg ctgctccgta tccactgtaa     480

ctgagagact cccaaaaatc acccggcata cgcctcatcg gatccgcaga gcacggtgca     540

cagcaatctg actgccattc accggtgaat gttacatgcg aggtgggctg catc           594
```

<210> SEQ ID NO 43
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 43

```
ctccctcgga gggcccactt gcccacatag cgaacgcatc ctcgaacgac accacggcgg     60
aacgcacacg tgtctcgatc tgctcaccct agttcccttt ttccttttat ttgccaaaga    120
actgttcgag ttcggcgtgc ggcggggggg gacctagtca gcggggaagt cgatgcgtcg    180
gggtgctgca actacgggta gtcggcttca accctaaaaa cccgttcacg agggggcggg    240
cgacggttag ggcgcatggc cccttgcatg cgttcgctgt gtcctggaag gccctccaga    300
tagcgccggt gagatggaat attccggccg tagtaaagaa tctcgtgaac gggacaccgt    360
gggtgcccac ctcggcggct gtcctcccaa cccgaaactt ctcaaagtag tcaagcaaat    420
cgttgtatag ccagtgctca gtggtcactt tcttgaagtc gcgccgaggg ggcaagcaca    480
acccgtcggg actttgcgca gcgtaaggcc tatctaatgc gctgacaagg tttcagcttc    540
gaggttgtcc tggttattta atgagaacat tgaagatgaa gttgtcagtt gggagggata    600
tgcagtactc gaccgggtgt agcaccacat ctgtgcactc catcgtgctg cccgtcccca    660
accgctgctt cttcgaccgg ctatcgcgag gcgagacgtg caccaactcc tgcttcagca    720
gcacttgcta gagcgaaatc tcctctacct tgctggcgtc ctccagcgtg ggcaacagag    780
ttgccccgtc cggggcagct gcgatgcagc cttaaacatg tgcaatcgta gttctccacc    840
cattcttggc tcttcaggag caacttattg taggtgttgc caagaactaa gtttatcgtt    900
ccacttaacg gaaacgcgga gcatgattgt gcataggaac cggtcgtgac gacgacgcca    960
tggtggtgcg catgcactag tacgtgagag ttggcggcca acatagattg ctggcgggcg   1020
ctagaagtgt gatgaggagc agtcgccagt cggtaggagg tagctggaag gtagctagat   1080
ttgcatgcgg gcgagcacgg tggcagcatc ggcggcggcg caggataagg acaaatggga   1140
ggtgcacatg gggctctgga aggctgtata ctgcttgaag tactaattgc aaaactttcg   1200
caagttgcaa aaaacccccct ccgtttacac ggataagact gacctaaacc aggtcatttg   1260
tcggaatggc ctaataattt attttataat aaggattaaa tgtattttat gtatcaccgc   1320
ggatggatac cgtatcgtac atctataagc gactaatcct tatacatcaa aaataatccc   1380
tcacctggcc tcctgctcga ctttggtttc aggcttgtgt ctctcttttt ctggcaaccc   1440
ttcacagttc ctgttcgtta tgtttgtggt gatgcgcatt tttaaggccc tgatgtaata   1500
atattactta catgagctag cagcagaagg cgatatcgga aatcaccaaa tctgatgtaa   1560
taatatcaat aatcctcgcc ttctgctgct agctcatgta attagtatcc tcactgtcag   1620
agaacggata ctggtacggg tacggccggg cggccggcca gccgtacgtg cgtcatacaa   1680
taaaggattc atatccggac actgctaccc tgtacccttt ccaggtcctg ggccctacat   1740
gagcatcagc tggctcatca ctttgcggcc ccgcgctgcg cagttcaact aagagtcgac   1800
gatgcgccaa tacagttcgg attacatcga cgactagaca atccagcgag taaatctccc   1860
aactccgcgt tgcattcgca ccattgggta cctgttcacg cgcacaacac acacaacctt   1920
cagcttccat tcagtctcat atactccccg atcccacgag tcgccgaacc tgtccgctgc   1980
actgaataca gtccgtttga                                               2000
```

<210> SEQ ID NO 44
<211> LENGTH: 299
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 44
aggcccctcg ccgacgccaa ctttgacacc ggttcctgtt aacccccccc cccccccccc 60
ccaacacccc ccccggcgaa ccaagcgacc cctcctcctg cccagtgcct tgtttagatg 120
gcgcagcgcc accactgccg cacaaagggc ttggatgtat attgatggtg ttggcatcct 180
gccgctccgt atccactgta actgagagac tcccaaaaat cacccggcat acgcctcatc 240
gcatccgcag agcacggtgc cagtcaccgg tgaatgttac atgcgaggtg gactgcatc 299

<210> SEQ ID NO 45
<211> LENGTH: 436
<212> TYPE: DNA
<213> ORGANISM: Tetraselmis sp.
<220> FEATURE:
<221> NAME/KEY: misc_feature
<223> OTHER INFORMATION: Nitrate Reductase Promoter

<400> SEQUENCE: 45
gcggcgccca ttgccgcgag gcggacgagc cgtcacggta gtgcgctgcc gctgctgcag 60
acggtgcctc ttggggttgt tcgggcatcc agcaggttcg gcctttgcgg ccagcacagg 120
cctgctcatc gcccctgcta cggcgctacc cgccgtgggg tcgcaacaca gctgctttag 180
cccacagcta tggtggtagt atctaccgta tgtcccagac tgcttcccct atgataccgc 240
cgccctgcgg tgcttgctta cactgttcac cgtgcggcgt ctgtccgtct ccaccccggc 300
ggcgtcgccg gggtcccgac tgatgtcacg cggcaacagc atcatctact gctggatgca 360
aaataatctg ctcgtcgcca aagcggcatc acgtgacagc aacaccgcaa cctccaaccc 420
gtacagcata tgacgc 436

<210> SEQ ID NO 46
<211> LENGTH: 658
<212> TYPE: DNA
<213> ORGANISM: Tetraselmis sp.
<220> FEATURE:
<221> NAME/KEY: misc_feature
<223> OTHER INFORMATION: Nitrate Reductase Terminator

<400> SEQUENCE: 46
ggcctgagct ggcagctggc ggagatcacg gagcgcgaga cgccgcggtg ggcggccaac 60
agcagcaatg acaaggccaa gcactggtgc tgggtgcgcc cccgtccccc ccccccttccc 120 ttttccccac ccaacactac cccatccata tatccatgta aaaccctagt tggggctcgc 180
ccagtggtta ggttgttgct ataggtgtcc agttgggggga ggaaggatgg atgggggagt 240
ttttgggggt ttttgtttgt cccaggggcg ggaaaaatac ccccatccat cgttcctccc 300
cggactggac acccatcgca ataaccgagc cactgggcga gccccatata gggtttcaca 360
ttagctgaaa cagcgtgaac ctgatataaa gatcctaaat ccttgcatat ttcaaaacaa 420
cctaagctca gcctagctct aaatcaaacc cacgtcaagg gcctgacacc gatagcccta 480
gaactgttaa cctcgctagg tatggcaact actcctgacc aagtttagtc attgggtggg 540
ccacaatcag ggttctgggg cataccctaa ccttatgccg aaacactggg gctacttcaa 600

```
ccctacaatc agacctgcat tgcaaccctg attatgcccg catatcctaa accctggc      658


<210> SEQ ID NO 47
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Promoter

<400> SEQUENCE: 47

cgaatcttcg ctttacggca cacccatctg aacgcccatc ccctcgacgt tagaaagcct     60

cagctcaaaa cctgcctcga tcaagttgta gtcctgtgag agggcttcta gtagagccac    120

tcacatcgag gtttgaggtt gcgacggcga tgcattttgc taaaccgaat tgctagtcga    180

tacacgctcc aaaaaatatg gattgactag ccttgactcg accttgtgcg cgtgcacaat    240

tgggctacag aattgagggg gtagtacagg catggcgggt tatacactag tagtcttggt    300

attgtgtcga cgcagtccaa tggaatcttg cgacgccatg gtgagtcggt ggggcttttt    360

ttagcgtttc ctagcgctat gtcactgcgg ctacgcagcc tcctgccgag ccgatgcgcc    420

accattgtta gcttcccttg acaacattcc accccctatag tagaccgagg tatgggatgc    480

cctagtggtg cccgcttggc gccccagagg cagcggtgtg tggctttgtt ggggatgggg    540

gactgttgga tattggaaaa ttgtatgggt acttgacgtc gtacggcgga taggtaaatg    600

acggattatt atccttgctt ggggtgcagt gtgaggtggc tttcctcctc tttgcagttg    660

ataccccttgc ggtagaggcg catatatacc gtgcattgga gaacattgtt gccggtgcat    720

agtgtacaca ctcatgcaat ggagctaagc cgctagtacg ggtgtgtgac aatattggag    780

caaaaaagcg ggcgcagcaa agcaggttaa ttacgcggag agagcaacat tttagcatta    840

gccagcatgc gcgacgcggc acgatcatgg cacccgccat gcgcatcgca ggcaagcgta    900

gcgtgcgata agtttagatt aataatatga tatgtaatcg taacattgtg gcattgatgc    960

atccatcacc acacatccat gatattaatg gtagccttgc atcggccggg agcgcaaggg   1020

gtttacaatt ccacactgta atcatgcggc tttttcttca taattgtcct atatgaatct   1080

tgcgcatgta ttgcatgtgg caataggttg cttgccaatg tgcactagct tgacatcacc   1140

actagcattg gtatcatagc ccaataattg cccaatcaac gcctacaact tttgaagtgt   1200

ttttggcagt actttactgt agaacctgtg aatgcagcgg gagagaaaaa gggccgctga   1260

aaaaggggcg aggggggggg gggggggca ctcaaaataa caaatcaact tgtcatggca   1320

ttacaatgat tcatatacaa ggatatctat atatattgtg ctttctaata cgctgtgcag   1380

cacgtggatc atggacgcaa cacgattcat aacctgccgt tatgaatcca aatgactgag   1440

cctggcgggc catcacgcgc gcgcacacgt gtgtacaggt actcgtacga tattcagtat   1500

cgcttccgtt cgtcgaacta tattatttat ctatcgtaag tatatttaat tatatttacg   1560

ggtatctatc gactactatc cagtcgctat tccccgtgct gtagcaggac tggacgaggg   1620

gtagagtaca ccaccactcg tggttgctgc ccggtgtatg gcgactacta atccggtata   1680

tgaggatcat actaaaaaat tgtccatccc atcgatcagg gcactacttc agcgccggct   1740

gcacatataa atagccgggc gcacgtcagc ctgcggggac cccactcatt catttttccg   1800

ccactccgcc acttcgagtc tgctcgagct tagccatctc accctggcct gctgcaaaag   1860

aggactgtct cctgtgcgac agcccacagg ggtgtcatag ctttccttcg cctcgagcca   1920

caaggcatat cgcgccaagg ctcgctatcc gccctttggc gacgtccgcc gttgaaaagg   1980
```

ccggaagata tcttcaaccg 2000

<210> SEQ ID NO 48
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Terminator

<400> SEQUENCE: 48
ggttaggtcg caatttccat cgctgagatc ggagaaggaa ggtctaatgc gtaattgcgc 60
acgtcaaaat ttctatgcat cagtactcaa cgctccattc tggccacgac atggcgtagt 120
acacgacccg tcagattgcc cccgcgggag ccttccttcg ttttcaattc aattctctct 180
gtcgcgactg gttttcacaa ccgcctccac actcaacaag tggagctcat tcgaatcacg 240
gttgaacatt gaccactgtc gtgcacgtat aataaacgca tctatcttcg ctgtctactt 300
gtactcgttg tatcagcatc gtcaacccgc gagcgctgga ccgtcctatt tttatagcgc 360
gagtaccact attttattat tttcttgaaa tagtcatacc aataataagc tcatgtatcg 420
gggtattggt gtagcgctcg actgaaaccg acacatatat cacagctgtg gcgctgctgt 480
agtcaataac ggtttttgct gtcgttcggt gtagcatagg caccgaatcg aacaaatatc 540
acggccaacg tttatggttc ggtgtaacag ttgccgaaac caactcaaaa tcatcgcaga 600
cgatttcgtt tctggtacgg tgtaagagat gtcgcggaat atattgatat acgactaatt 660
agaattattt tgtggttcgg tgtatccatc caggacggta gtataaatata tacccttcca 720 cataagtccg ggttttgcat tctcgatcgc aaagcgcatg catgggcgag gataccgccg 780
gctgcatgtg catacatgct aactacagtg ggaggagttc gggcaaacgc ctattgtgcg 840
ctttatacca cccgcgcgac aacacgacca tttgtggacg ccctttataa aacgcgaaat 900
cagtgcatga tgcgttggcg ctagaaaatt gcgggttgcg ccaaccgtcc aaacctatgg 960
aaatagcggc actcgtcgca ccaaactcga tgaatacggc cttggcatat gttgcacaca 1020
ccgtgcgtgt agtccactga aagcatgtcg ctataggcac gacgtgacac ccaacgacaa 1080
gctggccact gtgggagcag ttttgggtga aaatgctgct gtttctgtgg caaacgcacg 1140
taggagaggc ggtcgatggc ccttggcgta gggcgatgct ctactatggg ggcgcgtgtg 1200
gaatgccagt tgtaccgttt cgtggcgggt ggcgcggcag ggcgtggact ttaattaata 1260
tgaacttcat gaaaaatgct gtggaaaatg gcattttggc tggtagatgt gtgtatcgct 1320
aggaggcggc atatgccaag tgttggtggt ccatgttcat ccacacacat aatgctctcg 1380
cgcaaccgag tatgggctca gacacgcact tggcgcaaag ccacacgccc gacacgggtg 1440
ggcacatgag gcagtgagga gcggaaaaag ggcgattatt gagtcaaaat gggcacattt 1500
ctggactcaa aattgcaccc cccttaactc aaaattgtac cccttttggg gggtgcaaat 1560
ttgagttacg cctaacactg tacgaatgta ctgtgaaact ggcctttgac acattccttt 1620
tcttgccaac actgtacgag gtactattca gtgaaatgat cctgcactat gtactacacg 1680
cctgtccacc gcccttcgac gagatgcgtc gctacccttc catgctgacc gttttttctg 1740
gcctcgaatt ctacgccgcc attgtgcttc ccactcatct acccctcgca agctccctcg 1800
cgcttgtatt ctttgaggca tgttaacact tctcggtgct caaaagcatg gcagaccgtc 1860
ctcgcagagc aaaacgcaca tctgcccgct tgcagagtcc tgtgcgtggc gtggacatct 1920
gcggctgcag ttggctttga cccaacgagc agggctctcg acacactgct agtgacctcc 1980

```
atggcgcaag attctccgca                                          2000


<210> SEQ ID NO 49
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Promoter

<400> SEQUENCE: 49

gtgtgacaat atcggagcaa aaagcgggcg cagcaaagca ggtcaaccac gcgagagagc     60

aacattttag cattagccag catgcgcgac gcacgaccat ggcaccccat gcgcatcgca    120

ggcaagcgtg cgtgcgataa gtgtagatta ttaatatgat atgtaatcgt aaatttggca    180

ttgatcatcc atcaccaccc atccatgata ttaatggtag ccttgcatcg ctggagcgca    240

aggggtttac actttcacac tgtaatcatg cgcattactt cataatgtcc tatatgaatc    300

ttgcgcatgt attgcatgtg gcaataggtg cttgccaatg tgcactagct tgacatcacc    360

attagcattg gtatcatagc ccaataattg cccaatcaac tcctgcatct ttgaagtgtt    420

tttggcagta ctttactgta gaacctgtga ttgctgcagg agataaaagg gccgctgaaa    480

aagggcgagg gggggggca ctcaatataa caaatcaact tgtcatggca ttacaatgat    540

tcataacaat gatatctata tatatagtgc tttctaatac gctgtgaaga cgtggatcat    600

ggacgcaaca cgattcataa gctgccgtta tgatccaaat gactgagcct gcggccatca    660

cgcgcgcaca cgtgtacagg tactcgtacg atattcagta tcgcttccgt tcgtcgaact    720

attatttatc tatcgtaatt atatatttaa ttatattact acgggtatct atcgaatact    780

atccagtcgc tattccccgt gatgtagcag gactggacga ggggtagagt acaccacact    840

cgtggttgct gccggtgtat agcgactgct aatccggtat gaggacatac taaaaaatag    900

tccatcccat cgatcaggca ctatttcacg ccgctgcaca tataatagcc ggcgcacgtc    960

agcctgcgga ccccactcac tcatttttcc gccactccgc cacttcgagt ctgtcgagct   1020

aagccatctc accctggcct gctgcaaaga ggactgtctc ctgtgcgaca gcccacaggg   1080

tgtcatagct ttccttcgcc tcgagccaaa ggcatatcgc gccaaggctc gctatccgcc   1140

ctttggcgac gtccgccgtt gaaaaggccg gaagatatct tcaaccgatg gcgatgacaa   1200

cgactctccc gacggcgctt ggttggctgc gccggcgagc aggtgagcaa taacgcgtgc   1260

ctaatcactt tgactatctc gaagcgtgtt ccagcgtttg gaaaccctaa caaagggctc   1320

gcatctgcct cactcgcctg ctcgctgatg gcttattgcc gacgccagaa ctatttctgt   1380

cacgtgaccc aacgtcgttt gcgaagtcgc gttgccttca gtgcgcctca gccttgcctc   1440

agtcacattg ggtctgacag tacgagtgcc cagcttccag ccctctcctc cagttacact   1500

gtttatcact catgatatta gtggaatagg gggcagcgac actgctgtga cgaataaaag   1560

acttggtagt ggttccggag tcacgcccct aaaaactccg acactgtccg ggatataaat   1620

agtaagcatc actcgacgct agcgacgatg actccgacac gcacagctcc ggtgaatcac   1680

gccctcgcgt gctgtgtctt ctcgacactg ctacagtcct atgttacgcc tgttaactta   1740

accacctccg ccatgcatgc gtccgtgcgc aacaggaccg ccggcgcccg tcgaccctcg   1800

ccgccgtccg ccggtgcggc agctcgccgt tgttccattc caccgtgcgc ggagccgccc   1860

gtctcctgcc cgcagtggtc agcggccgcc gcagcccggc accccgttcg catcggccgc   1920

ttttggtggc ttccgctgag cccaaacggc gcgctcatgc gtcggcgacg tcgcagcgcg   1980
```

tcgtcgtggt cggcaacggc 2000

<210> SEQ ID NO 50
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Terminator

<400> SEQUENCE: 50
gctggcagcc tctactgcgg caaacgaggc atggatcgcc aaatcctcgc tgctcgacct 60
cattggcggg tatatttgcg cttctgctgg ccatggatca agacccggat gcggcggctg 120
cggtgtcgca ttattagcag tagtactatt gatatttaat gcacatgttt gtgcttagtc 180
gcaggtatgt atgtaagaca tgcaacaaga ttgctgtaga tttgttagtg tagcacgcca 240
atcgcatgct gtaaaattgc agaggcgttc ttggcaaatg tgatggcttg gttccactcg 300
ccatcagaga atgtcggctt cattgactta atttgcagat attgtggcaa cttcaagcat 360
ccctgcgtcg aggcgttcag caggctatct gaacgcatcc ctgtggctct gtgcagcatc 420
caacgattct ggaggcaccg ccattagttt accgactcaa catataggat atggtggtta 480
aggttaaggt cgcaattccc atcgctggag atcggagaag gaaggtctat gcgtaattgc 540
gcacgtcaaa tttcctatgc atcagtactc aacgctccat tctggccacg acatggcgta 600
gtacacgacc cgtcagattg cccccgcggg agccttcctt cgttttcaat tcaattctct 660
ctgtcgcgac tggttttcac aaccgcctcc acactcaaca agtggagctc attcgaatca 720
cggttgaaca ttgaccactg tcgtgcacgt ataataaacg catctatctt cgctgtctac 780
ttgtactcgt tgtatcagca tcgtcaaccc gcgagcgctg gaccgtccta tttttatagc 840
gcgagtacca ctattttatt atttttcttg aaatagtcat accaataata agctcatgta 900
tcggggtatt ggtgtagcgc tcgactgaaa ccgacacata tatcacagct gtggcgctgc 960
tgtagtcaat aacggttttt gctgtcgttc ggtgtagcat aggcaccgaa tcgaacaaat 1020
atcacggcca acgtttatgg ttcggtgtaa cagttgccga aaccaactca aaatcatcgc 1080
agacgatttc gtttctggta cggtgtaaga gatgtcgcgg aatatattga tatacgacta 1140
attagaatta ttttgtggtt cggtgtatcc atccaggacg gtagtataat atataccctt 1200
ccacataagt ccgggtttg cattctcgat cgcaaagcgc atgcatgggc gaggataccg 1260
ccggctgcat gtgcatacat gctaactaca gtgggaggag ttcgggcaaa cgcctattgt 1320
gcgctttata cccacccgcg cgacaacacg accatttgtg gacgcccttt ataaaacgcg 1380
aaatcagtgc atgatgcgtt ggcgctagaa aattgcgggt tgcgccaacc gtccaaacct 1440
atggaaatag cggcactcgt cgcaccaaac tcgatgaata cggcccttgg catatgttgc 1500
acacaccgtg cgtgtagtcc actgaaagca tgtcgctata ggcacgacgt gacaccccaa 1560
cgacaagctg gccactgtgg ggagcagttt tggggtgaaa atgctgctgt ttctgtggca 1620
aacgcacgta ggagaggcgg tcgatgggcc ccttggcgta gggcgatgct ctactatggg 1680
ggcgcgtggt ggaatgccag ttgtaccgtt tcgtgggcgg ggtggcgcgg caggggcgtg 1740
gactttaatt aatatgaact tcatgaaaaa tgctgtggaa aatggcattt tggctggtag 1800
atgtgtgtat cgctaggagg cggcatatgc caagtgttgg tggtccatgt tcatccacac 1860
acataatgct ctcgcgcaac cgagtatggg gctcagacac gcacttggcg caaagccaca 1920
cgcccgacac gggtgggcac atgaggcagt gaggagcgga aaaagggcga ttattgagtc 1980
aaaatgggca catttctgga 2000

<210> SEQ ID NO 51
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Promoter

<400> SEQUENCE: 51
atgaagcgcc cgcgaatctt cgctttacgg cacacccata tgaacgccca tcccctcgac 60
gttagaaagc ctcagctcaa aacatgcctc gatcaagttg tagtcctgtg agatggcttc 120
tagtagagcc actcacatcg aggtttgagg ttgcgacggc gatgcatttt gctaaaccga 180
attgctagtc gatactcgct caaaaaaatg tggattgact agccttgact cgaccttgtg 240
cgcgtgcacg attgggctac agaattgagg gggtagtaca ggcatggcct gtatacacta 300
gtagtcttgg tactgtgtcg acgcagtcca atggaatctt gcgacgccat ggtgagtcgg 360
tggggctttt cttagcgttt cctagcgcta tgtcactccg gctacgcagc ctcctgccga 420
gccgatgcgc caccattgtt agcttccctt gacaacattc caccccctata gtagaccgag 480 gtatgggatg cccttgtggt gcccgcttgg cgcccccaaac gcagcggtgt gtggctttgt 540
aggggatggg ggactgttgg atattggaaa atcgtatggg tacttgacgt cgtacggcgg 600
ataggtaaat gacggattat tatccttgct tggggtgcag tgtgaggtgg ctttcctcct 660
ctttgaagtt gataccccttg cggtagaggc gcatctatac catgcattgg agaacattgt 720
tgccggtgca tagtgtacac actcatgcaa aggagctaag ccgctagtac gagtgtgtga 780
caatatcgga gcaaaaaagc gggcgcagca aagcaggtca accacgcgga gagagcaaca 840
ttttagcatt agccagcatg cgcgacgcac gaccatggca cccgccatgc gcatcgcagg 900
caagcgtagc gtgcgataag tgtagattat taatatgata tgtaatcgta aaattgtggc 960
attgattcat ccatcaccac ccatccatga tattaatggt agccttgcat cggctgggag 1020
cgcaaggggt ttacactttc acactgtaat catgcggcat tacttcataa tcgtcctata 1080
tgaatcttgc gcatgtattg catgtggcaa taggttgctt gccaatgtgc actagcttga 1140
catcaccatt agcattggta tcatagccca ataattgccc aatcaactcc tgcatctttt 1200
gaagtgtttt tggcagtact ttactgtaga acctgtgatt gctgcaggag aataaaaggg 1260
ccgctgaaaa aggggcgagg gggggggcac tcaatataac aaatcaactt gtcatggcat 1320
tacaatgatt cataaacaat gatatctata tatatagtgc tttctaatac gctgtgaagt 1380
acgtggatca tggacgcaac acgattcata agctgccgtt atgaatccaa atgactgagc 1440
ctggcggcca tcacgcgcgc gcacacgtgt gtacaggtac tcgtacgata ttcagtatcg 1500
cttccgttcg tcgaactatt atttatctat cgtaattatt atatttaatt atattgacta 1560
cgggtatcta tcgaatacta tccagtcgct attccccgtg atgtagcagg actggacgag 1620
gggtagagta caccaccact cgtggttgct gcccggtgta tagcgactgc taatccggta 1680
tgaggatcat actaaaaaat agttcatccc atcgatcagg gcactatttc agcgccggct 1740
gcacatataa atagccgggc gcacgtcagc ctgcgggaac ccccactcact catttttccg 1800 ccactccgcc acttcgagtc tgctcgagct aagccatctc accctggcct gctgcaaagg 1860
aggactgtct cctgtgcgac agcccacagg ggtgtcaaag ctttccttcg cctcgagtca 1920
caaggcatat cgcaccaagg ctcgctatcc gccctttggc gacgtccgcc gttgaaaagg 1980

```
ccggaagata tcttgaaccg                                              2000


<210> SEQ ID NO 52
<211> LENGTH: 2000
<212> TYPE: DNA
<213> ORGANISM: Tetraselmis sp.
<220> FEATURE:
<221> NAME/KEY: misc_feature
<223> OTHER INFORMATION: Nitrite Reductase Terminator

<400> SEQUENCE: 52

gctggcagcc tctactgcgg caaacgaggc atggatggcc aaatcctcgc tgctcgacct     60

cattggcggg tatatttgcg cttctgctgg atcatggatc aagacgtgga tgaggcggct    120

gcggtgttgc attcttagca gtagtactat tgatatttaa ggcacatgtt tgtgcttaga    180

cgcaggtatg tatgtaagac atgcaacaag attgctgtag atttgttagt gtagcacgcc    240

aatcgcatgc tgtaaaattg cagaggcgtt cttggcaaat gttatggctt ggttccactc    300

gccatcagag gatgtcggct tcactgactt tgcaaatagt gtagcaactt caagcatccc    360

tgcgtcgagg cgttcagcag gctatctgaa cacatccctg tggctctgtg cagcatctaa    420

cgattctgga ggcaccgcca ttagtttacc gattaccgac atataggata tggtggttaa    480

ggttagggtc gcaatctcca tcgctgaaga tcggagaagg gaggtctatg cgcaactgcg    540

cacgtcaaat tccctatgca tcactactca aggctccatt gtggccacga catggcgtag    600

tacacgaccc gtcaggttgc ccccgcggga gccttccttt gttttcaatt caattctctg    660

tcgcgactga ttttcacaac cgcctccaca ctcaacaagt ggggctcttt cgaatcacgg    720

ctgaacatta accactgtcg tgcacgtata attaacgcct gtatcttcgc tgtctacttg    780

tactcgtatc agcatcgtcc gcccgcgagc gctggaccgt cctattttta tagcgctagt    840

accactacag gtattttatt atttttcttg aaataatcat accaataata agctcatgta    900

tcggggtatt ggtgtagcgc tcgactgaaa ccgacacata tatcacagct gtggcgctgc    960

tgtagtcaat aacggctttg ctgtcgttcg gtgtagcata ggcaccgaat cgaagaaata   1020

tcacggacaa ccttcatggt tcggtgtaac agttgccgaa accaacccaa aataatcgca   1080

gacgatttcg tttctggtac ggtaaaagag atgtcgccga atatattgat atacgactaa   1140

ctagaattat tttgtggttc ggtgtatcca tccaggacgg tagtataaca tacaccgctc   1200

cacataggtc cgagttttgc attctcgatc gcaaagcgca tgcatgggcg aggataccgc   1260

cggctgcatg tgcttacatg ctaactacag tgggaagagt tcgggcaaac gcctattgtg   1320

cgctttgtac ccacccacgc gacaacacga ccatttgtgg gcgctcttta taaaatgcga   1380

aatcattgca taatgcgttg gcgctagaaa attgcgggtt gcgccaaccg tccaaaccta   1440

tgcaaatagc gtcactagtt gcaccaaact cgatgaatac ggcccttggc ataagttgca   1500

cacaccgtgc gtgtagtcca ctgaaagcat gtcgctatag gcacgccgtg acaccccaac   1560

gacaagttgg ccactgtggg gagcagtttt ggggtgaaaa tgttgctgtt tctgtgtcga   1620

acgcacgtag gagaggcgct cgatggcccc cttggtgtag gtcaatgctc tactatgggg   1680

gcgcgtggtg gaatgccagt tgcaccgttt cgtgggcggg gtggcgcggt aggggcgtgg   1740

actttaatta atatgaactt ccttaaaaaa tgctgtggaa aatggcattt tggctggacg   1800

atgtgtgtat cgcaaggagg cggcatttgc caagtgttgg tggtctatgg tcattcacac   1860

acataacgct ctcgcgcaac cgagtatggg gctcagacac gcacgtggcg caaagccacg   1920

cgcccgacat gggtgggtac atgaggcagt gcggagcaac ttggatgatc atctttgggg   1980
```

```
atttttccg gggcccccga                                             2000


<210> SEQ ID NO 53
<211> LENGTH: 2909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cre coding sequence w/ N-terminal NLS of sv40

<400> SEQUENCE: 53

atgcccaaga agaagcggaa agtcgggagc aatctgttga ccgtgcatca ggtatcgaga      60

agaactaaag agcgttcaaa cgcatcaata ttttgctaaa gagctttaca tctttttggg     120

gctattttct ggctactcgg tagtgacttg accactttct tcccaagtgg gggcaagccg     180

ataagccgct gtgaccgttg attttttat aaaagacgta gacatgttca atcagccaca      240

attgatatgc ttgaatacag aacctgcccg cattgcctgt tgacgcaaca tctggtgagc     300

tgcggttgct atcctcccaa tataacctga agtcatgcat atattcgcac taatctacat     360

cccatgttgt gttgagctat tcggtattga tgccagctca gtgaactaat tatcaaatgt     420

atatcggtgc tgccagaatc gatccatgta tcaatgccac aagtaactgg agatacattt     480

gctacatgta gatgaggtgc gcaagaacct gatggacatg tttagggacc gccaagcctt     540

cagcgagcat acatggaaga tgctgctgag cgtgtgcaga tcttgggcag catggtgtaa     600

gctgaacaac cgcaagtggt tcccagcaga acccgaaggt atgcctgggt aactgtcaaa     660

atcatgtata ttcccgcaat gcaagtggtt cattgttgtg ctttacgtta aagacgtgtc     720

agctgcagga gaattatttt gaggatgatt gtccgttgtt ggcgatgtct tgcattgtga     780

agtatgtttt gaagtcatac aggaagtgtg aaatcccaaa gcagctggct gccgctgcat     840

gcgaccagtc attcacctgc attgtgtgtg ctgtagatgt gagggactat ctgctgtacc     900

tgcaagcaag gggactggca gtgaagacca ttcagcagca tctgggacag ctgaacatgc     960

tgcataggag gtctggactg cctaggccaa gcgatagcaa tgcagtgtct ctggtgatgc    1020

gccgcattag aaaggagaac gtggatgctg ggagagggc aaaacaagca ctggcatttg    1080

agcgcaccga ctttgaccaa gtgaggtggg cttcgcaact gctgcctgaa cttcctgttc    1140

ctgtgcatgt acatgagagt cggttggaac aggctcatac tgcgcctgat tgataggctg    1200

tcccacattg ttttatttgc tgtatcgatg tattcatttt gcattgggtc ctttctgctc    1260

atgaagcacc aagaaggctg gctgtcaatg gcatgccagc tcatgccatc tggatgacat    1320

tatgcaagac cagtgttgac tcgaacatga atcttactgg aaactttaat gaatgctttc    1380

gagcttttg tgcaggtctc tgatggagaa ctcagaccgc tgccaagaca tccgcaatct    1440

ggcatttctg ggatcgcct acaacacact gctgaggatt gccgagatcg cacgcattag    1500

ggtgaaggac attagccgca cagatggagg gaggatgctg atccatatcg ggaggacaaa    1560

gaccctggtg agcacagctg gagtggagaa agcactgtct ctgggagtga ccaaggtaag    1620

cttaccatgt gtttatatga agctgatatt tggaagaaag gaggaagcaa cgacaacaag    1680

ggcggtgcac aatctattgc cgcttttgaa tcttgcccgc aaaggcagtc gatgattgct    1740

cactgtatca ggttgattta gttgatgagg tgtagctggg gaagctccaa tccccagtcc    1800

agatagcctt ggttatgaat tgcataatgt aggcaccact tgcactggtc ctaaacccca    1860

gttcattcct gtccttctcg tgcattttgt caaatgaaca tgcaaccgag tgtgttttcc    1920
```

```
tactcgacat gtgtgcgatt gcccacgtgt gctgcagctg gtggaacggt ggattagcgt   1980

gtctggagtg gcagatgacc ccaacaacta cctgttttgc cgcgtgcgca agaatggagt   2040

tgctgcacct agcgcaacca gtcaactgtc tacaagggca ctggagggga tctttgaggc   2100

aacacatcgc ctgatctacg gggcaaagga tgattctggg cagaggtatc tggcctggtc   2160

tggacattct gcaagggttg gagcagcaag ggacatggca agagctggag tgagcattcc   2220

cgagatcatg tgagaggccc cagcaaaaac aacagcacta gctgttgctg ctcagtttgt   2280

gctcgtgatg tttgaaagga atggacaagg ttcatccatg atgttcatta tctgggctgg   2340

tcttgtacat ggggttattc tatactaaac aggagcgata caaataacaa acaatcaatg   2400

tctatataca catatacttg gctaaatttt tctcccggcc ttacatacat aacaaaggct   2460

aaactaattg acccaaaata attgtatgaa taatcaaatt gatgcataca aataatccta   2520

aaaatgaaaa aaatttcatt gaaataagta tagaaataac aaatgtttga cccacagccc   2580

tcactctcca acccaatcct gcctctcaca agacttgcca tgtaccaact tacaatgaca   2640

gcgagctaca acaagttcca tcaaggtgtg ggttgctatt agttggtgga acgtttgtac   2700

atttcacagt tggacatgca cttgcgaaaa aggcgttggc ttcagtgagg cagtgcttgc   2760

tcgtatcccc tccaagcatg ccttgtgcac ccattttgca acgcaggcaa gctggagggt   2820

ggacaaacgt gaacatcgtg atgaactaca tccgcaacct ggacagcgag actggagcaa   2880

tggtgagact gctggaggat ggggattaa                                     2909
```

```
<210> SEQ ID NO 54
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: forward primer sequence for Cre

<400> SEQUENCE: 54

gatctttgag gcaacacatc g                                               21
```

```
<210> SEQ ID NO 55
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: reverse primer sequence for Cre

<400> SEQUENCE: 55

aatgctcact ccagctcttg                                                 20
```

```
<210> SEQ ID NO 56
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: forward primer sequence for qRT-PCR

<400> SEQUENCE: 56

gcctttggtt atcgtgcttt ag                                              22
```

```
<210> SEQ ID NO 57
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: reverse primer sequence for qRT-PCR

<400> SEQUENCE: 57

tccctccgat cctttactct c                                              21
```